US010450404B2

(12) United States Patent
Utsunomiya et al.

(10) Patent No.: US 10,450,404 B2
(45) Date of Patent: Oct. 22, 2019

(54) PRODUCTION METHODS OF POLYESTER AND POLYURETHANE

(71) Applicants: MITSUBISHI CHEMICAL CORPORATION, Chiyoda-ku (JP); GENOMATICA, INC., San Diego, CA (US)

(72) Inventors: Masaru Utsunomiya, Tokyo (JP); Yusuke Izawa, Mie (JP); Norikazu Konishi, Mie (JP); Kota Tanaka, Mie (JP); Shinichiro Matsuzono, Mie (JP); Takayuki Suzuki, Mie (JP); Michael Japs, San Diego, CA (US); Mark Burk, San Diego, CA (US); Warren Clark, Lake Jackson, TX (US)

(73) Assignees: MITSUBISHI CHEMICAL CORPORATION, Chiyoda-ku (JP); Genomatica, Inc., San Diego, CA (US)

( * ) Notice: Subject to any disclaimer, the term of this patent is extended or adjusted under 35 U.S.C. 154(b) by 0 days.

(21) Appl. No.: 14/560,830

(22) Filed: Dec. 4, 2014

(65) Prior Publication Data
US 2015/0087789 A1 Mar. 26, 2015

Related U.S. Application Data

(63) Continuation of application No. PCT/JP2013/065371, filed on Jun. 3, 2013.

(30) Foreign Application Priority Data

Jun. 5, 2012 (JP) ................................ 2012-128066
Feb. 28, 2013 (JP) ................................ 2013-039247

(51) Int. Cl.
*C08G 18/42* (2006.01)
*C08G 63/16* (2006.01)
*C08G 63/183* (2006.01)
*C08G 18/66* (2006.01)
*C12P 7/18* (2006.01)

(52) U.S. Cl.
CPC ......... *C08G 18/4213* (2013.01); *C08G 18/42* (2013.01); *C08G 18/4238* (2013.01); *C08G 18/664* (2013.01); *C08G 63/16* (2013.01); *C08G 63/183* (2013.01); *C12P 7/18* (2013.01)

(58) Field of Classification Search
CPC ......... C12P 7/18; C08G 63/16; C08G 63/183; C08G 18/4213; C08G 18/4238; C08G 18/42; C08G 18/664
See application file for complete search history.

(56) References Cited

U.S. PATENT DOCUMENTS

| 2005/0069997 A1 | 3/2005 | Adkesson et al. |
| 2006/0173157 A1 | 8/2006 | Endo et al. |
| 2009/0171037 A1 | 7/2009 | Aoshima et al. |
| 2010/0159520 A1* | 6/2010 | Diner ........................ C08H 8/00 435/72 |
| 2011/0003355 A1 | 1/2011 | Clark et al. |
| 2011/0009531 A1 | 1/2011 | Aoshima et al. |
| 2011/0152581 A1 | 6/2011 | Adkesson et al. |
| 2011/0152583 A1 | 6/2011 | Adkesson et al. |
| 2011/0288207 A1 | 11/2011 | Aoshima et al. |
| 2013/0030145 A1 | 1/2013 | Aoshima et al. |
| 2013/0035448 A1 | 2/2013 | Ohara et al. |
| 2013/0338395 A1 | 12/2013 | Ohara et al. |
| 2014/0322777 A1 | 10/2014 | Clark et al. |
| 2015/0087034 A1 | 3/2015 | Utsunomiya et al. |
| 2015/0087038 A1 | 3/2015 | Utsunomiya et al. |

FOREIGN PATENT DOCUMENTS

| CN | 1816629 A | 8/2006 |
| CN | 101163729 A | 4/2008 |
| EP | 2 857 377 A1 | 4/2015 |
| JP | 2-99555 A | 4/1990 |
| JP | 8-294586 A | 11/1996 |
| JP | 2004-107619 A | 4/2004 |
| JP | 2007-502325 | 2/2007 |
| JP | 2007-197654 A | 8/2007 |
| JP | 2008-101143 * | 5/2008 |
| JP | 2008-101143 A | 5/2008 |
| JP | 2011-122144 | 6/2011 |
| JP | 2011-225851 | 11/2011 |
| JP | 2012-097289 | 5/2012 |
| WO | WO 2004/087783 A1 | 10/2004 |

(Continued)

OTHER PUBLICATIONS

Szycher, Michael; Szycher's Handbook of Polyurethanes; CRC Press; New York; 1999; pp. 5-1-5-4.*
U.S. Appl. No. 15/560,800, filed Dec. 4, 2014, US2015/0087034 A1, Utsunomiya et al.
International Search Report dated Sep. 3, 2013 in PCT/JP2013/065371 (with English language translation).
International Preliminary Report on Patentability and Written Opinion dated Dec. 9, 2014 in PCT/JP2013/065371.
Extended European Search Report dated Mar. 1, 2016 in Patent Application No. 13800445.2.

(Continued)

*Primary Examiner* — Rabon A Sergent
(74) *Attorney, Agent, or Firm* — Oblon, McClelland, Maier & Neustadt, L.L.P.

(57) ABSTRACT

At the time of producing a polyester by using a dicarboxylic acid component and a biomass-resource-derived diol as raw materials, a polyester is efficiently produced with good color tone, as the raw material diol derived from biomass resources, a diol in which the content of a cyclic carbonyl compound having a carbon atom number of 5 or 6 is from 0.01 to 12 ppm by mass, is used, and by controlling the content of a cyclic carbonyl compound having a carbon atom number of 5 or 6 in the raw material diol to fall in a prescribed range, the color tone of the polyester is improved.

25 Claims, 2 Drawing Sheets

(56) References Cited

FOREIGN PATENT DOCUMENTS

| WO | WO2004/101479 A2 | 11/2004 |
|---|---|---|
| WO | WO2004/101479 A3 | 11/2004 |

OTHER PUBLICATIONS

"Sustainably Produced Bio-based I,4-Butanediol-Fermentation from Renewable Sugar (e.g. Dextrose), Recovery, Purification (including Distillation) from By-Products, and Uses as an Interchangeable Substitute for Petroleum-derived I,4-butanediol in Making Polyesters and other Polymers", ip.com Journal, IPCOM000227994D, XP013157527, May 31, 2013, pp. 1-5 and Cover Sheet.

Combined Taiwanese Office Action and Search Report dated Oct. 7, 2016 in Patent Application No. 102119876 (with English language translation).

Office Action dated Feb. 28, 2017, in Japanese Application No. 2013-117831, filed Jun. 4, 2013 (w/ computer generated English-language Translation).

Office Action dated Apr. 3, 2019 in the corresponding European Patent Application No. 13 800 445.2.

* cited by examiner

PRODUCTION METHODS OF POLYESTER AND POLYURETHANE

TECHNICAL FIELD

The present invention relates to production methods of a polyester and a polyurethane. More specifically, the present invention relates to methods for producing a polyester and a polyurethane with good color tone by using a diol obtained from biomass recourses, such as 1,4-butanediol.

BACKGROUND ART

A polyester such as aromatic polyester, aliphatic polyester, wholly aromatic polyester, semi-aromatic polyester and polycarbonic acid ester has been conventionally produced by polycondensing a petroleum-derived raw material. However, in view of recent concerns about fossil fuel depletion and global-scale environmental problems such as increase in carbon dioxide in the air and in addition, with the growing call for establishment of a circulation-type (sustainable) society, in regard to the polyester as well, practical application of a polyester using, as the raw material diol or dicarboxylic acid, a material derived from biomass resources such as plant and furthermore, a biomass plastic using the polyester, is advancing. When an yearly renewable plant is used as the raw material, the raw material supply can be irrelevant to the fossil fuel depletion and moreover, because of carbon dioxide absorption for plant growth, a great contribution to the reduction of atmospheric carbon dioxide can be afforded.

Out of polyester feedstocks, as to a dicarboxylic acid such as succinic acid and adipic acid, various methods for the production from glucose by using a fermentation process are known, in addition to the conventional chemical process. With respect to a diol as well, there are known, for example, a method of obtaining 1,4-butanediol (hereinafter, sometimes simply referred to as "1,4BG"), 1,3-propanediol, ethylene glycol, etc. by directly fermenting the biomass resource such as plant in bacterial cells, and a method of producing a carboxylic acid in bacterial cells from biomass resources such as plant by a fermentation process and then hydrogenating the dicarboxylic acid with the aid of a reducing catalyst to obtain a diol (Non-Patent Document 1).

In addition, out of polyurethanes produced on an industrial scale, a polyurethane of a polyester polyol type where the soft segment is typified by a dicarboxylic acid-based polyester, is obtained by reacting a polyester polyol and an isocyanate compound, and the polyester polyol is produced using a diol and a dicarboxylic acid derivative as raw materials and therefore, can similarly produced from a plant-derived raw material.

A polyester containing a diol in the constituent units is industrially very useful. In particular, a polybutylene terephthalate (hereinafter, sometimes simply referred to as "PBT") that is a representative engineering plastic among thermoplastic polyesters is excellent in easiness of molding process, mechanical properties, heat resistance, chemical resistance, aroma retentivity and other physical and chemical properties and therefore, is widely used for an injection molded article such as automotive component, electric/electronic component and precision equipment component. In addition, the polyester has recently found a widespread application also in the general consumer appliance field such as film, sheet, monofilament and fiber by making use of its excellent properties and in turn, PBT with good color tone is being required.

Alternatively, an aliphatic polyester such as polybutylene succinate (hereinafter, sometimes referred to as "PBS") and polybutylene succinate adipate has biodegradability that is a property of biograding the polymer into carbon dioxide and water with microorganisms in soil or water. Such a polyester is produced at present by polycondensing a raw material derived from fossil fuel resources, and a technique for deriving a raw material of the polyester from renewable biomass resources is expected to become very important in the future. With respect to this biodegradable polyester as well, a polymer having good color tone is required due to a recent spread of demand over various fields.

Furthermore, the above-described polyurethane of a polyester polyol type has a feature of being excellent in the heat resistance, weather resistance, etc. and is applied to a wide range of uses.

Among these polyesters, PBT is usually produced by reacting a terephthalic acid or an alkyl ester thereof with 1,4BG, and when 1,4BG as the raw material is obtained from biomass resources, PBT is deteriorated in the color tone compared with a polymer obtained from a fossil fuel such as petroleum. The main causes of this deterioration in color tone include the presence of a nitrogen atom-containing component in PBT.

For example, Patent Document 1 describes a technique for obtaining a polyester by using biomass resources as the raw material, where a polyester having a nitrogen content of 1,000 ppm by mass or less is obtained by controlling the nitrogen content in the raw material dicarboxylic acid.

Also, Patent Document 2 describes a technique for obtaining PBT by using biomass resources as the raw material, where PBT having a nitrogen atom content of 50 ppm by mass or less is obtained by controlling the nitrogen atom content in the raw material 1,4-butanediol derived from biomass resources to a range of 0.01 to 50 ppm by mass. Furthermore, it is stated that 1,-acetoxy-4-hydroxybutane (hereinafter, sometimes simply referred to as "1,4HAB") in 1,4BG retards the polycondensation reaction of PBT and thereby causes coloring in the obtained PBT but when 1,4BG having a controlled nitrogen atom concentration is used as the raw material, coloring of PBT due to retardation of the polymerization can be reduced.

However, this patent document neither discloses nor suggests that a specific carbonyl compound in 1,4BG greatly affects the color tone of the obtained polyester, and moreover, is silent on the content of the specific carbonyl compound having a great effect on the coloring.

BACKGROUND ART DOCUMENT

Patent Document

Patent Document 1: JP-A-2005-139287 (the term "JP-A" as used herein means an "unexamined published Japanese patent application")
Patent Document 2: JP-A-2008-101143

Non-Patent Document

Non-Patent Document 1: Appl. Microbiol Biotechnol, No. 51 (1999), pp. 545-552

SUMMARY OF INVENTION

Problem that Invention is to Solve

It is generally known that a carbonyl compound or an acetal compound in the raw material deteriorates the color tone at the time of production of a polyester, but among the compounds having the same carbonyl group or olefin bond, the degree of effect on coloring of the produced polyester differs based on the structure of each compound. The present inventors have focused attention on the fact that this effect appears to a most prominent degree, among polyesters, in PBT and PBS, and among polyurethanes, in a thermoplastic polyurethane and a polyester polyol that is a prepolymer thereof. For example, when PBT is produced using a biomass-resource-derived 1,4BG as a raw material, the deterioration of color tone is more outstanding than in the case of using the conventional 1,4BG produced from a fossil fuel such as petroleum. The reason therefor is that a carbonyl compound by-produced at the time of production of a biomass-resource-derived 1,4BG and contained in 1,4BG has a significant effect on the deterioration of color tone of PBT, compared with a carbonyl compound by-produced at the time of producing the conventional 1,4BG from a fossil fuel such as petroleum, but the reason has not been heretofore sufficiently clarified.

The present invention has been made by taking into account those problems, and an object of the present invention is to provide methods for producing a polyester and a polyurethane by using a dicarboxylic acid component and a biomass-resource-derived diol as raw materials, where a polyester and a polyurethane are efficiently produced with good color tone.

Means for Solving Problem

As a result of intensive studies to attain the above-described object, the present inventors have found that at the time of producing a polyester and a polyurethane by using a raw material diol derived from biomass resources, such as biomass-resource-derived 1,4BG, the content of, among carbonyl compounds in the raw material diol, a cyclic carbonyl compound having a carbon atom number of 5 or 6 is strongly correlated with the color tone of the obtained polyester and polyurethane. Then, it has been found that the color tone of the obtained polyester and polyurethane is improved by controlling the content of the compound above in the raw material diol to a specific range.

That is, the gist of the present invention resides in the following [1] to [22].

[1] A method for producing a polyester by using, as raw materials, a dicarboxylic acid component and a diol produced directly from a biomass-resource-derived substance by a fermentation process, wherein a content of a cyclic carbonyl compound having a carbon atom number of 5 or 6 in the diol is 12 ppm by mass or less.

[2] The method for producing a polyester as described in [1] above, wherein the cyclic carbonyl compound having a carbon atom number of 5 or 6 contains a compound having a structure represented by the following formula (I):

[Chem. 1]

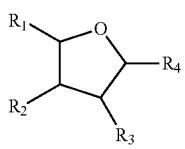

Formula (I)

(wherein in formula (I), each of $R_1$ to $R_4$ independently represents a hydrogen atom, a methyl group, a formyl group or an acetyl group, any one of $R_1$ to $R_4$ is a formyl group or an acetyl group, and the total number of carbon atoms contained in respective groups of $R_1$ to $R_4$ is 2 or less).

[3] The method for producing a polyester as described in [1] above, wherein the cyclic carbonyl compound having a carbon atom number of 5 or 6 contains a compound having a structure represented by the following formula (II):

[Chem. 2]

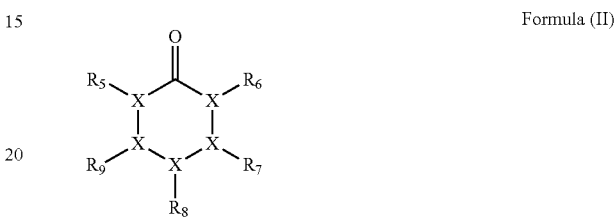

Formula (II)

(wherein in formula (II), X represents a carbon atom or an oxygen atom, the oxygen atom number out of these atoms is 1, each of $R_5$ to $R_9$ independently represents a methyl group or a hydrogen atom, and the total number of carbon atoms contained in respective groups of $R_5$ to $R_9$ is 1 or less).

[4] The method for producing a polyester as described in [1] above, wherein the cyclic carbonyl compound having a carbon atom number of 5 or 6 contains a compound having a structure represented by the following formula (III) and a content of the compound having a structure represented by formula (III) in the diol is 6 ppm by mass or less:

[Chem. 3]

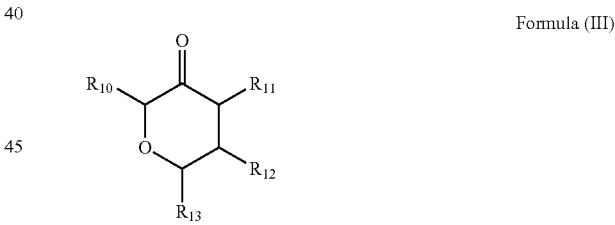

Formula (III)

(wherein in formula (III), each of $R_{10}$ to $R_{13}$ independently represents a methyl group or a hydrogen atom, and the total number of carbon atoms contained in respective groups of $R_{10}$ to $R_{13}$ is 1 or less).

[5] The method for producing a polyester as described in any one of [1] to [4] above, wherein the diol is 1,4-butanediol,
the dicarboxylic acid component is at least one of a terephthalic acid and a terephthalic acid alkylate, and
the polyester is polybutylene terephthalate.

[6] The method for producing a polyester as described in [5] above, wherein the 1,4-butanediol contains from 1 to 99 ppm by mass of 1-acetoxy-4-hydroxybutane.

[7] The method for producing a polyester as described in any one of [1] to [6] above, wherein a content of a nitrogen atom compound in the diol is from 0.1 to 50 ppm by mass in terms of nitrogen atom.

[8] A method for producing a polyester polyol by using, as raw materials, a dicarboxylic acid component and a diol produced directly from a biomass-resource-derived substance by a fermentation process, wherein a content of a cyclic carbonyl compound having a carbon atom number of 5 or 6 in the diol is 100 ppm by mass or less.

[9] The method for producing a polyester polyol as described in [8] above, wherein the cyclic carbonyl compound having a carbon atom number of 5 or 6 contains a compound having a structure represented by the following formula (I):

[Chem. 4]

Formula (I)

(structure with $R_1$, $R_2$, $R_3$, $R_4$ on an oxygen-containing five-membered ring)

(wherein in formula (I), each of $R_1$ to $R_4$ independently represents a hydrogen atom, a methyl group, a formyl group or an acetyl group, any one of $R_1$ to $R_4$ is a formyl group or an acetyl group, and the total number of carbon atoms contained in respective groups of $R_1$ to $R_4$ is 2 or less).

[10] The method for producing a polyester polyol as described in [8] above, wherein the cyclic carbonyl compound having a carbon atom number of 5 or 6 contains a compound having a structure represented by the following formula (II):

[Chem. 5]

Formula (II)

(structure with $R_5$, $R_6$, $R_7$, $R_8$, $R_9$ and X atoms forming a six-membered ring with a carbonyl)

(wherein in formula (II), X represents a carbon atom or an oxygen atom, the oxygen atom number out of these atoms is 1, each of $R_5$ to $R_9$ independently represents a methyl group or a hydrogen atom, and the total number of carbon atoms contained in respective groups of $R_5$ to $R_9$ is 1 or less).

[11] The method for producing a polyester polyol as described in [8] above, wherein the cyclic carbonyl compound having a carbon atom number of 5 or 6 contains a compound having a structure represented by the following formula (III) and a content of the compound having a structure represented by formula (III) in the diol is 50 ppm by mass or less:

[Chem. 6]

Formula (III)

(structure with $R_{10}$, $R_{11}$, $R_{12}$, $R_{13}$ on an oxygen-containing six-membered ring with a carbonyl)

(wherein in formula (III), each of $R_{10}$ to $R_{13}$ independently represents a methyl group or a hydrogen atom, and the total number of carbon atoms contained in respective groups of $R_{10}$ to $R_{13}$ is 1 or less).

[12] The method for producing a polyester polyol as described in any one of [8] to [11] above, wherein the diol is 1,4-butanediol, the dicarboxylic acid component is at least one of a terephthalic acid and a terephthalic acid alkylate, and the polyester polyol is polybutylene adipate.

[13] The method for producing a polyester polyol as described in [12] above, wherein the 1,4-butanediol contains from 1 to 99 ppm by mass of 1-acetoxy-4-hydroxybutane.

[14] The method for producing a polyester polyol as described in any one of [8] to [13] above, wherein a content of a nitrogen atom compound in the diol is from 0.1 to 50 ppm by mass in terms of nitrogen atom.

[15] A method for producing a polyurethane, comprising:

reacting a polyester polyol produced by the production method of a polyester polyol described in any one of [8] to [14] above with an isocyanate compound.

[16] A method for producing a polyurethane, comprising:

a step of reacting a polyester polyol and an isocyanate compound, wherein the polyester polyol and a diol used as a raw material for the production of the polyester polyol are a diol produced directly from a biomass-resource-derived substance by a fermentation process and a content of a cyclic carbonyl compound having a carbon atom number of 5 or 6 in the diol is 12 ppm by mass or less.

[17] The method for producing a polyurethane as described in [16] above, wherein the cyclic carbonyl compound having a carbon atom number of 5 or 6 contains a compound having a structure represented by the following formula (I):

[Chem. 7]

Formula (I)

(structure with $R_1$, $R_2$, $R_3$, $R_4$ on an oxygen-containing five-membered ring)

(wherein in formula (I), each of $R_1$ to $R_4$ independently represents a hydrogen atom, a methyl group, a formyl group or an acetyl group, any one of $R_1$ to $R_4$ is a formyl group or an acetyl group, and the total number of carbon atoms contained in respective groups of $R_1$ to $R_4$ is 2 or less).

[18] The method for producing a polyurethane as described in [16] above,
wherein the cyclic carbonyl compound having a carbon atom number of 5 or 6 contains a compound having a structure represented by the following formula (II):

[Chem. 8]

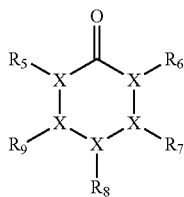

Formula (II)

(wherein in formula (II), X represents a carbon atom or an oxygen atom, the oxygen atom number out of these atoms is 1, each of $R_5$ to $R_9$ independently represents a methyl group or a hydrogen atom, and the total number of carbon atoms contained in respective groups of $R_5$ to $R_9$ is 1 or less).

[19] The method for producing a polyurethane as described in [16] above,
wherein the cyclic carbonyl compound having a carbon atom number of 5 or 6 contains a compound having a structure represented by the following formula (III) and a content of the compound having a structure represented by formula (III) in the diol is 6 ppm by mass or less:

[Chem. 9]

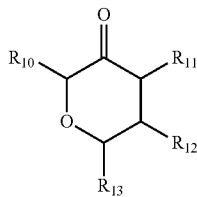

Formula (III)

(wherein in formula (III), each of $R_{10}$ to $R_{13}$ independently represents a methyl group or a hydrogen atom, and the total number of carbon atoms contained in respective groups of $R_{10}$ to $R_{13}$ is 1 or less).

[20] The method for producing a polyurethane as described in any one of [16] to [19] above,
wherein the diol is 1,4-butanediol, and
the polyester polyol is polybutylene adipate.

[21] The method for producing a polyurethane as described in [20] above,
wherein the 1,4-butanediol contains from 1 to 99 ppm by mass of 1-acetoxy-4-hydroxybutane.

[22] The method for producing a polyurethane as described in any one of [16] to [21] above,
wherein a content of a nitrogen atom compound in the diol is from 0.1 to 50 ppm by mass in terms of nitrogen atom.

Effects of Invention

According to the present invention, a polyester and a polyurethane each having high quality and good color tone can be produced using a diol derived from biomass resources. Particularly in the case of producing PBT by using 1,4BG derived from biomass resources, the present invention provides a remarkable effect that PBT with good color tone can be produced.

MODE FOR CARRYING OUT INVENTION

Figure 1:
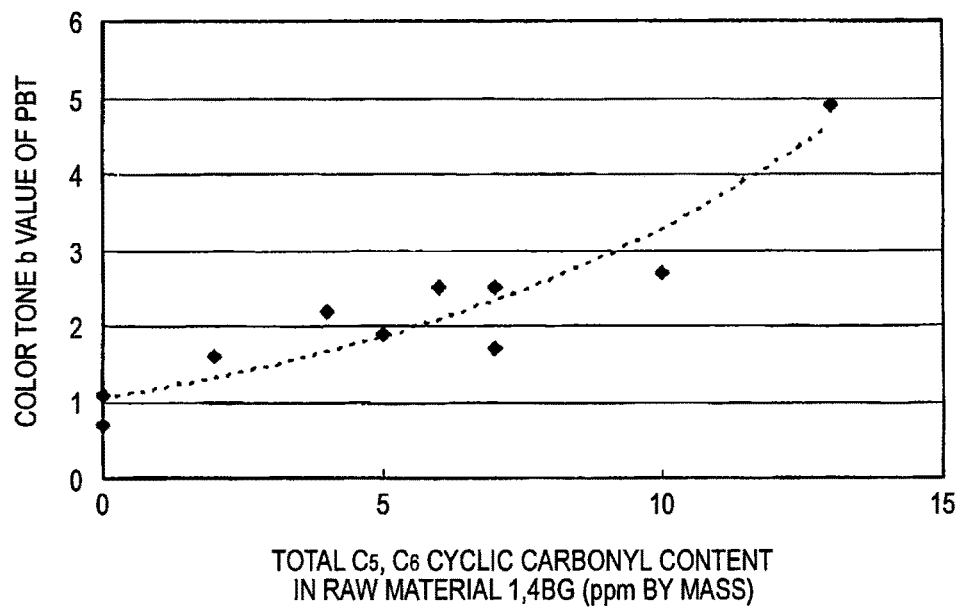
FIG. 1 is a graph showing the correlation between the content of a cyclic carbonyl compound having a carbon atom number of 5 or 6 in the bio-process 1,4BG used as a PBT feedstock in Examples 1 to 9 and Comparative Example 1 and the color tone b value of the obtained PBT.

The present invention is described in detail below, but the constitutional requirements described below are a representative example of the embodiment of the present invention, and the present invention is not limited thereto.

Incidentally, in the description of the present invention, the numerical value range expressed using "to" means a range including the numerical values before and after "to" as the lower limit value and the upper limit value, respectively. Also, in the description of the present invention, the lower limit value or upper limit value means a range including the value of the lower limit value or upper limit value.

[Raw Material for Production of Polyester]

First, the raw material for the production of a polyester in the production method of a polyester of the present invention is described below. In the following description, the "dicarboxylic acid feedstock" and the "diol feedstock" mean, respectively, a dicarboxylic acid component and a diol component as raw materials in the production of a polyester. In addition, the "dicarboxylic acid component" is a generic term encompassing a dicarboxylic acid and a dicarboxylic acid derivative such as dicarboxylic acid alkylate.

The dicarboxylic acid feedstock for use in the present invention may be a dicarboxylic acid component produced by either a method using, as the raw material, a fossil fuel such as petroleum (hereinafter, sometimes simply referred to as "fossilization process") or a method of producing the component from biomass resources through a fermentation step, or by a combination thereof.

Out of the dicarboxylic acid feedstocks for use in the present invention, the aromatic dicarboxylic acid component includes a terephthalic acid, an isophthalic acid, their lower alcohol esters, etc., and in view of polymerizability, a terephthalic acid and dimethyl terephthalate are preferred. The aliphatic dicarboxylic acid component includes a dicarboxylic acid such as oxalic acid, succinic acid, glutaric acid, adipic acid, sebacic acid and dodecanoic diacid, and their lower alcohol esters and anhydrides (e.g., succinic anhydride, adipic anhydride). From the viewpoint of physical properties of the obtained polyester, the aliphatic dicarboxylic acid is preferably succinic acid, adipic acid, sebacic acid, dodecanoic diacid or an anhydride or lower alcohol ester thereof, more preferably succinic acid. One of these dicarboxylic acid feedstocks may be used alone, or two or more thereof may be mixed and used. Here, the lower alcohol as referred to above usually means an alcohol having a carbon number of 1 to 4.

On the other hand, the diol feedstock for use in the present invention must be a diol derived from biomass resources. Specific examples of the diol feedstock include ethylene glycol, 1,3-propanediol, 2-methyl-1,3-propanediol, neopentyl glycol, 1,4-butanediol, 1,5-pentanediol, 1,6-hexanediol, 1,4-cyclohexanediol, 1,4-cyclohexanedimethanol, and isosorbide. In view of physical properties of the obtained polyester, ethylene glycol, 1,3-propanediol and 1,4-butanediol are preferred, and in view of heat resistance, 1,4-butanediol is more preferred. One of these diol feedstocks may be used alone, or two or more thereof may be mixed and used.

For such a diol feedstock, a diol component produced directly from a biomass-resource-derived substance such as glycol by a fermentation process is used. Here, 1,4BG produced directly from a biomass-resource-derived substance such as glucose by a fermentation process is most preferred.

The combination of the dicarboxylic acid feedstock and the diol feedstock is not particularly limited as long as a polyester can be produced, but preferred combinations include a combination of terephthalic acid and 1,4BG, a combination of dimethyl terephthalate and 1,4BG, and a combination of succinic acid and 1,4BG. That is, the production method of a polyester of the present invention is suitable for the production of polybutylene terephthalate (PBT) by copolymerization of terephthalic acid and 1,4BG, the production of polybutylene terephthalate (PBT) by copolymerization of dimethyl terephthalate and 1,4BG, and the production of polybutylene succinate (PBS) by copolymerization of succinic acid and 1,4BG.

[Biomass-Resource-Derived Diol]

The diol feedstock for use in the production of PBT of the present invention is derived from biomass resources, and this is preferred in view of environmental conservation.

The biomass resource encompasses those stored after sunlight energy is converted in the form of starch, cellulose, etc. through photosynthesis of plants; animal bodies growing by eating plant bodies; products obtained by processing plant bodies or animal bodies; and the like. Specifically, the biomass resource includes wood, rice straw, rice bran, old rice, corn, sugar cane, cassava, sago palm, bean-curd refuse, corncob, tapioca refuse, bagasse, vegetable oil cake, potato, buckwheat, soybean, fats and oils, wastepaper, papermaking residue, aquatic product residue, livestock excrement, sewage sludge, food waste, etc. Among these, plant resources such as wood, rice straw, old rice, corn, sugar cane, cassava, sago palm, bean-curd refuse, corncob, tapioca refuse, bagasse, vegetable oil cake, potato, buckwheat, soybean, fats and oils, wastepaper and papermaking residue are preferred; wood, rice straw, old rice, corn, sugar cane, cassava, sago palm, potato, fats and oils, wastepaper, papermaking residue, etc. are more preferred; and corn, sugar cane, cassava and sago palm are most preferred.

The biomass resource generally contains a nitrogen atom and many alkali metals and alkaline earth metals, such as Na, K, Mg and Ca.

Although the method therefor is not particularly limited, these biomass resources are guided to a carbon source through, for example, known steps of pretreatment and saccharification, e.g., a chemical treatment with an acid, an alkali, etc., a biological treatment using microorganism, or a physical treatment. This step often involves a step for size reduction by a pretreatment such as chipping, shaving or grinding of the biomass resource and if desired, further involves a pulverization step using a grinder or a mill. The thus size-reduced biomass resource is usually further guided to a carbon source through steps of pretreatment and saccharification. Specific methods therefor include a chemical method, for example, an acid treatment with a strong acid such as sulfuric acid, nitric acid, hydrochloric acid and phosphoric acid, an alkali treatment, an ammonia freezing-steaming-blasting method, a solvent extraction, a supercritical fluid treatment, and an oxidizing agent treatment; a physical method such as micro-grinding, steaming-blasting method, microwave treatment and electron beam irradiation; a biological treatment such as hydrolysis by microorganism or enzymatic treatment; and the like.

As the carbon source derived from biomass resources, there is usually used a fermentable carbohydrate, for example, a hexose such as glucose, mannose, galactose, fructose, sorbose and tagatose; a pentose such as arabinose, xylose, ribose, xylulose and ribulose; a disaccharide and a polysaccharide, such as pentosan, saccharose, starch and cellulose; a fat or oil such as butyric acid, caproic acid, caprylic acid, capric acid, lauric acid, myristic acid, palmitic acid, parmitoleic acid, stearic acid, oleic acid, linoleic acid, linolenic acid, monocutinic acid, arachidic acid, eicosenoic acid, arachidonic acid, behenic acid, erucic acid, docosapentaenoic acid, docosahexaenoic acid, lignoceric acid and ceracoleic acid; and polyalcohols such as glycerin, mannitol, xylitol and ribitol. Among these, a hexose such as glucose, fructose, xylose and saccharose, a pentose, and a disaccharide are preferred, and glucose is more preferred. As the plant resource-derived carbon source in a broader sense, a cellulose that is the main component of paper is also preferred.

Usually, a diol such as 1,4BG is synthesized using such a carbon source through a fermentation process utilizing microbial conversion, a chemical conversion process involving a reaction step such as hydrolysis, dehydration reaction, hydration reaction and oxidation reaction, or a combination of the fermentation process and the chemical conversion process. Above all, a fermentation process by microbial conversion is preferred.

In the case of using a biomass-resource-derived 1,4BG as the diol feedstock, the biomass-resource-derived 1,4BG is 1,4BG directly produced from a carbon source such as glucose by a fermentation process. Here, 1,4BG directly produced by a fermentation process is preferably subjected to, if desired, purification such as distillation and then used as the raw material for the production of a polyester. Also, the content of the later-described cyclic carbonyl compound having a carbon atom number of 5 or 6 is preferably adjusted in the purification step.

Furthermore, a method of producing 1,4BG from biomass resources by a combination with a known organic chemical catalytic reaction is also used. For example, in the case of utilizing pentose as the biomass resource, 1,4BG can be easily produced by a combination of a known dehydration reaction and a known catalytic reaction.

<Content of a Cyclic Carbonyl Compound Having a Carbon Atom Number of 5 or 6 in the Biomass-Resource-Derived Diol>

As a result of intensive studies, the present inventors have found that when producing a polyester by using a biomass-resource-derived diol, among others, when producing PBT or PBS, a cyclic carbonyl compound having a carbon atom number of 5 or 6 contained in the diol has the effect of a significant deterioration in the color tone of the obtained polyester.

The cyclic carbonyl compound having a carbon atom number of 5 or 6 includes a compound having a 5-membered ring or 6-membered ring structure and in particular, having an oxygen atom-containing cyclic skeleton. Specifically, the compound includes one or more compounds selected from the group consisting of compounds having structures represented by the following formulae (I), (II) and (III):

[Chem. 10]

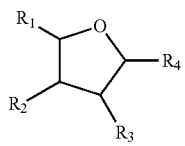

Formula (I)

(wherein in formula (I), each of $R_1$ to $R_4$ independently represents a hydrogen atom, a methyl group, a formyl group or an acetyl group, any one of $R_1$ to $R_4$ is a formyl group or an acetyl group, and the total number of carbon atoms contained in respective groups of $R_1$ to $R_4$ is 2 or less);

[Chem. 11]

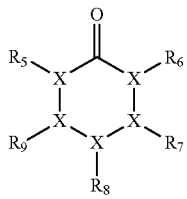

Formula (II)

(wherein in formula (II), X represents a carbon atom or an oxygen atom, the oxygen atom number out of these atoms is 1, each of $R_5$ to $R_9$ independently represents a methyl group or a hydrogen atom, and the total number of carbon atoms contained in respective groups of $R_5$ to $R_9$ is 1 or less); and

[Chem. 12]

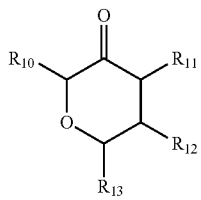

Formula (III)

(wherein in formula (III), each of $R_{10}$ to $R_{13}$ independently represents a methyl group or a hydrogen atom, and the total number of carbon atoms contained in respective groups of $R_{10}$ to $R_{13}$ is 1 or less).

More specifically, as examples of the compound having a structure represented by formula (I), the compound having a carbon atom number of 5 includes tetrahydro-2-furaldehyde, tetrahydro-3-furaldehyde, etc. and the compound having a carbon atom number of 6 includes 2-acetyltetrahydrofuran[1-(tetrahydrofuran-2-yl)ethanone], 3-acetyltetrahydrofuran[1-(tetrahydrofuran-3-yl)ethanone], 5-methyltetrahydro-2-furaldehyde, 4-methyltetrahydro-2-furaldehyde, 3-methyltetrahydro-2-furaldehyde, 2-methyltetrahydro-3-furaldehyde, 4-methyltetrahydro-3-furaldehyde, 5-methyltetrahydro-3-furaldehyde, 2-(tetrahydrofuran-2-yl)acetaldehyde, 3-(tetrahydrofuran-2-yl)acetaldehyde, etc.

As examples of the compound having a structure represented by formula (II), the compound having a carbon atom number of 5 includes tetrahydro-4H-pyran-4-one, etc. and the compound having a carbon atom number of 6 includes 3-methyltetrahydro-4H-pyran-4-one, 2-methyltetrahydro-4H-pyran-4-one, 2-formyl-tetrahydropyran, 3-formyl-tetrahydropyran, 4-formyl-tetrahydropyran, etc.

As examples of the compound having a structure represented by formula (III), the compound having a carbon atom number of 5 includes dihydro-2H-pyran-3(4H)-one, etc. and the compound having a carbon atom number of 6 includes 2-methyldihydro-2H-pyran-3(4H)-one, 4-methyldihydro-2H-pyran-3(4H)-one, 5-methyldihydro-2H-pyran-3(4H)-one, 6-methyldihydro-2H-pyran-3(4H)-one, etc.

Preferably, as examples of the compound having a structure represented by formula (I), the compound having a carbon atom number of 5 is tetrahydro-2-furaldehyde, and the compound having a carbon atom number of 6 is 2-acetyltetrahydrofuran[1-(tetrahydrofuran-2-yl)ethanone], 3-acetyltetrahydrofuran[1-(tetrahydrofuran-3-yl)ethanone] or 5-methyltetrahydro-2-furaldehyde; as the compound having a structure represented by formula (II), the compound having a carbon atom number of 5 is tetrahydro-4H-pyran-4-one, and the compound having a carbon atom number of 6 is 2-methyltetrahydro-4H-pyran-4-one or 2-formyl-tetrahydropyran; and as the compound having a structure represented by formula (III), the compound having a carbon atom number of 5 is dihydro-2H-pyran-3(4H)-one, and the compound having a carbon atom number of 6 is 2-methyldihydro-2H-pyran-3(4H)-one, 4-methyldihydro-2H-pyran-3(4H)-one, 5-methyldihydro-2H-pyran-3(4H)-one or 6-methyldihydro-2H-pyran-3(4H)-one.

More preferably, as the compound having a structure represented by formula (I), the compound having a carbon atom number of 5 is tetrahydro-2-furaldehyde, and the compound having a carbon atom number of 6 is 2-acetyltetrahydrofuran[1-(tetrahydrofuran-2-yl)ethanone]; as the compound having a structure represented by formula (II), the compound having a carbon atom number of 5 is tetrahydro-4H-pyran-4-one, and the compound having a carbon number of 6 is 2-methyltetrahydro-4H-pyran-4-one; and as the compound having a structure represented by formula (III), the compound having a carbon atom number of 5 is dihydro-2H-pyran-3(4H)-one, and the compound having a carbon atom number of 6 is 2-methyldihydro-2H-pyran-3(4H)-one, 4-methyldihydro-2H-pyran-3(4H)-one or 5-methyldihydro-2H-pyran-3(4H)-one.

These cyclic carbonyl compounds having a carbon atom number of 5 or 6 are thought to be derived from biomass resources, among others, from sugar used as a raw material for fermentation and is presumed to be produced in the fermentation step and/or refining step by cyclization of polyhydric alcohols having a carbon atom number of 5 or 6 derived from pentose and/or hexose. That is, in the fermentation process using biomass resources for the raw material, a chemical product is produced from a sugar such as glucose. At this time, the sugar is converted to a target compound, carbon dioxide, acetic acid, etc. but a polyfunctional compound remains as a sugar residue. In addition, it may also be envisaged that the sugar itself does not completely disappear, and the residual sugar is dehydrated by heating in a distillation column, etc. as a post-step and produces a new component. The cyclic carbonyl compound having a carbon atom number of 5 or 6 is presumed to be produced from these sugar-derived residual impurities in the fermentation step and/or refining step.

The abundance of the cyclic carbonyl compound having a carbon atom number of 5 or 6 in the biomass-resource-derived diol that is provided as a product by refining a biomass-resource-derived diol by distillation, etc. is considered to be a very small amount, but this compound when contained even in a very small amount in the diol used as a raw material of the polyester exerts a significant effect on the obtained polyester, particularly, on the color tone of PBT.

The reason therefor is that since the biomass-resource-derived diol usually contains a nitrogen atom-containing compound as described later, the production of a polyester such as PBT involves the possibility of allowing the cyclic carbonyl compound having a carbon atom number of 5 or 6 contained in the diol feedstock to react with a nitrogen atom-containing compound in the diol and produce various derivatives such as amid; amine and amino acid and the derivative is considered to strongly deteriorate the color tone of the polyester such as PBT.

The content of the cyclic carbonyl compound having a carbon atom number of 5 or 6 in the biomass-resource-derived diol working out to a raw material of the polyester in the present invention is, in terms of the mass ratio to the diol, usually 12 ppm or less, preferably 10 ppm or less, more preferably 5 ppm or less, still more preferably 3 ppm or less. When the content of the cyclic carbonyl compound having a carbon atom number of 5 or 6 in the biomass-resource-derived diol, particularly, in 1,4BG is not more than the upper limit above, the color tone of a polyester in the production thereof, particularly, the color tone at the time of PBT production, is improved. Incidentally, in the present invention, the color tone of the obtained polyester can also be controlled by adjusting the raw material diol to have a content of the cyclic carbonyl compound having a carbon atom number of 5 or 6 in the above-described range.

The reason why the content of the cyclic carbonyl compound having a carbon atom number of 5 or 6 in the biomass-resource-derived diol used as a raw material for the production of a polyester, which is not more than the upper limit above, is preferred in view of color tone of the obtained polyester, is not clearly known but is presumed because the production volume of various derivatives rich in reactivity, such as amide, amine and amino acid, produced by a reaction of the cyclic carbonyl compound considered to cause deterioration of the color tone of the polyester with a nitrogen atom-containing compound, as described above, can be reduced.

Among others, the compound having a structure represented by formula (III) significantly deteriorates the color tone of a polyester such as PBT and therefore, the upper limit of the content of the compound having a structure represented by formula (III) in the diol feedstock for use in the present invention is, in terms of the mass ratio to the diol, usually 6 ppm, preferably 5 ppm, more preferably 2 ppm, still more preferably 1 ppm. When the content of the compound having a structure represented by formula (III) in the biomass-resource-derived diol, particularly, in 1,4BG, is not more than the upper limit above, the color tone in the polyester production, particularly, in the PBT production, tends to become good.

Incidentally, in the present invention, the content of the cyclic carbonyl compound having a carbon atom number of 5 or 6 in the biomass-resource-derived diol indicates the total content of a cyclic carbonyl compound having a carbon atom number of 5 and a cyclic carbonyl compound having a carbon atom number of 6, and this content may be determined using a factor computed from the effective carbon coefficient after analyzing the cyclic carbonyl compound by gas chromatography (GC) but for the sake of simplicity, may also be calculated from an area ratio in GC analysis. The content of the cyclic carbonyl compound having a carbon atom number of 5 or 6 in the diol feedstock is specifically measured by the method described in Examples later.

In the present invention, it is important for obtaining a polyester with good color tone to reduce the content of the cyclic carbonyl compound having a carbon atom number of 5 or 6 in the raw material diol, and as long as the content of the cyclic carbonyl compound can be reduced to a predetermined value or less, any process for reducing the content of the cyclic carbonyl compound having a carbon atom number of 5 or 6 may be employed.

The content of the cyclic carbonyl compound having a carbon atom number of 5 or 6 in the biomass-resource-derived diol has a greater effect in the case of directly producing 1,4BG by a fermentation process, because a crystallization or large-scale hydrogenation step, e.g., via succinic acid is not necessary and the cyclic carbonyl compound is carried over together with 1,4BG directly to a refining step such as distillation.

In the case where the diol feedstock is 1,4BG, since the cyclic carbonyl compound having a carbon atom number of 5 or 6 is a component lighter in the boiling point than 1,4BG, it is effective in reducing the content of the cyclic carbonyl compound to previously remove light-boiling point components containing a cyclic carbonyl compound having a carbon atom number of 5 or 6 from 1,4BG by distillation before using 1,4BG as the raw material for the production of a polyester. The content of the cyclic carbonyl compound can also be reduced by converting the compound to an alcohol by hydrogenation before distilling and separating light-boiling-point components.

Specifically, crude 1,4BG containing the cyclic carbonyl compound having a carbon atom number of 5 or 6, water, light-boiling-point byproducts and high-boiling-point byproducts is separated into a plurality of factions by batch distillation, whereby refined 1,4BG reduced in the content of the cyclic carbonyl compound having a carbon atom number of 5 or 6 can be obtained in desired purity. From an economical viewpoint, the distillation is preferably operated in a continuous mode.

That is, the crude 1,4BG containing the cyclic carbonyl compound having a carbon atom number of 5 or 6, water, light-boiling-point byproducts and high-boiling-point byproducts can be refined in a continuous mode by dehydration distillation, light-boiling separation distillation and high-boiling separation distillation. Preferably, product refining distillation is further added to the dehydration distillation, light-boiling separation distillation and high-boiling separation distillation, and more preferably, the refining can be performed by a refining process further including a hydrogenation step of hydrogenating the cyclic carbonyl compound that is a coloring component. The hydrogenation catalyst used for the hydrogenation of the cyclic carbonyl compound may be arbitrary as long as it is a catalyst capable of hydrogenating a carbonyl compound such as ketone and aldehyde, but among others, a solid catalyst containing at least a metal such as Ni, Pd, Ru, Pt and Cu is preferably used. The order of respective steps above may be arbitrary, but the crude 1,4BG is preferably refined through, in order, dehydration distillation, high-boiling separation distillation, hydrogenation step, light-boiling separation distillation, and product refining distillation. The distillation mode in each of the hydrogenation and other steps may be either in continuous mode or batch mode, but in view of profitability, an operation in continuous mode is preferred.

In general, the separation distillation of the cyclic carbonyl compound having a carbon atom number of 5 or 6 from 1,4BG can be performed as light-boiling separation distillation by multistage distillation using a packing and/or a tray, where the cyclic carbonyl compound having a carbon atom number of 5 or 6 is separated as a light-boiling-point component. At this time, the cyclic carbonyl compound can be distilled out from the top part and top periphery of a light-boiling separation distillation column. Furthermore, refined 1,4BG can be obtained as a side stream from the top part or top periphery of a product refining distillation column subsequent to the light-boiling separation distillation column. On this occasion, refined 1,4BG is obtained as a side stream from the top periphery, and 1,4BG and light-boiling components including the cyclic carbonyl compound having a carbon atom number of 5 or 6 are distilled out from the top part, whereby refined 1,4BG more reduced in the content of the cyclic carbonyl compound having a carbon atom number of 5 or 6 can be obtained. These light-boiling separation distillation column and product refining distillation column are preferably operated at a relatively low temperature, and specifically, from the standpoint of avoiding increase of new impurities, the operation is preferably performed such that the maximum temperature in the column becomes 180° C. or less.

<Content of 1-Acetoxy-4-Hydroxybutane in Biomass-Resource-Derived 1,4BG>

Out of biomass-resource-derived diols, the impurity contained in the diol feedstock produced particularly through a fermentation step includes acetic acid, butyric acid, tetrahydrofuran, 2-hydroxytetrahydrofuran, gamma-butyrolactone, 1-acetoxy-4-hydroxybutane, 1,3-butanediol, 2,3-butanediol, and 2-(4-hydroxybutyloxy)tetrahydrofuran. These are components lighter in the boiling point than 1,4BG and can be removed together with a cyclic carbonyl compound having a carbon atom number of 5 or 6 in the light-boiling separation distillation step for distilling and separating a cyclic carbonyl compound having a carbon atom number of 5 or 6. Out of these light-boiling impurities, as for 1-acetoxy-4-hydroxybutane (1,4HAB), the upper limit of its content in 1,4BG preferred as the diol feedstock in the present invention is preferably 99 ppm by mass, more preferably 90 ppm by mass, still more preferably 80 ppm by mass, and most preferably 70 ppm by mass. The lower limit is preferably 0.1 ppm by mass, more preferably 0.2 ppm by mass, and in particular, from the economical view point in the refining step, the lower limit is preferably 0.5 ppm by mass. As the 1,4HAB content in 1,4BG is smaller, for example, the polycondensation reaction rate in the PBT production and the color tone of PBT produced are more likely to become desirable. On the other hand, as the content is larger, the refining step tends to become simpler, which is economically advantageous.

Here, the content of 1,4HAB in 1,4BG is measured by the method described in Examples later.

As for the 1,4HAB content in the raw material 1,4BG derived from biomass resources, the 1,4HAB content in 1,4BG is preferably adjusted by previously refining the biomass-resource-derived 1,4BG before feeding it to a reaction vessel for the production of PBT.

In this case, 1,4HAB is a component lighter in the boiling point than 1,4BG; and the 1,4HAB content in 1,4BG can be adjusted by separating and distilling light-boiling-point components in the 1,4BG refining step.

In the case where 1,4BG is directly obtained by fermentation of the biomass resource, the 1,4HAB content can be adjusted, for example, by the fermentation conditions, conditions of neutralization with ammonia, and refining conditions including distillation of the obtained 1,4BG, and also in this case, it is a suitable technique to remove light-boiling-point components including 1,4HAB by performing refining of 1,4BG.

The separation distillation of 1,4HAB from 1,4BG can be performed at the time of separation distillation of the cyclic carbonyl compound having a carbon atom number 5 or 6 from 1,4BG.

<Content of a Nitrogen Atom-Containing Compound in the Biomass-Resource-Derived Diol>

A diol derived from biomass resources sometimes contains, as an impurity, a nitrogen atom-containing compound ascribable to fermentation treatment and refining treatment involving a step of neutralization with an acid. Specifically, a nitrogen atom-containing compound, for example, derived from amino acid, protein, ammonia, urea and fermentation bacteria is contained.

The upper limit of the content of the nitrogen atom-containing compound in the biomass-resource-derived diol working out to a raw material of the polyester in the present invention is, as the mass ratio to the diol, in terms of nitrogen atom, usually 50 ppm, preferably 20 ppm, more preferably 10 ppm, still more preferably 5 ppm. The lower limit is not particularly limited but is usually 0.01 ppm, preferably 0.1 ppm, and in view of profitability such as load reduction in the refining step, more preferably 0.2 ppm. When the content of the nitrogen atom-containing compound in the biomass-resource-derived diol is not more than the upper limit above, for example, the polycondensation reaction rate in the polyester production and the color tone of the polyester produced are more likely to become desirable. The reason why the content of the nitrogen atom-containing compound in the biomass-resource-derived diol used as the diol feedstock, which is not more than the upper limit above, is likely to be advantageous in view of, for example, the polycondensation reaction rate and color tone, is not clearly known but is presumed because the production of a coloration-inducing substance acting to inhibit the polycondensation reaction and deteriorate the color tone of a polyester, other than the nitrogen atom-containing compound, can be suppressed in the refining step involving treatment and distillation of the fermentation liquid for the control of the content of the nitrogen atom-containing compound in the diol.

For example, the biomass-resource-derived diol for use in the present invention contains gamma-butyrolactone, and the gamma-butyrolactone is thought to produce a nitrogen atom-containing compound and various derivatives such as amide, amine and amino acid. Since these derivatives are a component having bifunctionality or higher functionality and being rich in the reactivity, a component that strongly deteriorates the color tone of a polyester is possibly present in these derivatives. In addition, as described above, various derivatives produced by the reaction of a nitrogen atom-containing compound and a cyclic carbonyl compound having a carbon atom number of 5 or 6, such as amide, amine and amino acid, are also considered to be causative of coloring.

In the case where the diol such as 1,4BG is directly obtained by fermentation of the biomass resource, the content of the nitrogen atom-containing compound in the raw material 1,4BG derived from biomass resources can be adjusted, for example, by the fermentation conditions, conditions of neutralization with ammonia, adsorption of amino acid by an ion exchange resin, and refining conditions including distillation of the obtained diol.

[Production Method of Polyester]

The production to which the production method of a polyester of the present invention using the above-described biomass-resource-derived diol is suitably applicable includes productions of PBT and PBS. In the following, the production method of an aliphatic polyester including PBS, and the production method of PBT are described.

<Production of Aliphatic Polyester>

A polyester such as PBS is produced using the above-described aliphatic dicarboxylic acid component and the biomass-resource-derived diol component according to the present invention by subjecting these components to an esterification and/or transesterification reaction and then to a polycondensation reaction under reduced pressure.

The reaction conditions in the esterification and/or transesterification reaction step can be set as follows.

As for the reaction temperature, the lower limit is usually 150° C., preferably 180° C., more preferably 200° C., and the upper limit is usually 250° C., preferably 240° C., more preferably 230° C. If the reaction temperature is less than the lower limit above, the esterification reaction rate is low, and a long reaction time is required. On the other hand, if the reaction temperature exceeds the upper limit above, generation of foreign matters due to increase of scattering materials in the reaction tank or decomposition of the diol component or dicarboxylic acid component tends to often occur.

As for the reaction pressure, the lower limit is usually 50 kPa, preferably 60 kPa, more preferably 70 kPa, and the upper limit is usually 200 kPa, preferably 130 kPa, more preferably 110 kPa. If the reaction pressure is less than the lower limit above, scattering materials are likely increased in the reaction tank to bring about a high haze of the reaction product, giving rise to increase of foreign matters, and in addition, the portion of the diol component distilled out of reaction system tends to increase, leading to decrease in the esterification reaction rate. On the other hand, if the pressure exceeds the upper limit above, it is likely that the portion of the diol component dehydrated and decomposed is increased to incur a reduction in the esterification rate.

The reaction time is usually 1 hour or more, and the upper limit is usually 10 hours, preferably 4 hours.

The reaction conditions in the reduced-pressure polycondensation reaction step subsequent to the esterification and/or transesterification reaction step may be set as follows.

As for the reaction temperature, the lower limit is usually 180° C., preferably 200° C., more preferably 220° C., and the upper limit is usually 270° C., preferably 265° C., more preferably 260° C. If the reaction temperature is less than the lower limit above, the polycondensation reaction rate is low, and a long reaction time is required. In addition, the melt viscosity becomes too high, making it difficult to withdraw a polymer. On the other hand, if the reaction temperature exceeds the upper limit above, generation of foreign matters due to increase of scattering materials in the reaction tank or decomposition of the diol component or dicarboxylic acid component tends to often occur.

As for the final achievable pressure at the time of polycondensation reaction, the lower limit is usually 0.01 kPa, preferably 0.05 kPa, more preferably 0.1 kPa, and the upper limit is usually 1 kPa, preferably 0.8 kPa, more preferably 0.5 kPa. Setting of the reaction temperature to a range of less than the lower limit above requires an expensive vacuum apparatus, and this is not economical. On the other hand, if the pressure exceeds the upper limit above, reduction in the polycondensation rate is likely to be caused, and a side reaction from an alcohol terminal as the base point readily proceeds, incurring an increase in the terminal acid valence.

The reaction time is usually 1 hour or more, and the upper limit is usually 10 hours, preferably 4 hours.

In the esterification and/or transesterification reaction step and the polycondensation reaction step, the reaction is promoted by using a reaction catalyst. However, in the esterification and/or transesterification reaction step, a sufficiently high reaction rate can be obtained even without an esterification reaction catalyst. Also, when an esterification reaction catalyst is present at the time of esterification reaction, the catalyst may produce a deposit insoluble in the reaction product due to water produced by the esterification reaction, leading to impairment of the transparency of the polyester obtained (that is, increase in the haze), or may be heterogenized. Therefore, it is preferred that a reaction catalyst is not added and not used during the esterification reaction.

In the polycondensation reaction step, the reaction is difficult to proceed without a catalyst, and therefore, a catalyst is preferably used.

As the polycondensation reaction catalyst, in general, a metal compound containing at least one member out of metal elements belonging to Groups 1 to 14 of the long-form Periodic Table is used (hereinafter, unless otherwise specified, the "Periodic Table" indicates the long-form Periodic Table). The metal element specifically includes scandium, yttrium, samarium, titanium, zirconium, vanadium, chromium, molybdenum, tungsten, tin, antimony, cerium, germanium, zinc, cobalt, manganese, iron, aluminum, magnesium, calcium, strontium, sodium, potassium, etc. Among these, scandium, yttrium, titanium, zirconium, vanadium, molybdenum, tungsten, zinc, iron and germanium are preferred, and titanium, zirconium, tungsten and germanium are more preferred.

Furthermore, in order to reduce the terminal acid value affecting the thermal stability of the polyester, among metal elements above, metal elements belonging to Groups 3 to 6 of the Periodic Table, which show Lewis acidity, are preferred. Specifically, the metal elements are scandium, titanium, zirconium, vanadium, molybdenum and tungsten. Above all, titanium and zirconium are preferred in terms of ease of availability, and titanium is more preferred from the viewpoint of reaction activity.

As the catalyst, a compound containing an organic group such as carboxylate salt, alkoxy salt, organic sulfonate salt and β-diketonate salt each containing the metal element above, an inorganic compound such as oxide and halide of the above-described metal, or a mixture thereof is preferably used.

For the reason that the polycondensation rate is increased when the catalyst is in a melted or dissolved state at the time of polycondensation, the catalyst is preferably a compound that is liquid at the time of polycondensation or dissolves in an ester low polymer or a polyester.

In addition, the polycondensation is preferably performed without a solvent, but aside from this, a small amount of a solvent may be used so as to dissolve the catalyst. The solvent for dissolving the catalyst includes alcohols such as methanol, ethanol, isopropanol and butanol, the above-described diols such as ethylene glycol, butanediol and pentanediol, ethers such as diethyl ether and tetrahydrofuran, nitriles such as acetonitrile, hydrocarbon compounds such as heptane and toluene, water, a mixture thereof, etc. This solvent is usually used such that the catalyst concentration becomes from 0.0001 to 99 mass %.

The titanium compound used as the polycondensation catalyst is preferably tetraalkyl titanate or a hydrolysate thereof and, specifically, includes tetra-n-propyl titanate, tetraisopropyl titanate, tetra-n-butyl titanate, tetra-tert-butyl titanate, tetraphenyl titanate, tetracyclohexyl titanate, tetrabenzyl titanate, a mixed titanate of these, and a hydrolysate thereof. Furthermore, titanium (oxy)acetylacetonate, titanium tetraacetylacetonate, titanium (diisopropoxide)acetylacetonate, titanium bis(ammonium lactato)dihydroxide, titanium bis(ethyl acetoacetate)diisopropoxide, titanium (triethanolaminate)isopropoxide, polyhydroxytitanium stearate, titanium lactate, titanium triethanolaminate, butyl titanate dimer, etc. are also preferably used. In addition, a liquid material obtained by mixing an alcohol, an alkaline earth metal compound, a phosphoric acid ester compound and a titanium compound is also used.

Among these, tetra-n-propyl titanate, tetraisopropyl titanate, tetra-n-butyl titanate, titanium (oxy)acetylacetonate, titanium tetraacetylacetonate, titanium bis(ammonium lactato)dihydroxide, polyhydroxytitanium stearate, titanium lactate, butyl titanate dimer, and a liquid material obtained by mixing an alcohol, an alkaline earth metal compound, a phosphoric acid ester compound and a titanium compound is preferred; tetra-n-butyl titanate, titanium (oxy)acetylacetonate, titanium tetraacetylacetonate, polyhydroxytitanium stearate, titanium lactate, butyl titanate dimer and a liquid material obtained by mixing an alcohol, an alkaline earth metal compound, a phosphoric acid ester compound and a titanium compound are more preferred; and tetra-n-butyl titanate, polyhydroxytitanium stearate, titanium (oxy)acetylacetonate, titanium tetraacetylacetonate and a liquid material obtained by mixing an alcohol, an alkaline earth metal compound, a phosphoric acid ester compound and a titanium compound are still more preferred.

The zirconium compound used as the polycondensation catalyst specifically includes, for example, zirconium tetraacetate, zirconium acetate hydroxide, zirconium tris(butoxy)stearate, zirconyl diacetate, zirconium oxalate, zirconyl oxalate, potassium zirconium oxalate, polyhydroxyzirconium stearate, zirconium ethoxide, zirconium tetra-n-propoxide, zirconium tetraisopropoxide, zirconium tetra-n-butoxide, zirconium tetra-tert-butoxide, zirconium tributoxyacetylacetonate, and a mixture thereof. Among these, zirconyl diacetate, zirconium tris(butoxy)stearate, zirconium tetraacetate, zirconium acetate hydroxide, ammonium zirconium oxalate, potassium zirconium oxalate, polyhydroxyzirconium stearate, zirconium tetra-n-propoxide, zirconium tetraisopropoxide, zirconium tetra-n-butoxide and zirconium tetra-tert-butoxide are preferred; zirconyl diacetate, zirconium tetraacetate, zirconium acetate hydroxide, zirconium tris(butoxy)stearate, ammonium zirconium oxalate, zirconium tetra-n-propoxide and zirconium tetra-n-butoxide are more preferred; and zirconium tris(butoxy)stearate is still more preferred for the reason that a colorless polyester having a high polymerization degree is easily obtained.

The germanium compound used as the polycondensation catalyst specifically includes an inorganic germanium compound such as germanium oxide and germanium chloride, and an organic germanium compound such as tetraalkoxygermanium. In view of cost and ease of availability, germanium oxide, tetraethoxygermanium and tetrabutoxygermanium are preferred, and germanium oxide is more preferred.

Other than the above-described polycondensation catalyst, a co-catalyst such as alkaline earth metal compound and acidic phosphoric acid ester compound can be used.

Specific examples of the alkaline earth metal compound include various compounds of beryllium, magnesium, calcium, strontium and barium, but in view of ease of handling or availability and catalytic effect, compounds of magnesium and calcium are preferred, and a magnesium compound excellent in the catalytic effect is more preferred. Specific examples of the magnesium compound include magnesium acetate, magnesium hydroxide, magnesium carbonate, magnesium oxide, magnesium alkoxide, and magnesium hydrogenphosphate, with magnesium acetate being preferred. One of these alkaline earth metal compounds may be used alone, or two or more thereof may be mixed and used.

As the acidic phosphoric acid ester compound, a compound having a phosphoric acid ester structure containing at least one hydroxyl group, represented by the following formulae (i) and/or (ii), is preferably used:

[Chem. 13]

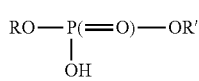

(i)

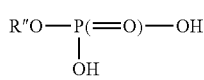

(ii)

(wherein each of R, R' and R" independently represents an alkyl group having a carbon number of 1 to 6, a cyclohexyl group, an aryl group or a 2-hydroxyethyl group; in formula (i), R and R' may be the same or different).

Specific examples of the acidic phosphoric acid ester compound include methyl acid phosphate, ethyl acid phosphate, isopropyl acid phosphate, butyl acid phosphate, and octyl acid phosphate, with ethyl acid phosphate and butyl acid phosphate being preferred. One of these acidic phosphoric acid ester compounds may be used alone, or two or more thereof may be used in combination.

Incidentally, the acidic phosphoric acid ester compound includes a diester form represented by formula (i) and a monoester form represented by formula (ii), but for the reason that a catalyst exhibiting a high catalytic activity is obtained, it is preferable to se a monoester form or a mixture of a monoester form and a diester form. The mixing mass ratio between a monoester form and a diester form is preferably 20-80:80-20, more preferably 30-70:70-30, still more preferably 40-60:60-40.

Also, the polycondensation catalyst can be produced by mixing the above-described titanium compound, alkaline earth metal compound and acidic phosphoric acid ester compound. At the time of mixing of catalyst components, a solvent is usually used. The solvent used may be sufficient if it can form a uniform solution from those titanium compound, alkaline earth metal compound and acidic phosphoric acid ester compound, but an alcohol is usually used.

That is, the polycondensation catalyst for use in the present invention is preferably produced by mixing an alcohol, a titanium compound, an alkaline earth metal compound and an acidic phosphoric acid ester compound. More preferably, the catalyst for use in the present invention is preferably produced by mixing an alcohol, a titanium compound, an alkaline earth metal compound and an acidic phosphoric acid ester compound and concentrating the mixture.

The alcohol used for the production of the polycondensation catalyst may be any alcohol as long as a uniform solution is formed when mixed with a titanium compound, an alkaline earth metal compound and an acidic phosphoric acid ester, and among others, the alcohol includes a monohydric alcohol such as methanol, ethanol, butanol, propanol and 2-ethylhexanol, and a dihydric alcohol such as ethylene glycol and 1,4-butanediol. One of these alcohols may be used alone, or two or more thereof may be used in combination. From the viewpoint of solubility of the compound and ease of handling, in the case of a monohydric alcohol, ethanol is preferred, because the solubility of the titanium compound, alkaline earth metal compound and acidic phosphoric acid ester compound is high and when concentrating the reaction solution, the solvent can be easily removed thanks to its low boiling point. On the other hand, in the case of a dihydric alcohol, 1,4BG that is the same component as the raw material diol component is preferably used, because a concentration operation is unnecessary.

As for the contents of titanium atom, alkaline earth metal atom and phosphorus atom in the polycondensation catalyst used in the present invention, assuming that the content of titanium atom is T (molar basis), the content of alkaline earth metal is M (molar basis) and the content of phosphorus atom is P (molar basis), the lower limit of T/P (molar ratio) is usually 0.1, preferably 0.3, more preferably 0.5, still more preferably 0.7, and the upper limit is usually 5.5, preferably 4.0, more preferably 3.0, still more preferably 1.5, and most preferably 1.0. When T/P is not more than the upper limit above, it is likely that the polyester produced is less colored, the catalyst stability is good, deactivation of the catalyst scarcely occurs and the risk of a deactivated catalyst being mixed in the product to impair the quality of the product is low. On the other hand, when T/P is not less than the lower limit above, the catalytic activity tends to become high.

On the other hand, the lower limit of M/P (molar ratio) is usually 0.1, preferably 0.5, more preferably 0.7, still more preferably 0.9, and the upper limit is usually 5.5, preferably 3.0, more preferably 2.0, still more preferably 1.5, yet still more preferably 1.2, and most preferably 1.1. When M/P is not more than the upper limit above, the thermal stability of the polyester obtained using this catalyst tends to become good. Also, precipitation of an alkaline earth metal scarcely occurs. On the other hand, when M/P is not less than the lower limit above, the catalytic activity is high and an increase in the terminal acid value is less likely to occur.

In the case of using such a metal compound as the polycondensation catalyst, as for the amount added of the catalyst, in terms of the metal amount relative to the polyester produced, the lower limit is usually 0.1 ppm by mass, preferably 0.5 ppm by mass, more preferably 1 ppm by mass, still more preferably 5 ppm by mass, yet still more preferably 10 ppm by mass, and the upper limit is usually 10,000 ppm by mass, preferably 1,000 ppm by mass, more preferably 500 ppm by mass, still more preferably 200 ppm by mass, yet still more preferably 150 ppm by mass. If the amount of the catalyst used is too large, not only this is economically disadvantageous but also the terminal acid value at the time of polymer withdrawal greatly rises, as a result, the thermal stability or hydrolysis resistance of the polyester tends to decrease. Conversely, if the amount added is too small, thermal decomposition of the polyester is induced during the production, and a polyester exhibiting practically useful physical properties can be hardly obtained.

Above all, as for the content of titanium atom contained in the polyester obtained by the present invention, in terms of titanium atom, the lower limit is usually 0.1 ppm by mass, preferably 0.5 ppm by mass, more preferably 1 ppm by mass, still more preferably 5 ppm by mass, yet still more preferably 10 ppm by mass, and the upper limit is usually 10,000 ppm by mass, preferably 1,000 ppm by mass, more preferably 500 ppm by mass, still more preferably 200 ppm by mass, yet still more preferably 150 ppm by mass. If the titanium atom content exceeds the upper limit above, rise of the terminal acid value and coloring of the polyester tend to occur. On the other hand, if the content is less than the lower limit, it is likely that the polycondensation rate is low and a polyester having high viscosity can be hardly obtained.

The timing of addition of the polycondensation catalyst to the reaction system is not particularly limited as long as it is before the polycondensation reaction step. The catalyst may be added at the time of charging of raw materials, but when the catalyst is present together in the situation that unreacted dicarboxylic acid or water is present in a large amount or is generated, the catalyst may be deactivated, giving rise to precipitation of foreign matters, and the quality of the product may be impaired. Therefore, the catalyst is preferably added after the esterification reaction step.

Incidentally, in the production of an aliphatic polyester, when a small amount of a trifunctional or higher functional oxycarboxylic acid, a trifunctional or higher functional alcohol, a trifunctional or higher functional carboxylic acid, etc. is added to the raw material together with an aliphatic dicarboxylic acid component and a diol component, a polyester having high viscosity is easily obtained. Among these trifunctional or higher polyfunctional compounds, an oxycarboxylic acid such as malic acid, citric acid and fumaric acid is preferably used, and malic acid is more preferably used. In the case of using a trifunctional or higher polyfunctional compound, the upper limit of the amount used thereof is, relative to all dicarboxylic acid components, preferably 5 mol %, more preferably 0.5 mol %, and the lower limit is preferably 0.001 mol %, more preferably 0.05 mol %. If the amount used exceeds the upper limit in this range, a gel (unmelted product) is readily produced, and if the amount used is less than the lower limit, the effect of increasing the viscosity can be hardly obtained.

The reduced viscosity ($\eta sp/c$) value of the polyester produced in the present invention can be controlled by the polycondensation time, polycondensation temperature, polycondensation pressure, etc. For the reason that a polyester having practically sufficient mechanical properties is obtained, the lower limit of the reduced viscosity is usually 1.6 dL/g, preferably 1.7 dL/g, more preferably 1.8 dL/g, still more preferably 2.0 dL/g. Also, in view of, for example, ease of withdrawing after the polycondensation reaction of polyester and ease of molding, the upper limit is usually 6.0 dL/g, preferably 5.0 dL/g, more preferably 4.0 dL/g.

Here, the reduced viscosity of the polyester is measured by the method described in Examples later.

The polyester obtained in the present invention is characterized by having good color tone. The YI value as an indicator of color tone can be controlled by the polycondensation temperature, catalyst amount, etc. and is preferably 30 or less, more preferably 25 or less, still more preferably 20 or less. If the YI value exceeds the upper limit above, a molded article formed may disadvantageously take on a yellow tinge.

Here, the YI value of the polyester is measured by the method described in Examples later.

As for the indicator of color tone of the polyester of the present invention, a value expressed by the color tone b value can also be used. The upper limit thereof is, usually, preferably 13.5, more preferably 11, still more preferably 9, yet still more preferably 3. On the other hand, the lower limit thereof is not particularly limited but is, usually, preferably −2, more preferably −1.5, still more preferably −0.8.

Incidentally, in the polyester at an arbitrary stage of the polyester production process or in the obtained polyester, various additives such as thermal stabilizer, antioxidant, nucleating agent, flame retardant, antistatic agent, release agent and ultraviolet absorber may be added as long as the characteristics of the polyester are not impaired.

In addition, at the time of molding of the polyester, the molding may also be performed by adding a reinforcement or an extender, such as glass fiber, carbon fiber, titanium whisker, mica, talc, $CaCO_3$, $TiO_2$ and silica, other than various additives above.

Various additives and other components which can be added to the polyester, and the method for molding the polyester are the same as those described later in <PBT Composition> and <Molding Process of PBT>.

<Production of PBT>

The production method of PBT that is particularly preferred as the polyester produced by the production method of a polyester of the present invention, is described below.

<Raw Material for PBT Production>

PBT in the present invention is obtained by subjecting a terephthalic acid or a terephthalic acid alkylate and 1,4BG to an esterification reaction or a transesterification reaction and then to a polycondensation reaction.

The terephthalic acid or terephthalic acid alkylate may be a compound produced by the conventional fossilization process or a biomass-resource-derived compound obtained by a fermentation process. Incidentally, the alkyl group of the terephthalic acid alkylate is preferably an alkyl group having a carbon number of 1 to 4.

The terephthalic acid or terephthalic acid alkylate used as a raw material preferably accounts for 80 mol % or more, more preferably 90 mol % or more, and most preferably 100 mol %, of all dicarboxylic acid components. Also, the biomass-resource-derived 1,4BG preferably accounts for 80 mol % or more, more preferably 90 mol % or more, still more preferably 99 mol % or more, of all diol components.

If the ratio of the terephthalic acid or terephthalic acid alkylate in all dicarboxylic acid components and the ratio of the biomass-resource-derived 1,4BG in all diol components are not less than the lower limits above, the molded article tends to be improved in the mechanical strength, heat resistance, aroma retentivity, etc., in terms of crystallization at the time of molding into an electric parts, etc. and orientation crystallization of molecular chains by stretching at the time of molding into a film, a fiber, etc.

The raw material dicarboxylic acid component may contain a dicarboxylic acid component other than the terephthalic acid or terephthalic acid alkylate as the main component, and the other dicarboxylic acid component may be fed to a reaction vessel together with the terephthalic acid or terephthalic acid alkylate. The other dicarboxylic acid component includes, for example, an aromatic dicarboxylic acid and an ester-forming derivative thereof, such as phthalic acid, isophthalic acid, dibromoisophthalic acid, sodium sulfoisophthalate, phenylenedioxydicarboxylic acid, 4,4'-diphenyldicarboxylic acid, 4,4'-diphenyl ether dicarboxylic acid, 4,4'-diphenyl ketone dicarboxylic acid, 4,4'-diphenoxyethanedicarboxylic acid, 4,4'-diphenyl sulfone dicarboxylic acid and 2,6-naphthalenedicarboxylic acid; an alicyclic dicarboxylic acid and an ester-forming derivative thereof, such as hexahydroterephthalic acid and hexahydroisophthalic acid; and an aliphatic chain dicarboxylic acid and an ester-forming derivative thereof, such as succinic acid, glutaric acid, adipic acid, pimelic acid, suberic acid, azelaic acid, sebacic acid, undecadicarboxylic acid and dodecadicarboxylic acid. One of these dicarboxylic acids may be used alone, or two or more thereof may be mixed and used.

On the other hand, the raw material diol component may contain a diol component other than the biomass-resource-derived 1,4BG. The other diol component includes, for example, an aliphatic chain diol such as ethylene glycol, trimethylene glycol, pentamethylene glycol, hexamethylene glycol, octamethylene glycol, decamethylene glycol, neopentyl glycol, 2-methyl-1,3-propanediol, 1,2-butanediol, 1,3-butanediol, 2,3-butanediol, 1,3-pentanediol, 2,3-pentanediol, 2-ethyl-2-butyl-1,3-propanediol, polyethylene glycol and polytetramethylene glycol; an alicyclic diol such as 1,2-cyclohexanediol, 1,4-cyclohexanediol, 1,1-cyclohexanedimethylol, 1,4-cyclohexanedimethylol and 2,5-norbornanedimethylol; an aromatic diol such as xylylene glycol, 4,4'-dihydroxybiphenyl, 2,2-bis(4'-hydroxyphenyl)propane, 2,2-bis(4'-β-hydroxyethoxyphenyl)propane, bis(4-hydroxyphenyl)sulfone and bis(4'-β-hydroxyethoxyphenyl) sulfonic acid; an ethylene oxide or propylene oxide adduct of 2,2-bis(4'-hydroxyphenyl)propane; and 1,4BG not derived from biomass resources. One of these diols may be used alone, or two or more thereof may be mixed and used.

As the PBT feedstock, the following component may be further used as a copolymerization component, other than the above-described dicarboxylic acid component and diol component.

The copolymerization component includes, for example, a monofunctional component, e.g., a hydroxycarboxylic acid such as glycolic acid, p-hydroxybenzoic acid and p-β-hydroxyethoxybenzoic acid, an alkoxycarboxylic acid, a stearyl alcohol, heneicosanol, octacosanol, a benzyl alcohol, a stearic acid, a behenic acid, a benzoic acid, a tert-butylbenzoic acid, and a benzoylbenzoic acid; and a trifunctional or higher polyfunctional component such as tricarballylic acid, trimellitic acid, trimesic acid, pyromellitic acid, naphthalene-tetracarboxylic acid, gallic acid, trimethylolethane, trimethylolpropane, glycerol, pentaerythritol and sugar ester. One of these copolymerization components may be used alone, or two or more thereof may be mixed and used.

<Production Method of PBT>

The production method of PBT of the present invention may be sufficient if PBT can be produced, and is not particularly limited.

Known production methods of PBT are roughly classified into a so-called direct polymerization method using a terephthalic acid as the main raw material and a transesterification method using a terephthalic acid alkylate as the main raw material. These are different in that water is produced by the initial esterification reaction in the former and an alcohol is produced by the initial transesterification reaction in the latter, but in view of stability of raw material availability, ease of treatment of the distillate, high unit consumption of the raw material and effect of improvement by the present invention, a direct polymerization method is preferred.

The direct polymerization method includes, for example, a method where dicarboxylic acid components containing a terephthalic acid and diol components containing 1,4BG are continuously subjected to an esterification reaction in the presence of an esterification reaction catalyst in a single-stage or multistage esterification reaction tank under the conditions that the temperature is usually 180° C. or more, preferably 200° C. or more, more preferably 210° C. or more, and is usually 260° C. or less, preferably 250° C. or less, more preferably 245° C. or less, the pressure is usually 10 kPa or more, preferably 13 kPa or more, more preferably 50 kPa or more, and is usually 133 kPa or less, preferably 120 kPa or less, more preferably 110 kPa or less, and the reaction time is usually 0.5 hours or more, preferably 1 hour or more, and is usually 5 hours or less, preferably 3 hours or less, the obtained oligomer as an esterification reaction product is transferred to a polycondensation reaction tank, and its polycondensation reaction is continuously performed with stirring in the presence of a polycondensation reaction catalyst in a multistage polycondensation reaction tank at a temperature of usually 210° C. or more, preferably 220° C. or more, and usually 260° C. or less, preferably 250° C. or less, more preferably 245° C. or less, under reduced pressure at a pressure of usually 27 kPa or less, preferably 20 kPa or less, more preferably 13 kPa or less, and in at least one polycondensation reaction tank, still more preferably 2 kPa or less, for usually from 2 to 12 hours, preferably from 2 to 10 hours.

The transesterification method includes, for example, a method where dicarboxylic acid components containing a terephthalic acid alkylate such as dimethyl terephthalate and diol components containing 1,4BG are continuously subjected to a transesterification reaction in the presence of a transesterification reaction catalyst in a single-stage or multistage esterification reaction tank under the conditions that the temperature is usually 110° C. or more, preferably 140° C. or more, more preferably 180° C. or more, and is usually 260° C. or less, preferably 245° C. or less, more preferably 220° C. or less, the pressure is usually 10 kPa or more, preferably 13 kPa or more, more preferably 60 kPa or more, and is usually 133 kPa or less, preferably 120 kPa or less, more preferably 110 kPa or less, and the reaction time is usually 0.5 hours or more, preferably 1 hour or more, and is usually 5 hours or less, preferably 3 hours or less, the obtained oligomer as a transesterification reaction product is transferred to a polycondensation reaction tank, and its polycondensation reaction is continuously performed with stirring in the presence of a polycondensation reaction catalyst in a multistage polycondensation reaction tank at a temperature of usually 210° C. or more, preferably 220° C. or more, and usually 260° C. or less, preferably 250° C. or less, more preferably 245° C. or less, under reduced pressure at a pressure of usually 27 kPa or less, preferably 20 kPa or less, more preferably 13 kPa or less, and in at least one polycondensation reaction tank, still more preferably 2 kPa or less, for usually from 2 to 12 hours, preferably from 2 to 10 hours.

The esterification reaction or transesterification reaction catalyst includes, for example, an antimony compound such as antimony trioxide; a germanium compound such as germanium dioxide and germanium tetroxide; a titanium compound, e.g., a titanium alcoholate such as tetramethyl titanate, tetraisopropyl titanate and tetrabutyl titanate, and a titanium phenolate such as tetraphenyl titanate; a tin compound such as dibutyltin oxide, methylphenyltin oxide, tetraethyltin, hexaethylditin oxide, cyclohexahexyldititin oxide, didodecyltin oxide, triethyltin hydroxide, triphenyltin hydroxide, triisobutyltin acetate, dibutyltin diacetate, diphenyltin dilaurate, monobutyltin trichloride, tributyltin chloride, dibutyltin sulfide, butylhydroxytin oxide, methylstannoic acid, ethylstannoic acid and butylstannoic acid; an alkaline earth metal compound, e.g., a magnesium compound such as magnesium acetate, magnesium hydroxide, magnesium carbonate, magnesium oxide, magnesium alkoxide and magnesium hydrogenphosphate, and a calcium compound such as calcium acetate, calcium hydroxide, calcium carbonate, calcium oxide, calcium alkoxide and calcium hydrogenphosphate; a manganese compound; and a zinc compound. One of these compounds may be used alone, or two or more thereof may be mixed and used. Among others, a titanium compound and a tin compound are preferred, and tetrabutyl titanate is more preferred.

The amount use of the esterification reaction or transesterification reaction catalyst is not particularly limited but is, in terms of metal concentration (mass) in PBT, usually 1 ppm or more, preferably 5 ppm or more, more preferably 10 ppm or more, still more preferably 20 ppm or more, most preferably 30 ppm or more, and is usually 300 ppm or less, preferably 200 ppm or less, more preferably 150 ppm or less, still more preferably 100 ppm or less, yet still more preferably 90 ppm or less, most preferably 60 ppm or less. When the metal concentration (mass) in PBT is not more than the upper limit above, the catalyst is less likely to cause generation of foreign matters and moreover, a deterioration reaction or gas evolution tends to be hardly brought about at the time of thermal residence of PBT, and when the metal concentration is not less than the lower limit, the main reaction rate is high and a side reaction is difficult to occur.

Also, as the polycondensation reaction catalyst, the esterification reaction or transesterification reaction catalyst may be used directly as the polycondensation reaction catalyst, or the catalyst above may be further added. The amount used of the polycondensation reaction is not particularly limited but for the same reason as the esterification reaction or transesterification reaction catalyst, the amount is, in terms of metal concentration (mass) in PBT, usually 0.5 ppm or more, preferably 1 ppm or more, more preferably 3 ppm or more, still more preferably 5 ppm or more, most preferably 10 ppm or more, and is usually 300 ppm or less, preferably 200 ppm or less, more preferably 100 ppm or less, still more preferably 50 ppm or less, most preferably 30 ppm or less.

In the case of using an organic titanium compound as the catalyst, from the standpoint of suppressing generation of foreign matters, the final titanium metal concentration (mass) in PBT is preferably 250 ppm or less, more preferably 100 ppm or less, still more preferably 60 ppm or less, and most preferably 50 ppm or less.

The metal concentration (mass) in PBT can be measured using atomic emission, Induced Coupled Plasma (ICP) method, etc. after recovering the metal in PBT by wet ashing or other methods.

In the esterification reaction, transesterification reaction and polycondensation reaction, in addition to the above-described catalyst, there may be used a phosphorus compound such as orthophosphoric acid, phosphorous acid, hypophosphorous acid, polyphosphoric acid and an ester or a metal salt thereof; a reaction aid, for example, an alkali metal compound, e.g., a sodium compound such as sodium hydroxide and sodium benzoate, lithium acetate, and a potassium compound such as potassium hydroxide and potassium acetate; a reaction aid, e.g., an alkaline earth metal compound such as magnesium acetate and calcium acetate; a phenol compound such as 2,6-di-tert-butyl-4-octyl phenol and pentaerythrityl-tetrakis[3-(3',5'-tert-butyl-4'-hydroxyphenyl)propionate]; a thioether compound such as dilauryl-3,3'-thiodipropionate and pentaerythrityl-tetrakis(3- laurylthiodipropionate); an antioxidant, e.g., a phosphorus compound such as triphenyl phosphite, tris(nonylphenyl)phosphite and tris(2,4-di-tert-butylphenyl)phosphite; paraffin wax, microcrystalline wax, polyethylene wax, and a long-chain fatty acid and an ester thereof, typified by montanic acid and montanic acid ester; a release agent such as silicone oil; and the like.

The polycondensation reaction tank includes known reaction tanks such as vertical stirring polymerization tank, horizontal stirring polymerization tank and thin film evaporation polymerization tank. In the latter stage of polycondensation, where the viscosity of the reaction solution rises, the mass transfer tends to be a factor governing the increase of molecular weight rather than the reaction rate. Therefore, it is advantageous for achieving the object of the present invention to drive the main reaction while suppressing a side reaction, lower the temperature as much as possible and raise the surface renewal property, and it is preferable to select a single or a plurality of horizontal stirring polymerization tanks having a thin film evaporation function and being excellent in the surface renewal property, plug flow property and self-cleaning property.

Also, PBT obtained by the production method of the present invention may be subsequently subjected to solid-phase polycondensation by a known method to increase the molecular weight.

PBT obtained by the polycondensation reaction is usually transferred to a polymer extraction die from the bottom of the polycondensation reaction tank, withdrawn in a strand form and, with water cooling or after water cooling, cut by a cutter into a pellet-like or chip-like granular material. The granular material may be subsequently subjected to solid-phase polycondensation by a known method, etc. to raise its intrinsic viscosity.

<Physical Properties of PBT>

The intrinsic viscosity of PBT produced by the present invention (hereinafter, sometimes referred to as "PBT of the present invention") is not particularly limited but in view of mechanical properties, pelletization stability and moldability, is preferably 0.50 dL/g or more, more preferably 0.70 dL/g or more, and is preferably 1.50 dL/g or less, more preferably 1.35 dL/g or less. There is a tendency that an intrinsic viscosity of PBT which is not less than the lower limit above is preferred in the light of mechanical properties of the molded article and an intrinsic viscosity not more than the upper limit above is be preferred in the light of moldability.

The terminal carboxyl group concentration of PBT of the present invention is not particularly limited, but the lower limit is preferably 1 equivalent/ton, more preferably 2 equivalents/ton, still more preferably 3 equivalents/ton, and most preferably 5 equivalents/ton, and the upper limit is preferably 50 equivalents/ton, more preferably 40 equivalents/ton, still more preferably 30 equivalents/ton, and most preferably 25 equivalents/ton. When the terminal carboxyl group concentration of PBT is more than the upper limit above, PBT is likely to have good hydrolysis resistance, and when the concentration is not less than the lower limit above, the polycondensation property tends to be good.

The terminal carboxyl group concentration of PBT can be determined by dissolving the resin in an organic solvent and titrating the solution with an alkali solution such as sodium hydroxide. More specifically, the concentration is determined by the method described in Examples later.

The terminal vinyl group concentration of PBT of the present invention is not particularly limited but in view of color tone and polycondensation property, is preferably 15 equivalents/ton or less, more preferably 10 equivalents/ton or less, still more preferably 7 equivalents/ton or less.

The terminal vinyl group concentration of PBT can be determined by dissolving PBT in a solvent and measuring NMR. More specifically, the concentration is determined by the method described in Examples later.

<Color Tone of PBT>

Usually, the color tone of PBT produced using raw material 1,4BG derived from biomass resources tends to deteriorate, but the color tone of PBT of the present invention is good. In addition, as described above, the color tone of the obtained PBT can be adjusted by controlling the content of a cyclic carbonyl compound having a carbon atom number of 5 or 6 in the raw material 1,4BG in the refining step of 1,4BG.

<PBT Composition>

PBT of the present invention can be formed as a PBT composition containing components other than PBT as long as the effects of the present invention are not seriously impaired. Specific examples of the component other than PBT include various resins such as thermoplastic resin and thermosetting resin, a release agent, a filler such as reinforcing filler, a flame retardant, and other various additives.

The thermoplastic resin includes polyethylene, polypropylene, polystyrene, polyacrylonitrile, a polymethacrylic acid ester, a polyacrylic acid ester, ABS resin, a polycarbonate, a polyamide, a polyphenylene sulfide, polyethylene terephthalate, a liquid crystal polyester, polyacetal, polyphenylene oxide, etc. The thermosetting resin includes a phenol resin, a melamine resin, a silicone resin, an epoxy resin, etc.

Only one of these resins may be used, or two or more thereof may be used in combination. Out of these resins, a thermoplastic resin is used in many cases.

In the case of blending such a resin, the blending amount (mass) thereof may be sufficient if the excellent effects of the present invention are brought out, and the blending amount is not particularly limited but is such an amount that the ratio of PBT to the total amount of resins becomes usually 0.1 mass % or more, preferably 1 mass % or more, more preferably 10 mass % or more, and usually 99.9 mass % or less, preferably 99 mass % or less, more preferably 90 mass % or less.

The release agent is not particularly limited but includes, for example, a phenol compound such as 2,6-di-tert-butyl-4-octyl phenol and pentaerythrityl-tetrakis[3-(3',5'-tert-butyl-4'-hydroxyphenyl)propionate]; a thioether compound such as dilauryl-3,3'-thiodipropionate and pentaerythrityl-tetrakis(3-laurylthiodipropionate); an antioxidant, e.g., a phosphorus compound such as triphenyl phosphite, tris (nonylphenyl)phosphite and tris(2,4-di-tert-butylphenyl) phosphite; paraffin wax, microcrystalline wax, polyethylene wax, and a long-chain fatty acid and an ester thereof, typified by montanic acid and montanic acid ester; and silicone oil. One of these may be used alone, or two or more thereof may be mixed and used.

The reinforcing filler is not particularly limited but includes, for example, an inorganic fiber such as glass fiber, carbon fiber, silica.alumina fiber, zirconia fiber, boron fiber, boron nitride fiber, silicon nitride potassium titanate fiber and metal fiber; and an organic fiber such as aromatic polyamide fiber and fluororesin fiber. Among these, an inorganic fiber, particularly, glass fiber, is suitably used. Only one of these reinforcing fillers may be used, or two or more thereof may be mixed and used.

In the case where the reinforcing filler is an inorganic or organic fiber, the average fiber diameter is not particularly limited but is usually from 1 to 100 preferably from 2 to 50

μm, more preferably from 3 to 30 μm, still more preferably from 5 to 20 μm. The average fiber length is not particularly limited but is usually from 0.1 to 20 mm, preferably from 1 to 10 mm.

As the reinforcing agent, a filler surface-treated with a sizing agent or a surface treatment agent so as to enhance the interference adherence to PBT is preferably used. The sizing agent or surface treatment agent includes, for example, a functional compound such as epoxy-based compound, acrylic compound, isocyanate-based compound, silane-based compound and titanate-based compound. The treatment with a sizing agent or a surface treatment agent may be performed by previously surface-treating the reinforcing filler, or the filler may be put into contact with a sizing agent or a surface treatment agent when preparing the PBT composition.

In the case of using a reinforcing filler, the blending amount thereof is usually 150 parts by mass or less, preferably from 5 to 100 parts by mass, per 100 parts by mass of resin components including PBT.

In PBT of the present invention, a filler other than a reinforcing filler may be blended. This filler includes, for example, a plate-shaped inorganic filler, a ceramic bead, asbestos, wollastonite, talc, clay, mica, zeolite, kaolin, potassium titanate, barium sulfate, titanium oxide, silicon oxide, aluminum oxide, magnesium hydroxide, etc. By blending a plate-shaped inorganic filler, anisotropy and warping of the molded article can be reduced. The plate-shaped inorganic filler includes a glass flake, mica, a metal foil, etc. Among these fillers, a glass flake is suitably used.

In PBT of the present invention, a flame retardant may also be blended so as to impart flame retardancy. The flame retardant is not particularly limited and includes, for example, an organic halogen compound, an antimony compound, a phosphorus compound, and other organic and inorganic flame retardants. The organic halogen compound includes, for example, a brominated polycarbonate, a brominated epoxy resin, a brominated phenoxy resin, a brominated polyphenylene ether resin, a brominated polystyrene resin, a brominated bisphenol A, and polypentabromobenzyl acrylate. The antimony compound includes, for example, antimony trioxide, antimony pentoxide, and sodium antimonate. The phosphorus compound includes a phosphoric acid ester, a polyphosphoric acid, ammonium polyphosphate, and red phosphorus. The other organic flame retardant includes, for example, a nitrogen compound such as melamine and cyanuric acid. The other inorganic flame retardant includes, for example, aluminum hydroxide, magnesium hydroxide, a silicon compound, and a boron compound. One of these flame retardants may be used alone, or two or more thereof may be mixed and used.

Other various additives are not particularly limited but include, for example, a stabilizer such as antioxidant and heat stabilizer, a lubricant, a catalyst deactivator, a nucleating agent, and a crystallization accelerator. These additives may be added in the course of polycondensation or after polycondensation.

In addition, other various additives also include a stabilizer such as ultraviolet absorber and weather-resistant stabilizer, a colorant such as dye and pigment, an antistatic agent, a blowing agent, a plasticizer, and an impact resistant improver.

The method for blending the above-described other component is not particularly limited but is preferably, for example, a method using, as a kneader, a single- or twin-screw extruder having equipment allowing for volatilization or escape through a vent port. Respective components including additive components may be fed en bloc to the kneader or may be fed sequentially. Also, two or more components selected from respective components including additive components may be previously mixed.

<Molding Process of PBT>

The method for molding PBT of the present invention or a PBT composition containing the polymer is not particularly limited, and a molding method, etc. generally used for a thermoplastic resin, specifically, such as injection molding, hollow molding, extrusion molding and press molding, may be applied.

PBT of the present invention and the PBT composition containing the polymer are excellent in the color tone, thermal stability, transparency and quality stability and can be suitably used in the applications to an injection molded article such as electric or electronic component and automotive component, and an extrusion molded article such as film, monofilament and fiber.

[Production of Polyester Polyol]

The production method of a polyester polyol that is suitably used as a raw material for the production of the polyurethane of the present invention (hereinafter, sometimes referred to as "polyester polyol of the present invention"), is described below.

This polyester polyol is produced by subjecting a dicarboxylic acid and/or a derivative thereof (hereinafter, sometimes referred to as "dicarboxylic acid component") and a diol compound to an esterification and/or transesterification reaction.

In the production method of the polyester polyol of the present invention, a biomass-resource-derived diol having a content of a cyclic carbonyl compound with a carbon atom number of 5 or 6 of 0.01 to 100 ppm by mass, which is described above in the paragraph of Raw Material for Production of Polyester of the present invention, is used as the diol compound.

(1) Dicarboxylic Acid Component

The dicarboxylic acid component for use in the present invention includes, for example, an aliphatic dicarboxylic acid, an aliphatic dicarboxylic acid derivative, an aromatic dicarboxylic acid, and an aromatic dicarboxylic acid derivative. One of these may be used alone, or two or more thereof may be mixed and used. Among these, in the application requiring weather resistance, such as synthetic or artificial leather and coating material, the main component is preferably an aliphatic dicarboxylic acid and/or a derivative thereof, because yellowing hardly occurs. On the other hand, in the application requiring strength, such as elastic fiber, the main component is preferably an aromatic dicarboxylic acid with high cohesive force and/or a derivative thereof.

With respect to the "main component" as used herein, the content of the component is, usually, preferably 50 mol % or more, more preferably 60 mol % or more, still more preferably 70 mol % or more, yet still more preferably 90 mol % or more, based on all dicarboxylic acid components.

The aromatic dicarboxylic acid includes, for example, a terephthalic acid and an isophthalic acid. The aromatic dicarboxylic acid derivative includes, for example, a lower alkyl ester of the aromatic dicarboxylic acid above. The lower alkyl ester of an aromatic dicarboxylic acid specifically includes, for example, a methyl ester, an ethyl ester, a propyl ester, and a butyl ester.

Among these, a terephthalic acid and an isophthalic acid are preferred as the aromatic dicarboxylic acid. Also, dimethyl terephthalate and dimethyl isophthalate are preferred as the aromatic dicarboxylic acid derivative. For example, as in a polyester of dimethyl terephthalate and 1,4-butanediol, a desired aromatic polyester polyol polyurethane can be produced by using an arbitrary aromatic dicarboxylic acid.

The aliphatic dicarboxylic acid is, usually, preferably a chain or alicyclic dicarboxylic acid having a carbon number of 2 to 40.

The chain or alicyclic dicarboxylic acid having a carbon number of 2 to 40 specifically includes, for example, an oxalic acid, a succinic acid, a glutaric acid, an adipic acid, a sebacic acid, a dodecane diacid, a dimer acid, and a cyclohexanedicarboxylic acid. Among these, in view of physical properties of the obtained polyurethane, an adipic acid, a succinic acid, a sebacic acid and a mixture thereof are preferred, and a dicarboxylic acid containing a succinic acid as the main component is more preferred.

The aliphatic dicarboxylic acid derivative includes, for example, a lower alkyl ester of the aliphatic dicarboxylic acid above, such as methyl ester, ethyl ester, propyl ester and butyl ester, and a cyclic acid anhydride of the aliphatic dicarboxylic acid above, such as succinic acid. Among these, methyl esters of an adipic acid and a succinic acid, and a mixture thereof are preferred as the aliphatic dicarboxylic acid derivative.

The dicarboxylic acid component for use in the present invention may contain a biomass-resource-derived component. Preferable biomass-resource-derived components contained in the dicarboxylic acid component include, for example, an adipic acid, a succinic acid, and a sebacic acid, with a succinic acid being more preferred.

In the present invention, the embodiment where the dicarboxylic acid contains a biomass-resource-derived component may be, in the case of a single kind of a dicarboxylic acid component, a mixture of, for example, a succinic acid that is a petroleum-derived raw material, and, for example, a biomass-resource-derived succinic acid, and in the case of a mixture of two or more kinds of dicarboxylic acids, may be sufficient if at least one kind of a dicarboxylic acid component is derived from biomass resources, that is, may be a mixture of a biomass-resource-derived dicarboxylic acid component and a dicarboxylic acid component that is a petroleum-derived raw material. In the case of a mixture of a biomass-resource-derived dicarboxylic acid component and a dicarboxylic acid component that is a petroleum-derived raw material, the content of the biomass-resource-derived dicarboxylic acid component in the mixture is preferably 20 mol % or more, more preferably 40 mol % or more, still more preferably 60 mol % or more, yet still more preferably from 90 to 100 mol %.

The dicarboxylic acid component for use in the present invention is, usually, preferably a dicarboxylic acid with less coloring. As for the yellow index (YI value) of the dicarboxylic acid component for use in the present invention, the upper limit is, usually, preferably 50, more preferably 20, still more preferably 10, yet still more preferably 6, and even yet still more preferably 4. On the other hand, the lower limit is not particularly limited but is, usually, preferably −20, more preferably −10, still more preferably −5, yet still more preferably −3, and most preferably −1.

Coloring of the obtained polyurethane can be suppressed by using a dicarboxylic acid component having a YI value of 50 or less. On the other hand, use of a dicarboxylic acid component having a YI value of −20 or more is economically advantageous in that, for example, an extremely expensive equipment investment is not required for the production or a vast amount of production time is not necessary. Incidentally, the YI value as used in the description of the present invention is a value measured by the method based on JIS-K7105.

(2) Diol Compound

In general, the diol compound for use in the production of a polyester polyol includes an aromatic diol compound and an aliphatic diol compound each having two hydroxyl groups, and one of these compounds may be used alone, or two or more thereof may be mixed and used.

Out of these diol compounds, in view of ease of handling of the obtained polyester polyol and balance of physical properties, an aliphatic diol compound, that is, a linear or branched, chain or alicyclic diol compound, is preferred, and the compound includes those where the lower limit of the carbon number is preferably 2 and the upper limit is preferably 10, more preferably 6.

Specific examples of the aliphatic diol compound include ethylene glycol, 1,3-propanediol, 2-methyl-1,3-propanediol, neopentyl glycol, 1,5-pentanediol, 3-methyl-1,5-pentanediol, 1,2-butanediol, 1,6-hexanediol, decamethylene glycol, 1,9-nonanediol, 1,4-butanediol, and 1,4-cyclohexanedimethanol.

Among these, ethylene glycol, 1,4-butanediol, 1,3-propanediol, 2-methyl-1,3-propanediol and 3-methyl-1,5-pentanediol are preferred; ethylene glycol, 1,4-butanediol and a mixture thereof are more preferred; and a compound containing 1,4-butanediol as the main component, and 1,4-butanediol are still more preferred.

The "main component" as used herein indicates that the content of the component is, usually, preferably 50 mol % or more, more preferably 60 mol % or more, still more preferably 70 mol % or more, yet still more preferably 90 mol % or more, based on all diol compounds.

When a diol compound having an even number of methylene chains between hydroxyl groups and an even carbon number is used as the aliphatic diol compound, the mechanical strength of the polyurethane produced using the obtained polyester polyol is increased, and when a diol compound having an odd carbon number or a branched structure is used, the handleability of the obtained polyester polyol is enhanced.

The aromatic diol compound is not particularly limited as long as it is an aromatic diol compound having two hydroxyl groups, but the aromatic diol compound includes a compound where the lower limit value of the carbon number is preferably 6 and the upper limit value is preferably 15.

Specific examples of the aromatic diol compound include hydroquinone, 1,5-dihydroxynaphthalene, 4,4'-dihydroxydiphenyl, bis(p-hydroxyphenyl)methane, and bis(p-hydroxyphenyl)-2,2-propane.

In the present invention, the content of the aromatic diol compound in all diol compounds used for the production of a polyester polyol is, usually, preferably 30 mol % or less, more preferably 20 mol % or less, still more preferably 10 mol % or less.

In addition, a both end hydroxy-terminated polyether may also be used as the diol component. The lower limit value of the carbon number of the both end hydroxy-terminated polyether is, usually, preferably 4, more preferably 10, and the upper limit value is, usually, preferably 1,000, more preferably 200, still more preferably 100.

Specific examples of the both end hydroxy-terminated polyether include diethylene glycol, triethylene glycol, polyethylene glycol, polypropylene glycol, polytetramethylene glycol, poly-1,3-propanediol, and poly-1,6-hexamethylene glycol. In addition, for example, a copolymerized polyether of polyethylene glycol and polypropylene glycol may also be used.

The amount used of the both end hydroxy-terminated polyether is usually, in terms of the content of the both end hydroxy-terminated polyether-derived constitutional unit in the obtained polyester polyol, preferably 90 mass % or less, more preferably 50 mass % or less, still more preferably 30 mass % or less.

In the present invention, a biomass-resource-derived diol compound is used as the diol compound. The biomass-resource-derived diol compound for use in the present invention is produced directly from a carbon source such as glucose by a fermentation process.

As a result of intensive studies, the present inventors have found that cyclic carbonyl compounds having a carbon atom number of 5 or 6 represented by formulae (I), (II) and (III), contained in the biomass-resource-derived diol, have a significant effect on the deterioration of color tone of the obtained polyester polyol when producing a polyester polyol by using the diol, among others, when producing polybutylene adipate.

The content of the cyclic carbonyl compound having a carbon atom number of 5 or 6 in the biomass-resource-derived diol working out to a raw material of the polyester polyol in the present invention is, in terms of mass ratio to the diol, usually 100 ppm or less, preferably 50 ppm or less, more preferably 12 ppm or less, still more preferably 3 ppm or less. When the content of the cyclic carbonyl compound having a carbon atom number of 5 or 6 in the biomass-resource-derived diol, particularly, in 1,4BG is not more than the upper limit above, the color tone in the production of a polyester polyol, among others, the color tone in the production of polybutylene adipate, tends to become good. Incidentally, in the present invention, the color tone of the obtained polyester polyol can also be adjusted by controlling the content of the cyclic carbonyl compound having a carbon atom number of 5 or 6 in the raw material diol within the range above.

The reason why the content of the cyclic carbonyl compound having a carbon atom number of 5 or 6 in the biomass-resource-derived diol used as a raw material for the production of a polyester polyol, which is not more than the upper limit above, is preferred in view of color tone of the obtained polyester polyol, is not clearly known but is presumed because the production volume of various derivatives rich in reactivity, such as amide, amine and amino acid, produced by a reaction of the cyclic carbonyl compound considered to cause deterioration of the color tone of the polyester polyol with a nitrogen atom-containing compound, as described above, can be reduced.

Among others, the compound having a structure represented by formula (III) significantly deteriorates the color tone of the polyester polyol and therefore, the upper limit of the content of the compound having a structure represented by formula (III) in the diol feedstock for use in the present invention is, in terms of the mass ratio to the diol, usually 50 ppm, preferably 12 ppm, more preferably 6 ppm, still more preferably 2 ppm. When the content of the compound having a structure represented by formula (III) in the biomass-resource-derived diol, particularly, in 1,4BG, is not more than the upper limit above, the color tone in the production of a polyester polyol, particularly, in the production of polybutylene adipate, tends to become good. On the other hand, when the content is not less than the lower limit above, the refining step of the biomass-resource-derived diol becomes simple and easy, and this is economically advantageous.

Incidentally, in the present invention, the content of the cyclic carbonyl compound having a carbon atom number of 5 or 6 in the biomass-resource-derived diol indicates the total content of a cyclic carbonyl compound having a carbon atom number of 5 and a cyclic carbonyl compound having a carbon atom number of 6, and this content may be determined using a factor computed from the effective carbon coefficient after analyzing the cyclic carbonyl compound by gas chromatography (GC) but for the sake of simplicity, may also be calculated from an area ratio in GC analysis. The content of the cyclic carbonyl compound having a carbon atom number of 5 or 6 in the diol feedstock is specifically measured by the method described in Examples later.

In the present invention, it is important for obtaining a polyester polyol with good color tone to reduce the content of the cyclic carbonyl compound having a carbon atom number of 5 or 6 in the raw material diol, and as long as the content of the cyclic carbonyl compound can be reduced to a predetermined value or less, any process for reducing the content of the cyclic carbonyl compound having a carbon atom number of 5 or 6 may be employed.

A diol derived from biomass resources sometimes contains, as an impurity, a nitrogen atom-containing compound ascribable to fermentation treatment and refining treatment involving a step of neutralization with an acid. Specifically, a nitrogen atom-containing compound, for example, derived from amino acid, protein, ammonia, urea and fermentation bacteria is contained.

The upper limit of the content of the nitrogen atom-containing compound in the biomass-resource-derived diol working out to a raw material of the polyester polyol in the present invention is, as the mass ratio to the diol, in terms of nitrogen atom, usually 50 ppm, preferably 20 ppm, more preferably 10 ppm, still more preferably 5 ppm. The lower limit is not particularly limited but is usually 0.01 ppm, preferably 0.1 ppm, and in view of profitability such as load reduction in the refining step, more preferably 0.2 ppm. When the content of the nitrogen atom-containing compound in the biomass-resource-derived diol is not more than the upper limit above, for example, the polycondensation reaction rate in the polyester production and the color tone of the polyester produced are more likely to become desirable. The reason why the content of the nitrogen atom-containing compound in the biomass-resource-derived diol used as the diol feedstock, which is not more than the upper limit above, is likely to be advantageous in view of, for example, the polycondensation reaction rate and color tone, is not clearly known but is presumed because the production of a coloration-inducing substance acting to inhibit the polycondensation reaction and deteriorate the color tone of a polyester polyol, other than the nitrogen atom-containing compound, can be suppressed in the refining step involving treatment and distillation of the fermentation liquid for the control of the content of the nitrogen atom-containing compound in the diol.

For example, in the case of obtaining 1,4BG by hydrogenating succinic acid obtained by fermentation of the biomass resource, the content of the nitrogen atom-containing compound in the raw material 1,4BG derived from biomass resources can be adjusted by controlling the content of the nitrogen atom-containing compound in the succinic acid by fermentation conditions, conditions of neutralization with ammonia, crystallization conditions of succinic acid, and the like. In addition, the content of the nitrogen atom-containing compound in the diol such as 1,4BG obtained by, hydrogenating succinic acid can be adjusted by refining conditions including distillation. Furthermore, also in the case where the diol such as 1,4BG is directly obtained by fermentation of the biomass resource, the content can be adjusted, for example, by the fermentation conditions, conditions of neutralization with ammonia, adsorption of amino acid by an ion exchange resin, and refining conditions including distillation of the obtained diol.

In the present invention, when using the biomass-resource-derived diol compound as a raw material of the polyester polyol, the oxygen concentration or temperature in a tank for storing the diol compound, which is connected to the reaction system, may be controlled so as to prevent the polyester polyol and furthermore, the polyurethane from coloring due to impurities above.

By the control above, coloring of the impurity itself or an oxidation reaction of the diol compound promoted by the impurity is suppressed and, for example, the polyurethane can be prevented from coloring due to an oxidation product of a diol compound such as 2-(4-hydroxybutyloxyl)tetrahydrofuran in the case of using 1,4-butanediol.

(3) Production of Polyester Polyol

The polyester polyol in the present invention is produced by subjecting the above-described dicarboxylic acid component and diol compound to an esterification and/or transesterification reaction.

The amount of the diol compound used when producing a polyester polyol is substantially equimolar to the amount of diol compound necessary for obtaining a polyester polyol having a desired molecular weight, based on the molar number of the dicarboxylic acid component, but in general, the diol compound is preferably used in excess by from 0.1 to 20 mol %, because distillation out of the diol compound occurs during the esterification and/or transesterification reaction.

The esterification and/or transesterification reaction is preferably performed in the presence of an esterification catalyst. The timing of addition of the esterification catalyst is not particularly limited, and the catalyst may be added at the time of charging of raw materials, may be added after removing water to some extent, or may be added at the start of pressure reduction.

In the case of using the dicarboxylic acid as the raw material, the raw material dicarboxylic acid itself shows the catalytic action and therefore, it is a common practice to perform the reaction without adding the catalyst at the initial reaction stage and when the reaction rate becomes insufficient in response to the production rate of produced water, add an esterification catalyst different from the raw material component. On this occasion, the timing of addition of the esterification catalyst different from the raw material component is preferably when the reaction rate of esterification reaction in progress relative to the esterification reaction rate at the initial reaction stage without addition of the catalyst becomes ⅓ or less, more preferably than ⅕ or less, because the reaction is advantageously easy to control.

The esterification catalyst includes, for example, a compound containing a metal element belonging to Groups 1 to 14 of the periodic table excluding a hydrogen atom and a carbon atom. Specifically, the catalyst includes, for example, an organic group-containing compound such as carboxylate, metal alkoxide, organic sulfonate or β-diketonate salt each containing at least one or more metals selected from the group consisting of titanium, zirconium, tin, antimony, cerium, germanium, zinc, cobalt, manganese, iron, aluminum, magnesium, calcium, strontium, sodium and potassium, an inorganic compound such as oxide or halide of the metal above, and a mixture thereof.

Incidentally, for the above-described reason, such a catalyst component is sometimes contained in the raw material derived from biomass resources. In this case, the raw material may be used directly as a metal-containing raw material without performing any particular refining of the raw material.

Among those esterification catalysts, a metal compound containing titanium, zirconium, germanium, zinc, aluminum, magnesium or calcium, and a mixture thereof are preferred, and a titanium compound, a zirconium compound and a germanium compound are more preferred. In addition, for the reason that the reaction rate is increased when the catalyst is in a melted or dissolved state at the time of esterification reaction, the catalyst is preferably a compound that is liquid at the time of esterification reaction or dissolves in the polyester polyol produced.

The titanium compound as the esterification catalyst is preferably, for example, a tetraalkyl titanate and specifically includes tetra-n-propyl titanate, tetraisopropyl titanate, tetra-n-butyl titanate, tetra-tert-butyl titanate, tetraphenyl titanate, tetracyclohexyl titanate, tetrabenzyl titanate, and a mixed titanate thereof.

Also, preferable titanium compounds include, for example, titanium (oxy)acetylacetonate, titanium tetraacetylacetonate, titanium (diisopropoxide)acetylacetonate, titanium bis(ammonium lactato)dihydroxide, titanium bis(ethyl acetoacetate)diisopropoxide, titanium (triethanolaminate) isopropoxide, polyhydroxytitanium stearate, titanium lactate, titanium triethanolaminate, and butyl titanate dimer.

Furthermore, preferable titanium compounds also include, for example, titanium oxide and a composite oxide containing titanium and silicon (e.g., titania/silica composite oxide).

Among these, tetra-n-propyl titanate, tetraisopropyl titanate, tetra-n-butyl titanate, titanium (oxy)acetylacetonate, titanium tetraacetylacetonate, titanium bis(ammonium lactato)dihydroxide, polyhydroxytitanium stearate, titanium lactate, butyl titanate dimer, titanium oxide and a titania/silica composite oxide are preferred; tetra-n-butyl titanate, titanium (oxy)acetylacetonate, titanium tetraacetylacetonate, polyhydroxytitanium stearate, titanium lactate, butyl titanate dimer and a titania/silica composite oxide are more preferred; and tetra-n-butyl titanate, polyhydroxytitanium stearate, titanium (oxy)acetylacetonate, titanium tetraacetylacetonate and a titania/silica composite oxide are still more preferred.

Examples of the zirconium compound as the esterification catalyst include zirconium tetraacetate, zirconium acetate hydroxide, zirconium tris(butoxy)stearate, zirconyl diacetate, zirconium oxalate, zirconyl oxalate, ammonium zirconium oxalate, potassium zirconium oxalate, polyhydroxyzirconium stearate, zirconium ethoxide, zirconium tetra-n-propoxide, zirconium tetraisopropoxide, zirconium tetra-n-butoxide, zirconium tetra-tert-butoxide, zirconium tributoxyacetylacetonate, and a mixture thereof.

Furthermore, zirconium oxide and a composite oxide containing zirconium and silicon are also suitably used as the zirconium compound.

Among these, zirconyl diacetate, zirconium tris(butoxy) stearate, zirconium tetraacetate, zirconium acetate hydroxide, ammonium zirconium oxalate, potassium zirconium oxalate, polyhydroxyzirconium stearate, zirconium tetra-n-propoxide, zirconium tetraisopropoxide, zirconium tetra-n-butoxide and zirconium tetra-tert-butoxide are preferred; zirconyl diacetate, zirconium tetraacetate, zirconium acetate hydroxide, zirconium tris(butoxy)stearate, ammonium zirconium Oxalate, zirconium tetra-n-propoxide and zirconium tetra-n-butoxide are more preferred; and zirconium tris (butoxy)stearate is still more preferred.

The germanium compound as the esterification catalyst specifically includes, for example, an inorganic germanium compound such as germanium oxide and germanium chloride, and an organic germanium compound such as tetraalkoxygermanium. In view of cost and ease of availability, germanium oxide, tetraethoxygermanium, tetrabutoxygermanium, etc. are preferred, and germanium oxide is more preferred.

In the case of using a metal compound as such an esterification catalyst, the lower limit value of the amount of the catalyst used is usually, as the mass concentration in terms of metal relative to the polyester polyol produced, preferably 1 ppm, more preferably 3 ppm, and the upper limit value is, usually, preferably 30,000 ppm, more preferably 1,000 ppm, still more preferably 250 ppm, yet still more preferably 130 ppm. By setting the amount of the catalyst used to 30,000 ppm or less, not only this is economically advantageous but also the thermal stability of the polyester polyol obtained can be enhanced. Also, by setting the amount of the catalyst used to 1 ppm or more, the polymerization activity at the time of reaction for the production of a polyester polyol can be enhanced.

As for the reaction temperature in the esterification reaction and/or transesterification reaction of the dicarboxylic acid component and the diol component, the lower limit is, usually, preferably 150° C., more preferably 180° C., and the upper limit is, usually, preferably 260° C., more preferably 250° C. The reaction atmosphere is usually an inert gas atmosphere such as nitrogen and/or argon. The reaction pressure is, usually, preferably from ordinary pressure to 10 Torr, more preferably from ordinary pressure to 100 Torr.

The lower limit of the reaction time is, usually, preferably 10 minutes, and the upper limit is, usually, preferably 10 hours, more preferably 5 hours.

In addition, the esterification reaction and/or transesterification reaction are performed under ordinary pressure or reduced pressure, and the timing of pressure reduction and the degree of pressure reduction are preferably adjusted in response to the reaction rate and in response to the boiling point of the raw material diol compound or in the case of allowing an azeotropic solvent to coexist, the boiling point thereof. In order to perform a more stable operation, it is preferred that the reaction is performed under ordinary pressure at the start of esterification reaction and/or transesterification reaction and after the reaction rate of esterification reaction and/or transesterification reaction in progress becomes ½ or less of the initial rate, the pressure reduction is started at the desired timing. The timing for starting the pressure reduction may be either before or after the timing of addition of the catalyst.

As the reaction apparatus used for the production of a polyester polyol, a known vertical or horizontal stirring tank-type reaction vessel can be used. For example, there is a method using a stirring tank-type reaction vessel equipped with an exhaust pipe for pressure reduction connecting a vacuum pump and a reaction vessel. A method where a condenser is coupled between exhaust pipes for pressure reduction connecting a vacuum pump and a reaction vessel and volatile components formed during the polycondensation reaction or unreacted raw materials are recovered by the condenser is preferred.

In an industrial production method, the reaction is judged mainly by the outflow of a distillation component to determine the end point of reaction, but the appropriate outflow is dependent on the boiling point (ease of flowing out) of the raw material diol compound. In general, the reaction end point is determined by the acid value during the reaction. In addition, depending on the case, a treatment of adjusting the polyester polyol to a desired molecular weight (recondensation or depolymerization by the addition of the raw material diol compound) is added. Furthermore, the reaction end point is generally decided in response to the outflow, but when the product is measured for the acid value after the completion of reaction and the acid value falls outside the target standard, the esterification reaction and/or transesterification reaction are again carried out to adjust the acid value of the produced polyester polyol to the desired acid value.

The acid value of the polyester polyol, by which the reaction end point is determined, is preferably 1.0 mgKOH/g or less, more preferably 0.5 mgKOH/g or less, still more preferably 0.2 mgKOH/g or less. Also, the preferable water amount at the completion of reaction is preferably 200 ppm or less, more preferably 100 ppm or less, still more preferably 50 ppm or less, and in order to appropriately adjust the acid value and water amount at the end point, depending on the case, the reaction can also be performed by adding an azeotropic solvent capable of azeotroping water and forming two phases and free from active hydrogen. The azeotropic solvent is not particularly limited as long as it has such performances, but an inexpensive aromatic compound such as benzene and toluene is employed in general.

After the reaction for production of a polyester polyol, the product may be stored as it is or fed to a urethanation reaction or may be subjected to a treatment of deactivating the added catalyst and then stored or fed to a urethanation reaction. The method for deactivating the added catalyst is not particularly limited, but use of a catalyst deactivating additive such as phosphite trimester is more preferred than a method having a concern for breaking the polyester polyol structure, such as water treatment.

(4) Polyester Polyol

As the polyester polyol for use in the production of the polyurethane of the present invention, specifically, a polyester polyol produced by subjecting a dicarboxylic acid component and a diol compound in the following combination to an esterification or transesterification reaction may be exemplified.

The polyester polyol using succinic acid includes, for example, a polyester polyol of succinic acid and ethylene glycol, a polyester polyol of succinic acid and 1,3-propylene glycol, a polyester polyol of succinic acid and 2-methyl-1,3-propanediol, a polyester polyol of succinic acid and 3-methyl-1,5-pentanediol, a polyester polyol of succinic acid and neopentyl glycol, a polyester polyol of succinic acid and 1,6-hexamethylene glycol, a polyester polyol of succinic acid and 1,4-butanediol, and a polyester polyol of succinic acid and 1,4-cyclohexanedimethanol.

The polyester polyol using oxalic acid includes, for example, a polyester polyol of oxalic acid and ethylene glycol, a polyester polyol of oxalic acid and 1,3-propylene glycol, a polyester polyol of oxalic acid and 2-methyl-1,3-propanediol, a polyester polyol of oxalic acid and 3-methyl-1,5-pentanediol, a polyester polyol of oxalic acid and neopentyl glycol, a polyester polyol of oxalic acid and 1,6-hexamethylene glycol, a polyester polyol of oxalic acid and 1,4-butanediol, and a polyester polyol of oxalic acid and 1,4-cyclohexanedimethanol.

The polyester polyol using adipic acid includes, for example, a polyester polyol of adipic acid and ethylene glycol, a polyester polyol of adipic acid and 1,3-propylene glycol, a polyester polyol of adipic acid and 2-methyl-1,3-propanediol, a polyester polyol of adipic acid and 3-methyl-1,5-pentanediol, a polyester polyol of adipic acid and neopentyl glycol, a polyester polyol of adipic acid and 1,6- hexamethylene glycol, a polyester polyol of adipic acid and 1,4-butanediol, and a polyester polyol of adipic acid and 1,4-cyclohexanedimethanol.

In addition, a polyester polyol using two or more of the above-described dicarboxylic acids in combination is also preferred, and such a polyester polyol includes a polyester polyol of succinic acid, adipic acid and ethylene glycol, a polyester polyol of succinic acid, adipic acid and 1,4-butanediol, a polyester polyol of terephthalic acid, adipic acid and 1,4-butanediol, a polyester polyol of terephthalic acid, succinic acid and 1,4-butanediol, and the like.

The number average molecular weight (Mn) in terms of hydroxyl value of these polyester polyols is, usually, preferably from 500 to 5,000, more preferably from 700 to 4,000, still more preferably from 800 to 3,000. When the number average molecular weight of the polyester polyol is 500 or more, a polyurethane satisfied with physical properties is obtained by using the polyester polyol, and when the molecular weight is 5,000 or less, the viscosity of the polyester polyol is kept from becoming too high, leading to good handleability.

Furthermore, the molecular weight distribution (Mw/Mn) of the polyester polyol as measured by GPC (gel permeation chromatography) is, usually, preferably from 1.2 to 4.0, more preferably from 1.5 to 3.5, still more preferably from 1.8 to 3.0. By setting the molecular weight distribution to a range of 1.2 or more, the profitability of the polyester polyol production is enhanced, and by setting the molecular weight distribution to a range of 4.0 or less, the physical properties of the polyurethane obtained using the polyester polyol are enhanced.

In the case of performing the reaction for the polyurethane production without using a solvent, the polyester polyol is preferably liquid at 40° C., and furthermore, the viscosity at 40° C. is preferably 15,000 mPa·s or less.

The polyester polyol of the present invention may be solid or liquid (in a liquid state) at ordinary temperature without any particular limitation but in view of handling, is preferably liquid at ordinary temperature.

The content of nitrogen atoms contained in the polyester polyol of the present invention except for those in covalently bonded functional groups is preferably 1,000 ppm or less as the mass concentration in the polyester polyol. The content of nitrogen atoms contained in the polyester polyol except for those in covalently bonded functional groups is preferably 500 ppm or less, more preferably 100 ppm or less, still more preferably 50 ppm or less, yet still more preferably 40 ppm or less, even yet still more preferably 30 ppm or less, and most preferably 20 ppm or less.

The content of nitrogen atoms contained in the polyester polyol of the present invention except for those in covalently bonded functional groups is mainly derived from the nitrogen atom in the raw material, and when the content of nitrogen atoms contained in the polyester polyol except for those in covalently bonded functional groups is 20 ppm or less, coloring of the polyurethane is suppressed.

The polyester polyol of the present invention is, usually, preferably a polyester polyol with less coloring. The upper limit of the value expressed by the color tone b value of the polyester polyol of the present invention is, usually, preferably 1.5, more preferably 1.1, still more preferably 0.8, yet still more preferably 0.65. On the other hand, the lower limit thereof is not particularly limited but is, usually, preferably −2, more preferably −1.5, still more preferably −0.8.

The polyester polyol having a color tone b value of 1.5 or less is advantageous in that, for example, no limitation is imposed on the use and application, such as film and sheet, of the polyurethane using this polyester polyol as the raw material. On the other hand, a polyester polyol having a color tone b value of −2 or more is economically advantageous, because the production process of producing the polyester polyol is not cumbersome and an extremely expensive equipment investment is not necessary.

In the present invention, for the production of the polyurethane, one of the above-described polyester polyols may be used alone, or two or more of known polyols may be mixed and used.

[Production of Polyurethane]

The production method of a polyurethane by the present invention is described below.

In the present invention, a polyurethane is produced by producing the above-described polyester polyol while controlling the content of a cyclic carbonyl compound having a carbon atom number of 5 or 6, and reacting the obtained polyester polyol with an isocyanate compound. At this time, a chain extender may be used, if desired.

(1) Isocyanate Compound

The isocyanate compound for use in the present invention includes, for example, an aromatic diisocyanate such as 2,4- or 2,6-tolylene diisocyanate, xylylene diisocyanate, 4,4'-diphenylmethane diisocyanate (MDI), para-phenylene diisocyanate, 1,5-naphthalene diisocyanate and tolidine diisocyanate; an aromatic ring-containing aliphatic diisocyanate such as α,α,α',α'-tetramethylxylylene diisocyanate; an aliphatic diisocyanate such as methylene diisocyanate, propylene diisocyanate, lysine diisocyanate, 2,2,4- or 2,4,4-trimethylhexamethylene diisocyanate and 1,6-hexamethylene diisocyanate; and an alicyclic diisocyanate such as 1,4-cyclohexane diisocyanate, methylcyclohexane diisocyanate (hydrogenated TDI), 1-isocyanato-3-isocyanatomethyl-3,5,5-trimethylcyclohexane (IPDI), 4,4'-dicyclohexylmethane diisocyanate and isopropylidenedicyclohexyl-4,4'-diisocyanate. One of these compounds may be used alone, or two or more thereof may be mixed and used.

In the present invention, in the application requiring weather resistance, such as synthetic or artificial leather and coating material, an aliphatic diisocyanate and/or an alicyclic diisocyanate are preferably used, because yellowing by light hardly occurs. Among others, in view of good physical properties and ease of availability, 1,6-hexamethylene diisocyanate, 1-isocyanato-3-isocyanatomethyl-3,5,5-trimethylcyclohexane and 4,4'-dicyclohexylmethane diisocyanate are preferably used. On the other hand, in the application requiring strength, such as elastic fiber, an aromatic diisocyanate with high cohesive force is preferably used, and in view of good physical properties and ease of availability, it is more preferred to use tolylene diisocyanate (TDI) and diphenylmethane diisocyanate (hereinafter, sometimes referred to as "MDI"). In addition, an isocyanate compound where a part of NCO groups is modified into urethane, urea, burette, allophanate, carbodiimide, oxazolidone, amide, imide, etc. may also be used, and furthermore, the polynuclear form encompasses compounds containing an isomer other than those described above.

The amount used of such an isocyanate compound is, usually, preferably from 0.1 to 10 equivalents, more preferably from 0.8 to 1.5 equivalents, still more preferably from 0.9 to 1.05 equivalents, per equivalent of the hydroxyl group of the polyester polyol and the hydroxyl group and amino group of the chain extender.

By setting the amount used of the isocyanate compound to a range of not more than the upper limit above, an undesirable reaction of an unreacted isocyanate group is prevented from occurring, as a result, desired physical properties are easily obtained, and by setting the amount used of the isocyanate compound to a range of not less than the lower limit above, the molecular weight of the obtained polyurethane sufficiently grows, making it possible to exert desired performances.

The isocyanate compound reacts with water contained in a polyurethane feedstock other than the isocyanate compound, such as polyester polyol or chain extender, and partially disappears and therefore, an amount to compensate for the loss may be added to the desired amount used of the isocyanate compound. Specifically, the polyester polyol, chain extender, etc. are measured for the water amount before being mixed with the isocyanate compound at the time of reaction, and an isocyanate compound having isocyanate groups corresponding to two times the amount of the substance containing the water is added in a predetermined use amount.

The mechanism by which the isocyanate group reacts with water and disappears is that an isocyanate group becomes an amine compound by the reaction with a water molecule and the amine compound further reacts with an isocyanate group to form a urea bond, as a result, two isocyanate groups disappear per one water molecule. There is a fear that this disappearance makes the necessary isocyanate compound lacking and desired physical properties are not obtained, and therefore, it is effective to add an isocyanate compound for making up the amount corresponding to the water amount by the method described above.

(2) Chain Extender

In the present invention, a chain exchanger having two or more active hydrogens may be used, if desired. The chain extender is classified mainly into a compound having two or more hydroxyl groups and a compound having two or more amino groups. Of these, a short-chain polyol, specifically, a compound having two or more hydroxyl groups, is preferable for the polyurethane application, and a polyamine compound, specifically, a compound having two or more amino groups, is preferable for the polyurethane urea application.

In addition, when a compound having a molecular weight (number average molecular weight) of 500 or less is used in combination as the chain extender, rubber elasticity of a polyurethane elastomer is enhanced, and therefore, this is more preferred in view of physical properties.

The compound having two or more hydroxyl groups includes, for example, an aliphatic glycol such as ethylene glycol, diethylene glycol, triethylene glycol, propylene glycol, dipropylene glycol, tripropylene glycol, 1,3-propanediol, 1,2-butanediol, 1,3-butanediol, 1,4-butanediol, 2,3-butanediol, 3-methyl-1,5-pentanediol, neopentyl glycol, 2-methyl-1,3-propanediol, 2-methyl-2-propyl-1,3-propanediol, 2-butyl-2-ethyl-1,3-propanediol, 1,5-pentanediol, 1,6-hexanediol, 2-methyl-2,4-pentanediol, 2,2,4-trimethyl-1,3-pentanediol, 2-ethyl-1,3-hexanediol, 2,5-dimethyl-2,5-hexanediol, 2-butyl-2-hexyl-1,3-propanediol, 1,8-octanediol, 2-methyl-1,8-octanediol and 1,9-nonanediol; an alicyclic glycol such as bishydroxymethylcyclohexane; and an aromatic ring-containing glycol such as xylylene glycol and bishydroxyethoxybenzene.

The compound having two or more amino groups includes, for example, an aromatic diamine such as 2,4- or 2,6-tolylenediamine, xylylenediamine and 4,4'-diphenylmethanediamine; an aliphatic diamine such as ethylenediamine, 1,2-propylenediamine, 1,6-hexanediamine, 2,2-dimethyl-1,3-propanediamine, 2-methyl-1,5-pentanediamine, 1,3-diaminopentane, 2,2,4- or 2,4,4-trimethylhexanediamine, 2-butyl-2-ethyl-1,5-pentanediamine, 1,8-octanediamine, 1,9-nonanediamine and 1,10-decanediamine; and an alicyclic diamine such as 1-amino-3-aminomethyl-3,5,5-trimethylcyclohexane (IPDA), 4,4'-dicyclohexylmethanediamine (hydrogenated MDA), isopropylidenecyclohexyl-4,4'-diamine, 1,4-diaminocyclohexane and 1,3-bisaminomethylcyclohexane.

Among these, ethylene glycol, diethylene glycol, 1,3-propanediol, 1,4-butanediol, 3-methyl-1,5-pentanediol, neopentyl glycol, 2-methyl-1,3-propanediol, isophoronediamine, hexamethylenediamine, ethylenediamine, propylenediamine, 1,3-diaminopentane and 2-methyl-1,5-pentanediamine are preferred in the present invention, and in view of ease of handling or storage and excellent balance of physical properties of the obtained polyurethane, 1,4-butanediol is more preferred.

For the chain extender as well, a biomass-resource-derived chain extender may also be used, and in this case, the production method therefor is the same as the production method of the above-described biomass-resource-derived diol compound.

Of these chain extenders, a compound having a hydroxyl group is preferred when using an aromatic polyisocyanate as the isocyanate compound, and a compound having an amino group is preferred when using an aliphatic polyisocyanate. In addition, one of these chain extenders may be used alone, or two or more thereof may be mixed and used.

The amount used of the chain extender is not particularly limited but, usually, preferably from 0.1 to 10 equivalents per equivalent of the polyester polyol.

By setting the amount used of the chain extender to a range of not more than the upper limit above, the obtained polyurethane (or polyurethane urea) can be prevented from becoming excessively hard and not only desired characteristics are obtained but also the resin is easily soluble in a solvent, making the processing easy. Also, by setting the amount used to a range of not less than the lower limit, the obtained polyurethane (or polyurethane urea) can be kept from becoming excessively soft and not only sufficient strength and elasticity recovering performance or elasticity retaining performance are obtained but also high-temperature characteristics can be enhanced.

In the present invention, in the case of a diol compound for the chain extender, the compound is preferably used by controlling the content of the cyclic carbonyl compound having a carbon atom number of 5 or 6, and the upper limit of the content of the cyclic carbonyl compound having a carbon atom number of 5 or 6 in the diol compound as the chain extender is usually 100 ppm, preferably 50 ppm, more preferably 12 ppm, still more preferably 2 ppm. The lower limit is usually 0.01 ppm, preferably 0.1 ppm, more preferably 0.2 ppm, and from the economical view point of the refining step, the lower limit is preferably 0.5 ppm. When the content of the cyclic carbonyl compound having a carbon atom number of 5 or 6 in the biomass-resource-derived diol compound, particularly, in 1,4-butanediol, is not more than the upper limit above, the color tone in the polyurethane production tends to become good. On the other hand, when the content is not less than the lower limit, the refining step of the biomass-resource-derived diol compound becomes simple, which is economically advantageous.

(3) Chain Terminator

In the present invention, for the purpose of controlling the molecular weight of the obtained polyurethane, a chain terminator having one active hydrogen group may be used, if desired. Examples of the chain terminator include an aliphatic monohydroxy compound having a hydroxyl group, such as methanol, ethanol, propanol, butanol and hexanol, and an aliphatic monoamine having an amino group, such as morpholine, diethylamine, dibutylamine, monoethanolamine and diethanolamine. One of these compounds may be used alone, or two or more thereof may be mixed and used.

(4) Crosslinking Agent

In the present invention, for the purpose of increasing the heat resistance or strength of the obtained polyurethane, a crosslinking agent having three or more active hydrogen groups or isocyanate groups may be used, if desired. As the crosslinking agent, trimethylolpropane, glycerin and an isocyanate-modified product thereof, polymeric MDI, etc. can be used.

(5) Production of Polyurethane

In the present invention, a polyurethane is produced using the above-described polyester polyol and isocyanate compound and, if desired, using the chain extender, chain terminator, etc. described above by controlling the content of a cyclic carbonyl compound having a carbon atom number of 5 or 6 in the raw material.

In the present invention, the polyurethane may be produced by a reaction in a bulk manner, namely, without a solvent, or by a reaction in a solvent excellent in the solubility of polyurethane, such as aprotic polar solvent.

An example of the production method for a polyurethane of the present invention is described below, but the production method of a polyurethane of the present invention is not limited to the following method by any means.

The production method of a polyurethane includes, for example, a one-step method and a two-step method.

The one-step method is a method of reacting a polyester polyol, an isocyanate compound and a chain extender at the same time.

The two-step method is a method of first reacting a polyester polyol and an isocyanate compound to prepare a prepolymer having an isocyanate group at both ends, and then reacting the prepolymer with a chain extender (hereinafter, sometimes referred to "isocyanate group-terminated two-step method"). In addition, the method also includes a method of preparing a prepolymer having a hydroxyl group at both ends, and then reacting the prepolymer with an isocyanate compound.

Of these, the isocyanate group-terminated two-step method passes through a step of previously reacting a polyester polyol with 1 equivalent or more of an isocyanate compound, thereby preparing an intermediate having both ends capped with isocyanate, corresponding to the soft segment of a polyurethane.

The method of once preparing a prepolymer and then reacting it with a chain extender is characterized in that the molecular weight of the soft segment portion is easily adjusted, the phase separation between the soft segment and the hard segment is likely to be distinctly created, and the performance as an elastomer is easy to bring out.

In particular, in the case where the chain extender is a diamine, the reaction rate with an isocyanate group is greatly different from that with a hydroxyl group of the polyester polyol and therefore, it is more preferable to carry out the polyurethane urea formation by the prepolymer method.

<One-Step Method>

The one-step method is also called a one-shot method and is a method of performing the reaction by charging a polyester polyol, an isocyanate compound and a chain extender all together. The amount used of each compound may be the use amount described above.

In the one-shot method, a solvent may or may not be used. In the case of not using a solvent, the isocyanate compound and the polyester polyol, etc. may be reacted using a low-pressure foaming machine or a high-pressure foaming machine or may be reacted with stirring and mixing by using a high-speed rotary mixer.

In the case of using a solvent, the solvent includes, for example, ketones such as acetone, methyl ethyl ketone, methyl isobutyl ketone and cyclohexanone; ethers such as dioxane and tetrahydrofuran; hydrocarbons such as hexane and cyclohexane; aromatic hydrocarbons such as toluene and xylene; esters such as ethyl acetate and butyl acetate; halogenated hydrocarbons such as chlorobenzene, trichlene and perchlene; aprotic polar solvents such as γ-butyrolactone, dimethylsulfoxide, N-methyl-2-pyrrolidone, N,N-dimethylformamide and N,N-dimethylacetamide; and a mixture of two or more thereof.

Among these organic solvents, in view of solubility, an aprotic polar solvent is preferred. Preferable specific examples of the aprotic polar solvent include methyl ethyl ketone, methyl isobutyl ketone, N,N-dimethylacetamide, N,N-dimethylformamide, N-methyl-2-pyrrolidone, and dimethylsulfoxide, with N,N-dimethylformamide and N,N-dimethylacetamide being more preferred.

In the case of the one-shot method, the lower limit of the reaction equivalent ratio of NCO/active hydrogen group (polyester polyol and chain extender) is, usually, preferably 0.50, more preferably 0.8, and the upper limit is, usually, preferably 1.5, and more preferably 1.2.

By setting the reaction equivalent ratio to a range of 1.5 or less, it can be prevented that an excess isocyanate group causes a side reaction and thereby produces an undesired effect on the physical properties of the polyurethane. Also, by setting the reaction equivalent ratio to a range of 0.50 or more, the molecular weight of the obtained polyurethane can sufficiently grow, and generation of a problem with the strength or thermal stability can be inhibited.

The reaction is preferably performed at a temperature of 0 to 100° C., but this temperature is preferably adjusted according to the amount of solvent, the reactivity of raw material used, the reaction equipment, etc. If the reaction temperature is two low, the reaction proceeds too slowly and because of low solubility of the raw material or polymerization product, the productivity is bad. As well, a too high reaction temperature is not preferred, because a side reaction or decomposition of the polyurethane occurs. The reaction may be performed while degassing under reduced pressure.

Furthermore, a catalyst, a stabilizer, etc. may be added to the reaction system, if desired.

The catalyst includes, for example, triethylamine, tributylamine, dibutyltin dilaurate, dioctyltin dilaurate, dioctyltin dineodecanoate, stannous octylate, acetic acid, phosphoric acid, sulfuric acid, hydrochloric acid, and sulfonic acid.

The stabilizer includes, for example, 2,6-dibutyl-4-methylphenol, distearyl thiodipropionate, di-β-naphthylphenylenediamine, and tri(dinonylphenyl)phosphite.

<Two-Step Method>

The two-step method is also called a prepolymer process, where an isocyanate compound and a polyester polyol are previously reacted preferably in a reaction equivalent ratio of 0.1 to 10.00 to produce a prepolymer and subsequently, an isocyanate compound and an active hydrogen compound component such as the chain extender are added to the prepolymer, thereby performing a two-step reaction. In particular, a method of reacting an isocyanate compound in an equivalent amount or more relative to the polyester polyol to obtain a both end NCO-terminated prepolymer and subsequently, allowing a short-chain diol or diamine as the chain extender to act on the prepolymer to obtain a polyurethane is useful.

In the two-step method, a solvent may or may not be used. In the case of using a solvent, the solvent includes, for example, ketones such as acetone, methyl ethyl ketone, methyl isobutyl ketone and cyclohexanone; ethers such as dioxane and tetrahydrofuran; hydrocarbons such as hexane and cyclohexane; aromatic hydrocarbons such as toluene and xylene; esters such as ethyl acetate and butyl acetate; halogenated hydrocarbons such as chlorobenzene, trichlene and perchlene; aprotic polar solvents such as γ-butyrolactone, dimethylsulfoxide, N-methyl-2-pyrrolidone, N,N-dimethylformamide and N,N-dimethylacetamide; and a mixture of two or more thereof.

In the present invention, among these organic solvents, an aprotic polar solvent is preferred in view of solubility. Preferable specific examples of the aprotic polar solvent include N,N-dimethylacetamide, N,N-dimethylformamide, N-methyl-2-pyrrolidone, and dimethyl sulfoxide, with N,N-dimethylformamide and N,N-dimethylacetamide being more preferred.

In the case of synthesizing an isocyanate group-terminated prepolymer, (1) a prepolymer may be synthesized by directly reacting an isocyanate compound and a polyester polyol without using a solvent and be used as it is, (2) a prepolymer may be synthesized by the method of (1) and then used by dissolving it in a solvent, or (3) a prepolymer may be synthesized by reacting an isocyanate compound and a polyester polyol with use of a solvent.

In the case of (1), a polyurethane is preferably obtained in the form of coexisting with a solvent by a method of, for example, dissolving a chain extender in a solvent or introducing the prepolymer and a chain extender simultaneously into a solvent.

As for the reaction equivalent ratio of NCO/active hydrogen group (polyester polyol) at the time of synthesis of a prepolymer, the lower limit is, usually, preferably 0.1, more preferably 0.8, and the upper limit is, usually, preferably 10, more preferably 5, still more preferably 3.

The amount used of the chain extender is not particularly limited, but in terms of the ratio to the equivalent of NCO group or 01-1 group contained in the prepolymer, the lower limit is, usually, preferably 0.8, more preferably 0.9, and the upper limit is, usually, preferably 2, more preferably 1.2. By setting this ratio to a range of 2 or less, it can be prevented that an excess chain extender causes a side reaction and thereby produces an undesired effect on the physical properties of the polyurethane. Also, by setting the ratio to a range of 0.8 or more, the molecular weight of the obtained polyurethane can sufficiently grow, and generation of a problem with the strength or thermal stability can be inhibited.

In addition, a monofunctional organic amine or alcohol may be allowed to coexist at the time of reaction.

The reaction temperature is preferably from 0 to 250° C., but this temperature is preferably adjusted according to the amount of solvent, the reactivity of raw material used, the reaction equipment, etc. If the reaction temperature is two low, the reaction proceeds too slowly and because of low solubility of the raw material or polymerization product, the productivity is bad. As well, a too high reaction temperature is not preferred, because a side reaction or decomposition of the polyurethane occurs. The reaction may be performed while degassing under reduced pressure.

Furthermore, a catalyst, a stabilizer, etc. may be added to the reaction system, if desired.

The catalyst includes, for example, triethylamine, tributylamine, dibutyltin dilaurate, dioctyltin dilaurate, dioctyltin dineodecanoate, stannous octylate, acetic acid, phosphoric acid, sulfuric acid, hydrochloric acid, and sulfonic acid.

However, in the case where the chain extender is a compound having high reactivity, such as short-chain aliphatic amine, the reaction is preferably carried out without adding a catalyst.

The stabilizer includes, for example, 2,6-dibutyl-4-methylphenol, distearyl thiodipropionate, di-β-naphthylphenylenediamine, and tri(dinonylphenyl)phosphite.

(6) Physical Properties, Etc. of Polyurethane

The polyurethane produced by the production method of a polyurethane of the present invention (hereinafter, sometimes referred to as "polyurethane of the present invention") preferably has the following physical properties.

As for the physical properties of the polyurethane of the present invention, for example, a polyurethane using, as the raw material, a polyester polyol obtained from an aliphatic diol and an aliphatic dicarboxylic acid, such as polybutylene succinate or polybutylene succinate adipate, preferably possesses very broad physical characteristics such that the tensile breaking stress at 23° C. is from 5 to 150 MPa and the elongation at break is from 100 to 1,500%.

In the case of targeting a specialized application, a polyurethane having characteristics in an arbitrary broad range beyond the limit of the above-described range can be formed. These characteristics can be arbitrarily adjusted by varying the kind of the polyurethane feedstock or additive, the polymerization conditions, the molding conditions, and the like, according to the intended use.

The ranges of representative physical properties possessed by the polyurethane of the present invention are described below.

As for the composition ratio of the polyurethane, it is preferred that the diol unit (the constitutional unit derived from the diol compound) and the dicarboxylic acid unit are substantially equal in the molar ratio.

As for the sulfur atom content in the polyurethane of the present invention, in terms of atom, the upper limit is preferably 50 ppm, more preferably 5 ppm, still more preferably 3 ppm, and most preferably 0.3 ppm, relative to the mass of the polyurethane. On the other hand, the lower limit is not particularly limited but is preferably 0.0001 ppm, more preferably 0.001 ppm, still more preferably 0.01 ppm, yet still more preferably 0.05 ppm, and most preferably 0.1 ppm.

By setting the sulfur atom content to a range of 50 ppm or less, the thermal stability or hydrolysis resistance of the polyurethane can be enhanced. Also, by setting the content to a range of 0.001 ppm or more, an excessive rise in the refining costs is prevented, which is economically advantageous in the production of a polyurethane.

The polyurethane of the present invention is, usually, preferably a polyurethane with less coloring. As for the YI value of the polyurethane of the present invention, the upper limit is, usually, preferably 20, more preferably 10, still more preferably 5, yet still more preferably 3. On the other hand, the lower limit thereof is not particularly limited but is, usually, preferably -20, more preferably -5, still more preferably -1.

A polyurethane having a YI value of 20 or less is advantageous in that no limitation is imposed on the use and application, such as film and sheet. On the other hand, a polyurethane having a YI value of -20 or more is economically advantageous, because the production process of producing the polyurethane is not cumbersome and an extremely expensive equipment investment is not necessary.

The weight average molecular weight of the polyurethane of the present invention as measured by gel permeation chromatography (GPC) may vary depending on use but as the polyurethane, the weight average molecular weight is, usually, preferably from 10,000 to 1,000,000, more preferably from 50,000 to 500,000, still more preferably from 100,000 to 400,000, yet still more preferably from 100,000 to 300,000. As for the molecular weight distribution, Mw/Mn is preferably from 1.5 to 3.5, more preferably from 1.8 to 2.5, still more preferably from 1.9 to 2.3.

By setting the molecular weight to a range of 1,000,000 or less, the solution viscosity is kept from becoming too high, and the handleability is enhanced. Also, by setting the molecular weight to a range of 10,000 or more, the obtained polyurethane can be prevented from excessive reduction in the physical properties. By setting the molecular weight distribution to a range of 1.5 or more, the profitability of the polyurethane production is kept from excessively deteriorating, and the elastic modulus of the obtained polyurethane is enhanced. Also, by setting the molecular weight distribution to a range of 3.5 or less, the solution viscosity is kept from becoming too high, and the handleability is enhanced. In addition, the obtained polyurethane can be prevented from excessively increasing in the elastic modulus, and the elastic recovery is improved.

For example, in applications such as synthetic or artificial leather, polyurethane for shoe sole, film, sheet, tube and moisture permeable resin, the weight average molecular weight of the polyurethane is, usually, preferably from 10,000 to 1,000,000, more preferably from 50,000 to 500,000, still more preferably from 100,000 to 400,000, yet still more preferably from 150,000 to 350,000. As for the molecular weight distribution, Mw/Mn is preferably from 1.5 to 3.5, more preferably from 1.8 to 2.5, still more preferably from 1.9 to 2.3.

By setting the molecular weight to a range of 1,000,000 or less, the solution viscosity is kept from becoming too high, leading to good handleability. Also, by setting the molecular weight to a range of 50,000 or more, the obtained polyurethane can be prevented from excessive reduction in the physical properties. By setting the molecular weight distribution to a range of 1.5 or more, the profitability of the polyurethane production becomes good, and the elastic modulus of the obtained polyurethane can be enhanced. Also, by setting the molecular weight distribution to a range of 3.5 or less, the solution viscosity is kept from becoming too high, leading to good handleability. In addition, the obtained polyurethane can be prevented from excessively increasing in the elastic modulus, and the elastic recovery is improved.

A solution obtained by dissolving the polyurethane of the present invention in an aprotic solvent (hereinafter, sometimes referred to as "polyurethane solution") is convenient for the processing into a film, a yarn, etc., because gelling scarcely proceeds, the storage stability is good, such as little change over time of viscosity, and the thixotropy is low.

The polyurethane content in the polyurethane solution is, usually, preferably from 1 to 99 mass %, more preferably from 5 to 90 mass %, still more preferably from 10 to 70 mass %, yet still more preferably from 15 to 50 mass %, based on the total mass of the polyurethane solution. By setting the polyurethane content in the polyurethane solution to a range of 1 mass % or more, removal of a large amount of the solvent is not necessary, and the productivity can be enhanced. Also, by setting the content to a range of 99 mass % or less, the viscosity of the solution is suppressed, and the operability or processability can be enhanced.

Although not particularly specified, in the case of storing the polyurethane solution over a long period of time, the solution is preferably stored in an inert gas atmosphere such as nitrogen or argon.

(7) Additives of Polyurethane

In the polyurethane of the present invention, various additives may be added, if desired. These additives include, for example, an antioxidant such as CYANOX 1790 [produced by CYANAMID], IRGANOX 245, IRGANOX 1010 [both produced by Ciba Specialty Chemicals], Sumilizer GA-80 (produced by Sumitomo Chemical Co., Ltd.) and 2,6-dibutyl-4-methylphenol (BHT); a light stabilize such as TINUVIN 622LD, TINUVIN 765 [both produced by Ciba Specialty Chemicals], SANOL LS-2626 and LS-765 [both produced by Sankyo Co., Ltd.]; an ultraviolet absorber such as TINUVIN 328 and TINUVIN 234 (both produced by Ciba Specialty Chemicals); a silicon compound such as dimethylsiloxane-polyoxyalkylene copolymer; an additive and a reactive flame retardant, such as red phosphorus, organophosphorus compound, phosphorus- or halogen-containing organic compound, bromine- or chlorine-containing organic compound, ammonium polyphosphate, aluminum hydroxide and antimony oxide; a colorant, e.g., a pigment such as titanium dioxide, a dye, and carbon black; a hydrolysis inhibitor such as carbodiimide compound; a filler such as short glass fiber, carbon fiber, alumina, talc, graphite, melamine and white clay; a lubricant; an oil; a surfactant; and other inorganic extenders and organic solvents. In addition, a blowing agent such as water and chlorofluorocarbon alternative may also be added, and this addition is useful, among others, in a polyurethane foam for shoe sole.

(8) Polyurethane Molded Article and Use

The polyurethane of the present invention and the polyurethane solution thereof can exert a variety of characteristics and can be widely used as a foam, an elastomer, a coating material, a fiber, an adhesive, a floor material, a sealant, a medical material, an artificial leather, etc. The uses [1] to [11] are described below, but the application of the polyurethane of the present invention and the polyurethane solution thereof is not limited to the followings by any means.

[1] Use as a Casting Polyurethane Elastomer

For example, rolls such as rolling roll, papermaking roll, office equipment and pretension roll; solid tires and casters for a forklift, an automotive vehicle new tram, a carriage, a carrier, etc.; industrial products such as conveyor belt idler, guide roll, pulley, steel pipe lining, rubber screen for ore, gears, connection ring, liner, impeller for pump, cyclone cone and cyclone liner; belts for OA equipment; paper feed rolls; squeegees; cleaning blades for copying; snowplows; toothed belts; and surf rollers.

[2] Use as a Thermoplastic Elastomer

For example, tubes or hoses in a pneumatic component for food and medical fields, a coating apparatus, an analytical instrument, a physicochemical apparatus, a metering pump, a water treatment apparatus, an industrial robot, etc.; spiral tubes and fire hoses; and belts such as round belt, V-belt and flat belt, in various transmission mechanisms, spinning machines, packaging devices and printing machines.

[3]

Heel tops and shoe soles of footwear; device components such as cup ring, packing, ball joint, bushing, gear and roll; sports goods; leisure goods; wristwatch belts; etc.

[4] As an Automotive Component

Oil stoppers, gear boxes, spacers, chassis parts, interior trims, tire chain substitutes, films such as key board film and automotive film, curl cords, cable sheaths, bellows, conveying belts, flexible containers, binders, synthetic leathers, dipping products, adhesives, etc.

[5] Use as a Solvent-Based Two-Pack Coating Material

For example, wood products such as musical instrument, family Buddhist altar, furniture, decorative plywood and sports goods; and as a tar-epoxy-urethane, automotive repairs.

[6] Component of a Moisture-Curable One-Pack Type Coating Material, a Block Isocyanate-Based Solvent Coating Material, an Alkyd Resin Coating Material, a Urethane-Modified Synthetic Resin Coating Material, an Ultraviolet-Curable Coating Material, Etc.

For example, coating materials for plastic bumper, strippable paints, coating materials for magnetic tape, overprint varnishes for floor tile, floor material, paper, wood grain printed film, etc., varnishes for wood, coil coats for high processing, optical fiber protective coatings, solder resists, topcoats for metal printing, base coats for vapor deposition, and white coats for food can.

[7] As an Adhesive

Shoes, footwear, magnetic tape binders, decorative paper, wood, structural members, etc.; and components of low-temperature usable adhesive or hot-melt adhesive.

[8] As a Binder

Magnetic recording mediums, inks, castings, burned bricks, grafting materials, microcapsules, granular fertilizers, granular agrochemicals, polymer cement mortars, resin mortars, rubber chip binders, reclaimed foams, glass fiber sizing, etc.

[9] As a Component of Fiber Processing Agent

Shrink proofing, crease proofing, water repellent finishing, etc.

[10] As a Sealant/Caulking Material

Concrete walls, induced joints, peripheries of sash, wall-type PC joints, ALC joints, board joints, sealants for composite glass, heat-insulating sash sealants, automotive sealants, etc.

[11] Use as a Polyurethane for Shoe Sole, a Synthetic Leather, and an Artificial Leather In this case, the raw material polyester polyol component may have a skeleton of adipic acid, sebacic acid, etc. In addition, a polyurethane that is derived from plants and is biodegradable, is more suitable for non-durable consumer goods such as resin for shoe.

(9) Artificial Leather or Synthetic Leather

An artificial leather or a synthetic leather, which is one example of representative applications of the polyurethane of the present invention, is described in detail below.

The artificial leather or synthetic leather has, as major constituent elements, a base cloth, an adhesive layer, and a skin layer.

The skin layer is formed using a skin layer blended solution obtained by mixing the polyurethane of the present invention with other resins, an antioxidant, an ultraviolet absorber, etc. to prepare a polyurethane resin solution, and mixing the solution with a colorant, an organic solvent, etc. In addition, a hydrolysis inhibitor, a pigment, a dye, a flame retardant, a filler, a crosslinking agent, etc. can be added, if desired, to the polyurethane solution.

Other resins include, for example, a polyurethane other than the polyurethane of the present invention, a poly(meth) acrylic resin, a vinyl chloride-vinyl acetate-based copolymer, a vinyl chloride-vinyl propionate-based copolymer, a polyvinyl butyral-based resin, a cellulose-based resin, a polyester resin, an epoxy resin, a phenoxy resin, and a polyamide resin.

The crosslinking agent includes, for example, a polyisocyanate compound such as organic polyisocyanate, crude MDI, TDI adduct of trimethylolpropane, and triphenylmethane isocyanate.

The base cloth includes, for example, Tetron/rayon, a napped cotton cloth, a knitted cloth, and a nylon tricot cloth. The adhesive includes, for example, a two-pack polyurethane composed of a polyurethane, a polyisocyanate compound and a catalyst.

The polyisocyanate compound includes, for example, a TDI adduct of trimethylolpropane. The catalyst includes, for example, an amine-based or tin-based catalyst.

For producing an artificial or synthetic leather using the polyurethane of the present invention, first, the polyurethane of the present invention is mixed with other resins, etc. to prepare a polyurethane solution, and the solution is then mixed with a colorant, etc. to prepare a skin layer blended solution. Subsequently, this blended solution is coated on a release paper and dried, an adhesive is further coated thereon to form an adhesive layer, a base cloth such as napped cloth is laminated thereto and dried, and after aging at room temperature for a few days, the release paper is separated, whereby an artificial leather or a synthetic leather is obtained.

The produced artificial leather or synthetic leather can be used for clothing, shoe, bag, etc.

EXAMPLES

The present invention is described in greater detail below, but the present invention is not limited by the following Examples as long as the gist of the present invention is observed.

[Analysis Method]

<Content (Ppm by Mass) in Terms of Nitrogen Atom of a Nitrogen-Containing Compound in 1,4BG>

15 mg of 1,4BG was collected on a quartz boat, and the sample was burnt using a trace total nitrogen analyzer (model code: "Model TN-10", manufactured by Dia Instruments Co., Ltd.) and quantitatively determined by a combustion and chemiluminescence method. As the standard sample employed, those having a concentration of 0, 0.5, 1.0 and 2.0 µg/mL in terms of nitrogen atom were produced by dissolving aniline in toluene and used.

<Contents (Ppm by Mass) of a Cyclic Carbonyl Compound Having a Carbon Atom Number of 5 or 6 and Other Components in 1,4BG>

The content of the component at each peak, such as 1,4BG, was determined according to a corrected area percentage method computed from the effective carbon coefficient in gas chromatograph analyzer "Model Shimadzu GC-2014" manufactured by Shimadzu Corporation by using column PEG-20M (polar) manufactured by GL Science.

Incidentally, the amount of the cyclic carbonyl compound having a carbon atom number of 5 or 6 is small and therefore, the sample was injected into the gas chromatograph analyzer by not diluting the sample with a solvent. Also, the amount of the cyclic carbonyl compound having a carbon atom number of 5 or 6 was calculated from the ratio between the area value of 1,4BG and the area value of the cyclic carbonyl compound without making a correction to the effective carbon coefficient.

The ketone and/or aldehyde each having a carbon atom number of 5 or 6 can be detected by GC-MS and/or GC-IR and can be discriminated from other components in the refined 1,4BG. These are presumed to be 2-acetyltetrahydrofuran and 2-methyldihydro-2H-pyran-3(4H)-one.

2-Acetyltetrahydrofuran (hereinafter, referred to as "ATF"):
GC-MS (EI): 86, 71, 43, 29
GC-IR: 2980, 2885, 1734, 1454, 1360, 1176, 1080, 925 cm$^{-1}$ 2-Methyldihydro-2H-pyran-3(4H)-one (hereinafter, referred to as "MHPO")
GC-MS (EI): 114, 71, 42, 29
GC-IR: 2956, 2851, 1742, 1240, 1115 cm$^{-1}$ In the following, the total of ATF and MHPO is defined as the total of cyclic carbonyl compounds having a carbon atom number of 5 or 6 and is referred to as "total $C_5, C_6$ cyclic carbonyl". Also, the component higher in the boiling point than 1,4BG is referred to as "high-boiling-point component", and the component lighter in the boiling point than 1,4BG is referred to as "light-boiling-point component". Each of the components is simply referred to as follows:
GBL: gamma-butyrolactone
1,4HAB: 1-acetoxy-4-hydroxybutane
BGTF: 2-(4-hydroxybutyloxyl)tetrahydrofuran In the following, both "ppm" and "%" indicating the component composition are a value on the mass basis.

<Production Volumes of Water and THF in PBT Production>

A distillate in an esterification reaction was determined for water amount by the Karl Fisher's method (measured by "CA-03", manufactured by Mitsubishi Chemical Corporation), and the rest except for water was regarded as organic components. The THF amount in the organic components was determined by the above-described gas chromatography method and taken as the THF production volume. The THF production volume was expressed by mol % relative to terephthalic acid, and the obtained value was taken as the conversion ratio.

<Intrinsic Viscosity (IV) of PBT>

The intrinsic viscosity was determined using an Ubbelohde viscometer by the following procedure. That is, using a mixed solvent of phenol/tetrachloroethane (mass ratio: 1/1), the falling time in seconds was measured at 30° C. on a PBT solution having a concentration of 1.0 g/dL and on only the solvent, and the viscosity was determined according to the following formula:

$$IV=[(1+4K_H \eta_{sp})^{0.5}-1]/(2K_H C)$$

wherein $\eta_{sp}=(\eta/\eta_0)-1$, $\eta$ is the falling time in seconds of the PBT solution, $\eta_0$ is the falling time in seconds of the solvent, C is the PBT concentration (g/dL) of the PBT solution, and $K_H$ is the Huggins' constant. A value of 0.33 was adopted for $K_H$.

<Terminal Carboxyl Group Concentration (Equivalent/Ton) of PBT>

0.5 g of PBT was dissolved in 25 mL of benzyl alcohol, the resulting solution was titrated using a 0.01 mol/L benzyl alcohol solution of sodium hydroxide, and the concentration was calculated according to the following formula:

Terminal carboxyl group concentration=$(A-B) \times 0.1 \times f / W$(equivalent/ton)

wherein A is the amount (μL) of the benzyl alcohol solution of 0.01 N sodium hydroxide required for titration, B is the amount (μL) of the benzyl alcohol solution of 0.01 mol/L sodium hydroxide required for titration of the blank, W is the amount (g) of the PBT sample, and f is the factor of the 0.01 mol/L sodium hydroxide.

<Color Tone (b Value) of PBT>

A columnar powder measurement cell having an inner diameter of 30 mm and a depth of 12 mm was filled with pellet-shaped PBT. Using a colorimetric color-difference meter, Color Meter ZE2000 (manufactured by Nippon Denshoku Industries Co., Ltd.), the value was determined as a simple average value of the values measured in four places by the reflection method while rotating the measurement cell at every 90°. The color tone was evaluated by the b value in the L, a, b color system. A lower b value indicates that the color tone is better with less yellowing.

<Reduced Viscosity (dl/g) of PBS>

Using a phenol/tetrachloroethane (mass ratio: 1/1) mixed solution as the solvent and adjusting the concentration (c) to 0.5 g/dl (deciliter), 0.25 g of pellet-shaped PBS was dissolved by keeping the temperature at 110° C. for 30 minutes. Thereafter, the relative viscosity (ηrel) to the original solution was measured at 30° C. by a Ubbelohde capillary viscometer, and the ratio (ηsp/C) of the specific viscosity (ηsp) determined from the relative viscosity (ηrel)-1 to the concentration (c) was determined.

<Color Tone (YI Value) of PBS>

A columnar powder measurement cell having an inner diameter of 30 mm and a depth of 12 mm was filled with pellet-shaped PBS. Using a colorimetric color-difference meter, Color Meter ZE2000 (manufactured by Nippon Denshoku Industries Co., Ltd.), the color was measured based on the method of JIS K7105. The value was determined as a simple average value of the values measured in four places by the reflection method while rotating the measurement cell at every 90°.

<Color Tone b Value of Polyester Polyol>

A columnar powder measurement cell having an inner diameter of 30 mm and a depth of 12 mm was filled with plate-shaped polyester polyol. Using a colorimetric color-difference meter, Color Meter ZE2000 (manufactured by Nippon Denshoku Industries Co., Ltd.), the value was determined as a simple average value of the values measured in four places by the reflection method while rotating the measurement cell at every 90°. The color tone was evaluated by the b value in the L, a, b color system. A lower b value indicates that the color tone is better with less yellowing.

<Number Average Molecular Weight of Polyester Polyol>

The number average molecular weight of the polyester polyol was determined by the hydroxyl value (OH value: mgKOH/g). A polyester polyol sample was heat-treated together with a phthalating agent and thereby phthalated, and the hydroxyl value was then measured using an automatic titrator. As the phthalating agent, a solution obtained by adding and dissolving 500 ml of pyridine (Kanto Chemical Co., Inc., guaranteed reagent) in 70 g of phthalic anhydride (Kanto Chemical Co., Inc.) and allowing the resulting solution to stand still overnight was used. When adding the phthalating agent to the polyester polyol sample, the sample amount needs to be adjusted according to the number of hydroxyl groups, and the sample amount was weighed by taking, as a guide, the following formula:

S=561/N (S [g]: the mass of sample, N [mgKOH/g]: the expected hydroxyl value).

The polyester polyol sample was weighed in 200 ml conical flask, and exactly 25 ml of the phthalating agent was poured therein by means of a volumetric pipette. After confirming that the sample was dissolved, an air-cooled cooling tube (length: about 40 cm) was attached, and the solution was heated on an oil bath set at 100±2° C. without stirring for 1 hour. Titration was performed with an aqueous 0.5 mol/L NaOH solution (Kanto Chemical Co., Inc.) by using Automatic Titrator GT-100, manufactured by Mitsubishi Chemical Analytech Co., Ltd.) as the automatic titrator and using GTPC15B as the electrode.

<Mass Average Molecular Weight of Polyurethane>

The polyurethane was measured for the weight average molecular weight in terms of standard polystyrene by using a GPC apparatus manufactured by Tosoh Corporation (product name: HLC-8220, column: TSKgel GMH-XL.two columns, solvent: lithium bromide-added N,N-dimethylacetamide).

<Water Amount in Polyurethane Production>

The analysis of water at the time of polyurethane production was performed by the Karl Fisher's method. A water analyzer, Model CA-21, manufactured by Mitsubishi Chemical Corporation was used as the apparatus, and Aquamicron AKX and Aquamicron CXU were used as an anolyte and a catholyte, respectively.

<Color Tone YI Value of Polyurethane>

The transmission measurement was performed using a colorimetric color-difference meter (product name: ZE2000) manufactured by Nippon Denshoku Industries Co., Ltd. and using a liquid cell having an inner width of 1 cm. The polyurethane sample was two-fold diluted with N,N-dimethylacetamide and used after removing bubbles under reduced pressure.

[Raw Material 1,4BG]

As 1,4BG directly produced by a fermentation process, crude 1,4BG obtained by the method described in JP-T-2010-521182 (the term "JP-T" as used herein means a published Japanese translation of a PCT patent application) and U.S. Patent Application Publication No. US2011/0003355 and further subjected to dehydration was gained from Genomatica, Inc. and refined by the method described in Reference Example 1 below to obtain Bio-Process 1,4BG (B) (hereinafter, sometimes simply referred to as "Bio-Process (B)").

As 1,4BG by a fossilization process, a product industrially available in practice was used.

1,4BG by a butadiene process (hereinafter, sometimes simply referred to as "Butadiene Process (C)") is obtained by performing an acetoxylation reaction of butadiene, acetic acid and oxygen to obtain diacetoxybutene as an intermediate and hydrogenating and hydrolyzing the diacetoxybutene.

1,4BG by a propylene process (hereinafter, sometimes simply referred to as "Propylene Process (D)") is obtained by an oxo reaction of an allyl alcohol obtained by oxidation of propylene.

Reference Example 1

Refining of Bio-Process (B)

Refining of crude 1,4BG for obtaining Bio-Process (B) was performed by the following method. The composition of crude 1,4BG of Bio-Process (B) before refining is shown in Table 1.

Using a glass-made rotary evaporator, first, dehydration/concentration of crude 1,4BG was performed. This operation was performed at an inner temperature of 175° C. by setting the pressure to 10.7 kPa. The distillation percentage was 10 mass %, and a 1,4BG solution remaining in the flask was recovered in an amount of 90 mass % relative to the amount charged. The composition of 1,4BG after the dehydration is shown in Table 1.

Next, batch distillation was performed using, as the raw material, the 1,4BG solution after dehydration and using a glass-made instrument, and the distillate was separated into a plurality of fractions, thereby separating the high-boiling portion and the light-boiling portion from 1,4BG. At this time, a multistage distillation column corresponding to 3 plates as the theoretical plate was used. The top pressure was set to 13.3 kPa, and the bottom temperature was controlled to 182° C. The distillation temperature elevated along with removal of the light-boiling portion and thereafter, settled at 175° C. The stream when the top temperature settled was collected as 1,4BG. The fraction of 1,4BG was recovered in an amount of 90 mass % relative to the raw material amount charged. The composition of the fraction of this refined 1,4BG (Bio-Process (B)) is also shown in Table 1.

TABLE 1

| Component | Unit | Before Refining (crude 1,4BG) | After Dehydration | After Refining (Bio-Process (B)) |
|---|---|---|---|---|
| Light-boiling-point component | ppm | 158 | 469 | 118 |
| ATF | ppm | 102 | 254 | 6 |
| MHPO | ppm | 118 | 477 | 7 |
| Water | % | 9.3 | 0.025 | 0.002 |
| GBL | ppm | 103 | 137 | 0 |
| 1,4HAB | ppm | 184 | 191 | 2 |
| 1,4BG | % | 90.3 | 99.4 | 99.8 |
| BGTF | ppm | 636 | 792 | 1195 |
| High-boiling-point component | ppm | 2699 | 3430 | 242 |
| Nitrogen atom | ppm | 42 | 48 | 4.7 |
| Total $C_5$, $C_6$ cyclic carbonyl | ppm | 220 | 731 | 13 |

Subsequently, 1,4BG (Bio-Process (B)) having the composition after refining in Table 1 was further separated into a plurality of fractions by using the same batch distillation apparatus, whereby 8 lots of refined Bio-Process (B) differing in the content of total $C_5$,$C_6$ cyclic carbonyl, etc. were obtained. These lots are designated, starting from the initial distillate, as Lot 1, Lot 2, Lot 3, Lot 4, Lot 5, Lot 6, Lot 7 and Lot 8. The composition of each lot is as shown in Table 2 later.

Production of PBT

Example 1

A reaction vessel equipped with a stirring device, a nitrogen inlet, a heating device, a thermometer, a distillation tube and an evacuation port for pressure reduction was charged with 113 g of terephthalic acid, 183 g of raw material 1,4BG as Lot 1 of Bio-Process (B) and 0.7 parts by mass of a 1,4BG solution of Bio-Process (B) having previously dissolved therein 6 mass % of tetrabutyl titanate as a catalyst, and a nitrogen atmosphere was created in the system by nitrogen-vacuum purging. After warming the inside of the system to 150° C. with stirring, the temperature was raised to 220° C. over 1 hour under atmospheric pressure, and an esterification reaction was further performed for 2 hours while distilling out water produced.

Subsequently, 1.3 g of a 1,4BG solution of Lot 1 of Bio-Process (B) with 1 mass % magnesium acetate tetrahydrate, obtained by dissolving magnesium acetate tetrahydrate in water and further dissolving the resulting solution in 1,4BG (mass ratio of magnesium acetate tetrahydrate, water and 1,4BG: 1:2:97), was added.

Thereafter, the temperature was held at 220° C. for 0.25 hours, then raised to 245° C. over 0.75 hours and held. On the other hand, the pressure was reduced to 0.07 kPa over 1.5 hours from the initiation of polymerization, and a polycondensation reaction was performed for 0.8 hours under the same reduced pressure. The reaction system was returned to ordinary pressure to thereby complete the polycondensation. The obtained PBT was withdrawn as a strand from the bottom part of the reaction tank and passed under water at 10° C., and the strand was cut by a cutter to obtain pellet-shaped PBT.

The period from the initiation of pressure reduction after the addition of magnesium acetate to the completion of polycondensation was taken as the polycondensation time, and the intrinsic viscosity/polycondensation time was defined as the polycondensation rate. The polycondensation rate was 0.35 dL/g/hr. As for the THF conversion ratio, the THF amount was analyzed on a sample obtained by cooling and collecting a distillate during the esterification reaction by a dry ice trap, and the obtained value was expressed by mol % per terephthalic acid charged. This THF conversion ratio was 54 mol %.

The analysis results of the obtained PBT by the measurement methods described above and the composition of Lot 1 of Bio-Process (B) used as the raw material 1,4BG are shown in Table 2.

Example 2

PBT was produced utterly in the same manner except that in Example 1, the raw material 1,4BG was changed to Lot 2 obtained in the refining of Bio-Process (B). The conversion ratio [%] into THF, polycondensation time [hr] and polycondensation rate [dL/g/hr] at the time of PBT production and the analysis results of PBT by the measurement methods above are shown together in Table 2.

Example 3

PBT was produced utterly in the same manner except that in Example 1, the raw material 1,4BG was changed to Lot 3 obtained in the refining of Bio-Process (B). The conversion ratio [%] into THF, polycondensation time [hr] and polycondensation rate [dL/g/hr] at the time of PBT production and the analysis results of PBT by the measurement methods above are shown together in Table 2.

Example 4

PBT was produced utterly in the same manner except that in Example 1, the raw material 1,4BG was changed to Lot 4 obtained in the refining of Bio-Process (B). The conversion ratio [%] into THF, polycondensation time [hr] and polycondensation rate [dL/g/hr] at the time of PBT production and the analysis results of PBT by the measurement methods above are shown together in Table 2.

Example 5

PBT was produced utterly in the same manner except that in Example 1, the raw material 1,4BG was changed to Lot 5 obtained in the refining of Bio-Process (B). The conversion ratio [%] into THF, polycondensation time [hr] and polycondensation rate [dL/g/hr] at the time of PBT production and the analysis results of PBT by the measurement methods above are shown together in Table 2.

Example 6

PBT was produced utterly in the same manner except that in Example 1, the raw material 1,4BG was changed to Lot 6 obtained in the refining of Bio-Process (B). The conversion ratio [%] into THF, polycondensation time [hr] and polycondensation rate [dL/g/hr] at the time of PBT production and the analysis results of PBT by the measurement methods above are shown together in Table 2.

Example 7

PBT was produced utterly in the same manner except that in Example 1, the raw material 1,4BG was changed to Lot 7 obtained in the refining of Bio-Process (B). The conversion ratio [%] into THF, polycondensation time [hr] and polycondensation rate [dL/g/hr] at the time of PBT production and the analysis results of PBT by the measurement methods above are shown together in Table 2.

Example 8

PBT was produced utterly in the same manner except that in Example 1, the raw material 1,4BG was changed to Lot 8 obtained in the refining of Bio-Process (B) and the polycondensation time was changed to the time shown in Table 2. The conversion ratio [%] into THF, polycondensation time [hr] and polycondensation rate [dL/g/hr] at the time of PBT production and the analysis results of PBT by the measurement methods above are shown together in Table 2.

Comparative Example 1

PBT was produced utterly in the same manner except that in Example 1, the raw material 1,4BG was changed to Bio-Process (B) and the polycondensation time was changed to the time shown in Table 2. The conversion ratio [%] into THF, polycondensation time [hr] and polycondensation rate [dL/g/hr] at the time of PBT production and the analysis results of PBT by the measurement methods above are shown together in Table 2.

Comparative Example 2

PBT was produced utterly in the same manner except that in Example 1, the raw material 1,4BG was changed to Propylene Process (D) having the composition shown in Table 2 and the polycondensation time was changed to the time shown in Table 2. The conversion ratio [%] into THF, polycondensation time [hr] and polycondensation rate [dL/g/hr] at the time of PBT production and the analysis results of PBT by the measurement methods above are shown together in Table 2.

TABLE 2

| | | Example/Comparative Example | | | | |
|---|---|---|---|---|---|---|
| | | Example 1 | Example 2 | Example 3 | Example 4 | Example 5 |
| Kind of raw material 1,4BG | Name | Bio-Process (B) | | | | |
| | | Lot 1 | Lot 2 | Lot 3 | Lot 4 | Lot 5 |
| | Process | direct fermentation | direct fermentation | direct fermentation | direct fermentation | direct fermentation |
| Composition of raw material 1,4BG* | Nitrogen content (ppm) | 1.4 | 1.0 | 1.0 | 0.6 | 1.9 |
| | Total $C_5$, $C_6$ carbonyl (ppm) | ND | 2 | 7 | 5 | 4 |
| | ATF (ppm) | ND | 1 | 5 | 3 | 1 |
| | MHPO (ppm) | ND | 1 | 2 | 2 | 3 |
| | 1,4BG (%) | 99.9 | 99.9 | 99.8 | 99.8 | 99.9 |
| | BGTF (ppm) | 1100 | 1100 | 1110 | 1545 | 1123 |
| | 1,4HAB (ppm) | 10 | 26 | 22 | 13 | 25 |
| PBT Production | Conversion ratio into THF (%) | 64.2 | 70.6 | 67.4 | 63.3 | 61.1 |
| | Polycondensation time (hr) | 2.3 | 2.3 | 2.3 | 2.3 | 2.3 |
| | Polycondensation Rate (dL/g/h) | 0.37 | 0.37 | 0.38 | 0.37 | 0.38 |
| Physical properties of PBT | Color tone b value | 1.1 | 1.6 | 1.7 | 1.9 | 2.2 |
| | Intrinsic viscosity (dL/g) | 0.85 | 0.85 | 0.87 | 0.84 | 0.87 |
| | Terminal carboxyl group concentration (equivalent/ton) | 4 | 7 | 8 | 5 | 7 |

| | | Example/Comparative Example | | | | |
|---|---|---|---|---|---|---|
| | | Example 6 | Example 7 | Example 8 | Comparative Example 1 | Comparative Example 2 |
| Kind of raw material 1,4BG | Name | Bio-Process (B) | | | Bio-Process (B) | Propylene Process (D) |
| | | Lot 6 | Lot 7 | Lot 8 | | |
| | Process | direct fermentation | direct fermentation | direct fermentation | direct fermentation | petroleum-derived |
| Composition of raw material 1,4BG* | Nitrogen content (ppm) | 0.6 | 0.7 | 3.2 | 3.5 | ND |
| | Total $C_5$, $C_6$ carbonyl (ppm) | 6 | 7 | 10 | 13 | ND |
| | ATF (ppm) | 4 | 4 | 4 | 6 | ND |
| | MHPO (ppm) | 2 | 3 | 6 | 7 | ND |
| | 1,4BG (%) | 99.8 | 99.8 | 99.9 | 99.8 | 99.7 |
| | BGTF (ppm) | 1461 | 1332 | 1212 | 2000 | 1210 |
| | 1,4HAB (ppm) | 16 | 14 | 13 | 100 | ND |
| PBT Production | Conversion ratio into THF (%) | 63.3 | 65.6 | 57 | 59.1 | 75.1 |
| | Polycondensation time (hr) | 2.3 | 2.4 | 2.3 | 2.4 | 2.4 |
| | Polycondensation Rate (dL/g/h) | 0.37 | 0.36 | 0.37 | 0.35 | 0.35 |
| Physical properties of PBT | Color tone b value | 2.5 | 2.5 | 2.7 | 4.9 | 1.9 |
| | Intrinsic viscosity (dL/g) | 0.84 | 0.86 | 0.84 | 0.83 | 0.84 |
| | Terminal carboxyl group concentration (equivalent/ton) | 5 | 7 | 5 | 4 | 11 |

*ND: Below detection lower limit; in case of nitrogen atom, less than 0.1 ppm, and in case of ATF, MHPO, total $C_5$, $C_6$ carbonyl and 1,4HAB, less than 1 ppm.

Figure 2:
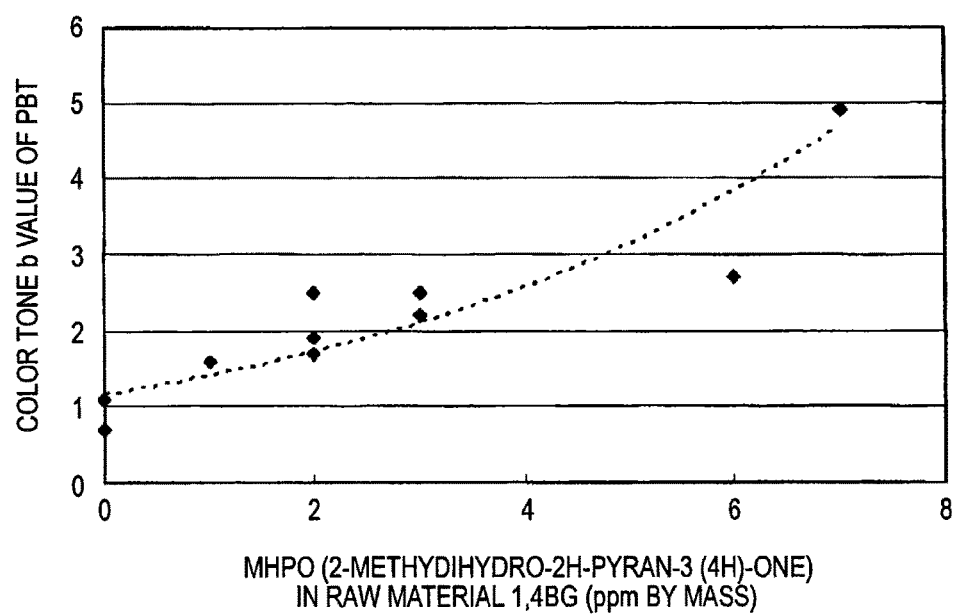
FIG. 2 is a graph showing the correlation between the content of 2-methyldihydro-2H-pyran-3(4H)-one in the bio-process 1,4BG used as a PBT feedstock in Examples 1 to 9 and Comparative Example 1 and the color tone b value of the obtained PBT.

FIG. 1 shows the correlation between the total $C_5$,$C_6$ cyclic carbonyl content in the bio-process 1,4BG used in Examples 1 to 8 and Comparative Example 1 and the color tone b value of the obtained PBT, and FIG. 2 shows the correlation between the MHPO content in 1,4BG and the color tone b value of the obtained PBT.

In FIGS. 1 and 2, the content below detection limit is shown as "ND=0 ppm by mass". The same applies to FIGS. 3 and 4 later.

It can be understood from these results that the color tone b value of PBT is greatly affected by the total $C_5$,$C_6$ cyclic carbonyl content in the raw material 1,4 BG, particularly, by the MHPO content, and an approximate curve with very high correlation can be drawn.

Accordingly, it is revealed that in the case of using biomass-resource-derived 1,4BG as the PBT feedstock, controlling the content of a cyclic carbonyl compound having a carbon atom number of 5 or 6, such as MHPO, in the raw material 1,4BG is effective in producing PBT with good color tone.

Comparative Example 3

PBT was produced in the same manner as in Example 1 except that in Example 1, the raw material 1,4BG was changed to Butadiene Process (C) not containing a cyclic carbonyl compound having a carbon atom number of 5 or 6. The color tone b value of the obtained PBT was 1.3.

Comparative Example 4

PBT was produced utterly in the same manner as in Comparative Example 3 except that Butadiene Process (C) used in Comparative Example 3 was used by adding thereto 40 ppm by mass of reagent 4-hydroxy-2-butanone (produced by TCI) (carbon atom number: 4). The color tone b value of the obtained PBT was 2.0.

Comparative Example 5

PBT was produced utterly in the same manner as in Comparative Example 3 except that Butadiene Process (C) used in Comparative Example 3 was used by adding thereto 80 ppm by mass of reagent 4-hydroxy-2-butanone (produced by TCI) (carbon atom number: 4). The color tone b value of the obtained PBT was 2.4.

Comparative Example 6

PBT was produced utterly in the same manner as in Comparative Example 3 except that Butadiene Process (C) used in Comparative Example 3 was used by adding thereto 32 ppm by mass of reagent methyl vinyl ketone (produced by TCI) (carbon atom number: 4). The color tone b value of the obtained PBT was 3.3.

Comparative Example 7

PBT was produced utterly in the same manner as in Comparative Example 3 except that Butadiene Process (C) used in Comparative Example 3 was used by adding thereto 600 ppm by mass of reagent normal-butyl aldehyde (produced by Wako) (carbon atom number: 4). The color tone b value of the obtained PBT was 3.3.

The results of Comparative Examples 3 to 7 are shown in Table 3 together with the results of Example 1 and Comparative Example 1.

Figure 3:
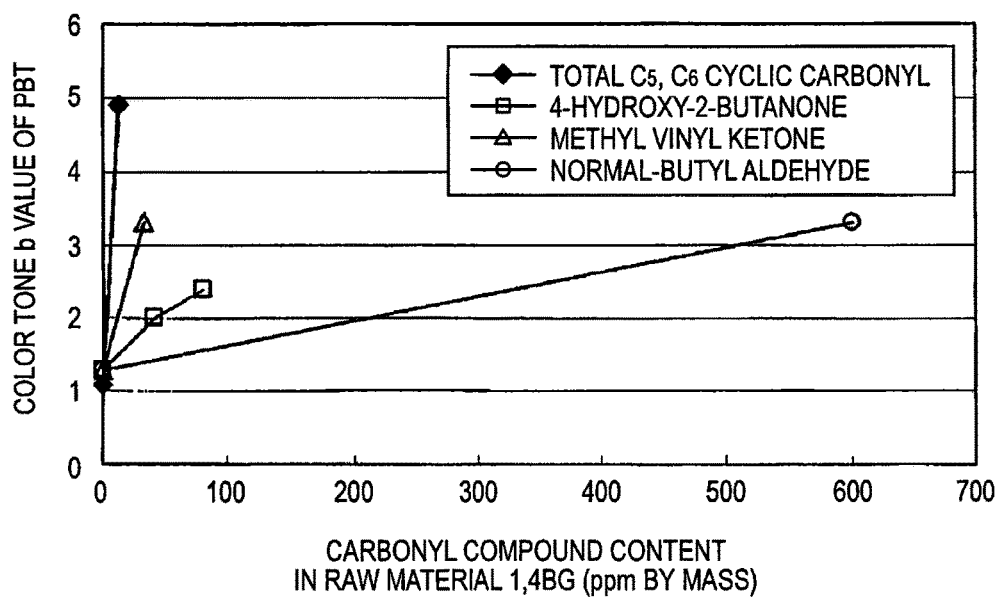
FIG. 3 is a graph showing the correlation between the content of a carbonyl compound in the 1,4BG used as a PBT feedstock in Example 2 and Comparative Examples 3 to 7 and the color tone b value of the obtained PBT.
Figure 4:
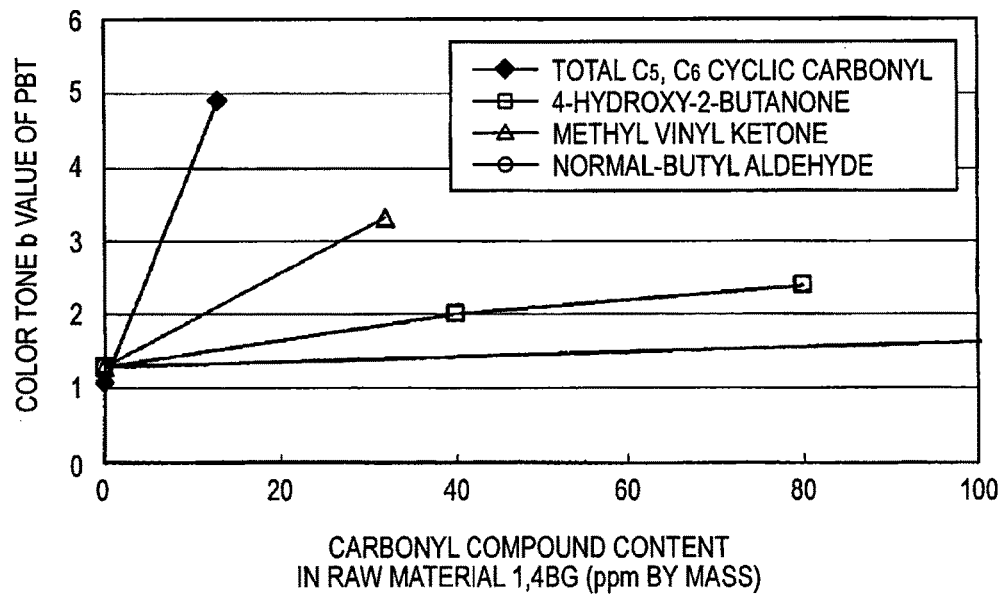
FIG. 4 is an enlarged view of FIG. 3 in the range of the carbonyl compound content being from 0 to 100 ppm by mass.

Also, FIGS. 3 and 4 (FIG. 4 is an enlarged view of FIG. 3) show the correlation between the content of a carbonyl compound in 1,4BG and the color tone b value of the obtained PBT.

Incidentally, in Table 3, the "Degree of Increase of Color Tone b Value" is, in the case of Comparative Example 1, a value obtained by dividing the increase of color tone b value (Δb value) relative to the color tone b value of PBT produced using Lot 1 of Bio-Process (B) of Example 1 where the carbonyl compound and total $C_5,C_6$ cyclic carbonyl contents are ND, by the carbonyl compound content (ppm) and is calculated as follows:

Degree of increase of color tone $b$ value=(4.9−1.1)/13=0.29

In the case of Comparative Examples 4 to 7, the degree of increase is a value obtained by dividing the increase (Δb value) of color tone b value relative to the color tone b value of PBT produced using Butadiene Process (C) of Comparative Example 3 where the carbonyl compound and total $C_5,C_6$ cyclic carbonyl contents are ND, by the carbonyl compound content (ppm) and, for example, in Comparative Example 4, is calculated as follows:

Degree of increase of color tone $b$ value=(2.0−1.3)/40=0.018

TABLE 3

| | | Example 1 | Comparative Example 1 | Comparative Example 3 | Comparative Example 4 | Comparative Example 5 | Comparative Example 6 | Comparative Example 7 |
|---|---|---|---|---|---|---|---|---|
| Raw material 1,4BG | Name | Bio-Process (B) (Lot 1) | Bio-Process (B) | Butadiene Process (C) | | | | |
| | Process | direct fermentation | | petroleum-derived | | | | |
| | Carbonyl compound (reagent) added to 1,4BG | — | — | — | 4-hydroxy-2-butanone | 4-hydroxy-2-butanone | methyl vinyl ketone | normal-butyl aldehyde |
| | Carbonyl compound content (ppm)* | ND | 13 | ND | 40 | 80 | 32 | 600 |
| | Total $C_5$, $C_6$ carbonyl content (ppm)* | ND | 13 | ND | ND | ND | ND | ND |
| | Color tone b value of PBT | 1.1 | 4.9 | 1.3 | 2.0 | 2.4 | 3.3 | 3.3 |
| | Degree of increase of color tone b value | — | 0.29 | — | 0.018 | 0.014 | 0.063 | 0.0033 |

*ND: Below detection lower limit; less than 1 ppm.

As seen from the results of Comparative Examples 1 and 4 to 7, the degree of increase of the color tone b value of PBT (Δb value/carbonyl compound content (ppm)) by the increase in the content of a cyclic carbonyl compound having a carbon atom number of 5 or 6 in 1,4BG is 88 times that by normal-butyl aldehyde and 21 times that by 4-hydroxy-2-butanone and even when compared with methyl vinyl ketone having very high reactivity and high polymerization activity, is as large as 5 times.

It is understood from these results that the effect of the content of a cyclic carbonyl compound having a carbon atom number of 5 or 6 in the raw material 1,4BG on the color tone b value of PBT is very large as compared with the effects of other general carbonyl compounds (ketone, aldehyde, unsaturated carbonyl) on the color tone b value.

Production of PBS

Example 9

(Preparation of Polycondensation Catalyst)

100 g of magnesium acetate tetrahydrate was put in a glass-made eggplant-shaped flask equipped with a stirring device, and 1,500 g of anhydrous ethanol (purity: 99 mass % or more) was further added. In addition, 130.8 g of ethyl acid phosphate (mixing mass ratio of monoester form and diester form: 45:55) was added, and the mixture was stirred at 23° C. After 15 minutes, it was confirmed that the magnesium acetate was completely dissolved, and thereafter, 529.5 g of tetra-n-butyl titanate was added. Stirring was continued for another 10 minutes to obtain a uniform mixed solution. This mixed solution was transferred to an eggplant-shaped flask and concentrated under reduced pressure by an evaporator in an oil bath at 60° C. After 1 hour, the ethanol was mostly distilled out, and a semitransparent viscous liquid was obtained. The temperature of the oil bath was further raised to 80° C., and the liquid was further concentrated under reduced pressure of 5 Torr to obtain a viscous liquid. This liquid catalyst was dissolved in 1,4-butanediol, and the solution was adjusted to have a titanium atom content of 3.5 mass %. The storage stability in 1,4-butanediol was good, and in the catalyst solution stored at 40° C. in a nitrogen atmosphere, formation of a precipitate was not observed for at least 40 days.

(Production of PBS)

A reaction vessel equipped with a stirring device, a nitrogen inlet, a heating device, a thermometer and an evacuation port for pressure reduction was charged with, as raw materials, 68.4 parts by mass of succinic acid, 67.8 parts by mass of 1,4BG of Lot 4 of Bio-Process (B) used in Example 5, and 0.25 parts by mass of malic acid, and a nitrogen atmosphere was created in the system by nitrogen-vacuum purging. Subsequently, the temperature was raised to 230° C. over 60 minutes while stirring the inside of the system, and an esterification reaction was performed at 230° C. for 60 minutes under nitrogen at atmospheric pressure while distilling out water or tetrahydrofuran produced. After the completion of esterification reaction, the catalyst solution above was added, and the polycondensation reaction was started. The amount of the catalyst solution added was adjusted to an amount corresponding to 50 ppm by mass in terms of titanium atom per the obtained polyester. The polycondensation reaction was performed under the temperature conditions that the temperature is kept at 230° C. for 30 minutes while stirring the inside of the system, raised to 250° C. over 30 minutes, and held. On the other hand, the pressure was reduced to 0.13 kPa over 90 minutes from the start of polycondensation, and the reaction was further performed for 153 minutes under reduced pressure of 0.13 kPa to obtain PBS.

The reduced viscosity of the obtained PBS was 2.0 dl/g, and the YI value was 19.

Production of Polyester Polyol

Example 10

A polyester polyol was produced according to the following method by using, as 1,4BG, Lot 8 of refined 1,4BG obtained in Reference Example 1.

Using a 1-L four-neck flask equipped with a 100-ml scaled ester tube, a 100-ml dropping funnel, a thermometer and a stirring bar, dehydration condensation was performed under the following conditions by heating the flask in an oil bath.

241.5 g of 1,4BG was added to 321.2 g of adipic acid (Wako Pure Chemical Industries, Ltd.) and after heating the mixture at an inner temperature of 150° C. for 30 minutes, the temperature was raised to an inner temperature of 220° C. over about 1 hour. After reaching an inner temperature of 220° C., the pressure was reduced to 600 torr, and toluene (Wako Pure Chemical Industries, Ltd.) was added to obtain an adequate reflux flow rate to the flask from the inside of the ester tube. Ten minutes after the start of pressure reduction, 0.0264 ml of titanium tetraisopropoxide (Wako Pure Chemical Industries, Ltd.) was added. The acid value of water produced by the reaction was measured as needed, and heating was performed until the acid value became 0.5 KOHmg/g. The amount of water produced by the reaction was 79.3 g. After the completion of reaction, toluene was distilled out at 30 torr and an inner temperature of 140° C. to obtain 484 g of a polyester polyol. The number average molecular weight (Mn) of the obtained polyester polyol was 1,400, and the color tone b value was −0.5.

Comparative Example 8

A polyester polyol was produced by the same method as in Example 10 except that 1,4BG after dehydration distillation obtained by the same method as in Reference Example 1 (different in the lot of crude 1,4BG from Reference Example 1) was used as 1,4BG The number average molecular weight (Mn) of the obtained polyester polyol was 1,400, and the color tone b value was 9.8.

Reference Example 2

A polyester polyol was produced in the same manner as in Example 10 except that Butadiene Process (C) not containing a cyclic carbonyl compound having a carbon atom number of 5 or 6 was used as 1,4BG. The number average molecular weight (Mn) of the obtained polyester polyol was 1,400, and the color tone b value was 0.6.

These results are shown together in Table 4.

TABLE 4

| | | Example/Comparative Example | | |
|---|---|---|---|---|
| | | Example 10 | Comparative Example 8 | Reference Example 2 |
| Raw material 1,4BG | Name | Bio-Process (B) (Lot 8) | Bio-Process (B) (no removal of light-boiling portion) | Butadiene Process (C) |
| | Process | direct fermentation | | petroleum-derived |
| | Total $C_5$, $C_6$ carbonyl content (ppm)* | 10 | 1005 | ND |
| | Color tone b value of polyester polyol | −0.5 | 9.8 | 0.6 |

*ND: Below detection lower limit; less than 1 ppm

It is seen from Table 4 that in the case of using biomass-resource-derived 1,4BG as a raw material of the polyester polyol, a polyester polyol having good color tone can be produced by using raw material 1,4BG reduced in the total $C_5$,$C_6$ cyclic carbonyl content.

Production of Polyurethane

Example 11

A polyester polyol was produced in the same manner as in Example 10 except that. Lot 5 of refined 1,4BG obtained in Reference Example 1 was used as 1,4BG. The amount of water produced by the reaction was 79.2 g, and 482 g of a polyester polyol was obtained. The number average molecular weight (Mn) of the obtained polyester polyol was 2,000.

In a dry box (water content: 10% or less) with flowing dry air, 70.0 g of polybutylene adipate obtained above (hydroxyl value: 56 KOHmg/g, number average molecular weight: 2,000) and, as a chain extender, 6.3 g of Lot 5 of refined 1,4BG obtained in Reference Example 1 were added to a reaction vessel (1-L separable flask) equipped with a thermometer, a stirring device and a nitrogen blowing tube, the mixture was diluted with 240.0 g of N,N-dimethylacetamide (hereinafter, referred to as DMAc) (Wako Pure Chemical Industries, Ltd., guaranteed reagent), and furthermore, 0.017 g of a dioctyltin catalyst (Nitto Kasei Co., Ltd.: NEOSTANN U-830) (50 mol ppm as tin) was added. The reaction vessel was heated with stirring in an oil bath (50° C.) for about 1 hour so as to make the DMAc solution uniform. The water amount of the resulting DMAc solution was measured, and the required amount of diphenylmethane diisocyanate (hereinafter, referred to as MDI) (Nippon Polyurethane Industry Co., Ltd.: Millionate MT) was calculated.

Specifically, assuming that 1 mol of water deactivates 1 mol of MDI, the necessary number of NCO groups was calculated. As a result, 32.84 g of MDI afforded the equivalent. The reaction vessel was heated to 70° C., MDI was gradually added with stirring, and the reaction product was sampled every time the compound was added, and measured for the mass average molecular weight (Mw) by using GPC. As a result, at the point where the amount of MDI added was 0.95 times the equivalent, Mw of polyurethane was 51,000, and the color tone YI of polyurethane was 0.68. This polyurethane was stored in a closed vessel in a cold dark place. After the elapse of 1 week, the color tone YI of the polyurethane was again measured and found to be 0.73.

Comparative Example 9

A polyester polyol was produced in the same manner as in Example 10 by using, as 1,4BG, Bio-Process (B) in Reference Example 1, and a polyurethane was produced in the same manner as in Example 11 except for using the produced polyester polyol and using, as a chain extender, 1,4BG of Bio-Process (B). At the point where the amount of MDI added was 0.95 times the equivalent, Mw of polyurethane was 84,000, and the color tone YI of polyurethane was 1.12. This polyurethane was stored in a closed vessel in a cold dark place. After the elapse of 1 week, the color tone YI of the polyurethane was again measured and found to be 44.35.

Reference Example 3

A polyurethane was produced in the same manner as in Example 11 except for using the polyester polyol obtained in Reference Example 2 and using, as a chain extender, 1,4-Butadiene Process (C) not containing a cyclic carbonyl compound having a carbon atom number of 5 or 6. At the point where the amount of MDI added was 0.95 times the equivalent, Mw of polyurethane was 49,000, and the color tone YI of polyurethane was 0.75. This polyurethane was stored in a closed vessel in a cold dark place. After the elapse of 1 week, the color tone YI of the polyurethane was again measured and found to be 0.93.

It is seen from Table 5 that in the case of using biomass-resource-derived 1,4BG as a raw material, a polyurethane having good color tone immediately after production and having no problem of deterioration of color tone with aging can be produced by using raw material 1,4BG reduced in the total $C_5,C_6$ cyclic carbonyl content and a polyester polyol produced using raw material 1,4BG reduced in the total $C_5,C_6$ cyclic carbonyl content.

While the invention has been described in detail and with reference to specific embodiments thereof, it will be apparent to one skilled in the art that various changes and modifications can be made therein without departing from the spirit and scope of the invention. This application is based on Japanese Patent Application (Patent Application No. 2012-128066) filed on Jun. 5, 2012 and Japanese Patent Application (Patent Application No. 2013-39247) filed on Feb. 28, 2013, the contents of which are incorporated herein by way of reference.

The invention claimed is:

1. A method for producing a polyester, comprising:
   performing a reaction by using, as raw materials, a dicarboxylic acid component, and a diol produced directly from a biomass-resource-derived substance by a fermentation process,
   wherein a content of a cyclic carbonyl compound having a carbon atom number of 5 or 6 in the diol is from 0.01 ppm to 12 ppm by mass, and
   wherein said diol produced directly from a biomass-resource-derived substance by a fermentation process is selected from the group consisting of ethylene glycol, 2-methyl-1,3-propanediol, neopentyl glycol, 1,4-butanediol, 1,5-pentanediol, 1,6-hexanediol, 1,4-cyclohexanediol, 1,4-cyclohexanedimethanol, and isosorbide.

2. The method for producing a polyester according to claim 1,
   wherein the cyclic carbonyl compound having a carbon atom number of 5 or 6 contains a compound having a structure represented by the following formula (I):

TABLE 5

| | | | Example/Comparative Example | | |
| --- | --- | --- | --- | --- | --- |
| | | | Example 11 | Comparative Example 9 | Reference Example 3 |
| Raw material diol for production of polyester polyol | Raw material 1,4BG | Name | Bio-Process (B) (Lot 5) | Bio-Process (B) | Butadiene Process (C) |
| | | Process | direct fermentation | | petroleum-derived |
| | | Total $C_5$, $C_6$ carbonyl content (ppm)* | 4 | 13 | ND |
| Raw material diol for production of polyurethane | Chain extender 1,4BG | Name | Bio-Process (B) (Lot 5) | Bio-Process (B) | Butadiene Process (C) |
| | | Process | direct fermentation | | petroleum-derived |
| | | Total $C_5$, $C_6$ carbonyl content (ppm)* | 4 | 13 | ND |
| Color tone YI value of polyurethane | Color tone YI of polyurethane immediately after production | | 0.68 | 1.12 | 0.75 |
| | Color tone YI of polyurethane after elapse of 1 week | | 0.73 | 44.35 | 0.93 |

*ND: Below detection lower limit; less than 1 ppm.

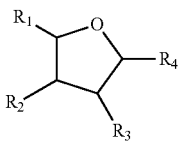

Formula (I)

wherein in formula (I), each of $R_1$ to $R_4$ independently represents a hydrogen atom, a methyl group, a formyl group or an acetyl group, with the proviso that one of $R_1$ to $R_4$ is a formyl group or an acetyl group, and the total number of carbon atoms contained in respective groups of $R_1$ to $R_4$ is 2 or less.

3. The method for producing a polyester according to claim 1,
wherein the cyclic carbonyl compound having a carbon atom number of 5 or 6 contains a compound having a structure represented by the following formula (II):

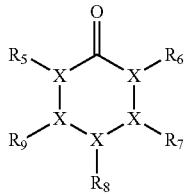

Formula (II)

wherein in formula (II), X represents a carbon atom or an oxygen atom, with the proviso that 1 X is an oxygen atom, each of $R_5$ to $R_9$ independently represents a methyl group or a hydrogen atom, and the total number of carbon atoms contained in respective groups of $R_5$ to $R_9$ is 1 or less.

4. The method for producing a polyester according to claim 1,
wherein the cyclic carbonyl compound having a carbon atom number of 5 or 6 contains a compound having a structure represented by the following formula (III) and a content of the compound having a structure represented by formula (III) in the diol is 6 ppm by mass or less:

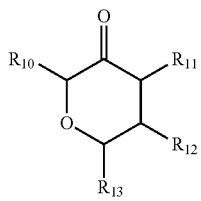

Formula (III)

wherein in formula (III), each of $R_{10}$ to $R_{13}$ independently represents a methyl group or a hydrogen atom, and the total number of carbon atoms contained in respective groups of $R_{10}$ to $R_{13}$ is 1 or less.

5. The method for producing a polyester according to claim 1,
wherein the diol is 1,4-butanediol,
the dicarboxylic acid component is at least one of a terephthalic acid and a terephthalic acid alkylate, and
the polyester is polybutylene terephthalate.

6. The method for producing a polyester according to claim 5,
wherein the 1,4-butanediol contains from 1 to 99 ppm by mass of 1-acetoxy-4-hydroxybutane.

7. The method for producing a polyester according to claim 1,
wherein a content of a nitrogen atom compound in the diol is from 0.1 to 50 ppm by mass in terms of nitrogen atom.

8. The method for producing a polyester according to claim 1, further comprising, prior to said performing a reaction, subjecting a biomass resource to a fermentation process wherein said fermentation process comprises pretreating said biomass resource and further subjecting the biomass resource to saccharification.

9. A method for producing a polyester polyol, comprising:
performing reaction by using, as raw materials, a dicarboxylic acid component, and a diol produced directly from a biomass-resource-derived substance by a fermentation process,
wherein a content of a cyclic carbonyl compound having a carbon atom number of 5 or 6 in the diol is from 0.01 ppm to 12 ppm by mass, and
wherein said diol produced directly from a biomass-resource-derived substance by a fermentation process is selected from the group consisting of ethylene glycol, 2-methyl-1,3-propanediol, neopentyl glycol, 1,4-butanediol, 1,5-pentanediol, 1,6-hexanediol, 1,4-cyclohexanediol, 1,4-cyclohexanedimethanol, and isosorbide.

10. The method for producing a polyester polyol according to claim 9,
wherein the cyclic carbonyl compound having a carbon atom number of 5 or 6 contains a compound having a structure represented by the following formula (I):

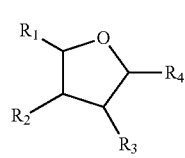

Formula (I)

wherein in formula (I), each of $R_1$ to $R_4$ independently represents a hydrogen atom, a methyl group, a formyl group or an acetyl group, with the proviso that one of $R_1$ to $R_4$ is a formyl group or an acetyl group, and the total number of carbon atoms contained in respective groups of $R_1$ to $R_4$ is 2 or less.

11. The method for producing a polyester polyol according to claim 9,
wherein the cyclic carbonyl compound having a carbon atom number of 5 or 6 contains a compound having a structure represented by the following formula (II):

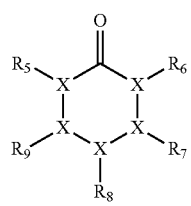

Formula (II)

wherein in formula (II), X represents a carbon atom or an oxygen atom, with the proviso that 1 X is an oxygen atom, each of $R_5$ to $R_9$ independently represents a methyl group or a hydrogen atom, and the total number of carbon atoms contained in respective groups of $R_5$ to $R_9$ is 1 or less.

12. The method for producing a polyester polyol according to claim 9,
wherein the cyclic carbonyl compound having a carbon atom number of 5 or 6 contains a compound having a structure represented by the following formula (III):

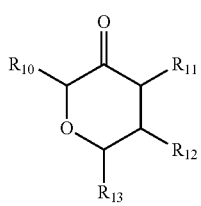

Formula (III)

wherein in formula (III), each of $R_{10}$ to $R_{13}$ independently represents a methyl group or a hydrogen atom, and the total number of carbon atoms contained in respective groups of $R_{10}$ to $R_{13}$ is 1 or less.

13. The method for producing a polyester polyol according to claim 10,
wherein the diol is 1,4-butanediol,
the dicarboxylic acid component is adipic acid, and
the polyester polyol is polybutylene adipate.

14. The method for producing a polyester polyol according to claim 13,
wherein the 1,4-butanediol contains from 1 to 99 ppm by mass of 1-acetoxy-4-hydroxybutane.

15. The method for producing a polyester polyol according to claim 9,
wherein a content of a nitrogen atom compound in the diol is from 0.1 to 50 ppm by mass in terms of nitrogen atom.

16. The method for producing a polyester polyol according to claim 9, further comprising prior to said performing reaction subjecting a biomass resource to a fermentation process wherein said fermentation process comprises pretreating said biomass resource and further subjecting the biomass resource to saccharification.

17. A method for producing a polyurethane, comprising:
reacting a polyester polyol produced by the production method of a polyester polyol according to claim 9 with an isocyanate compound.

18. A method for producing a polyurethane, comprising:
reacting a polyester polyol and an isocyanate compound, wherein the polyester polyol is produced by an esterification and/or transesterification reaction of a dicarboxylic acid and a diol, wherein the diol is produced directly from a biomass-resource-derived substance by a fermentation process and a content of a cyclic carbonyl compound having a carbon atom number of 5 or 6 in the diol is from 0.01 ppm to 12 ppm by mass, and
wherein said diol produced directly from a biomass-resource-derived substance by a fermentation process is selected from the group consisting of ethylene glycol, 2-methyl-1,3-propanediol, neopentyl glycol, 1,4-butanediol, 1,5-pentanediol, 1,6-hexanediol, 1,4-cyclohexanediol, 1,4-cyclohexanedimethanol, and isosorbide.

19. The method for producing a polyurethane according to claim 18,
wherein the cyclic carbonyl compound having a carbon atom number of 5 or 6 contains a compound having a structure represented by the following formula (I):

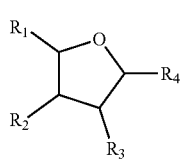

Formula (I)

wherein in formula (I), each of $R_1$ to $R_4$ independently represents a hydrogen atom, a methyl group, a formyl group or an acetyl group, with the proviso that one of $R_1$ to $R_4$ is a formyl group or an acetyl group, and the total number of carbon atoms contained in respective groups of $R_1$ to $R_4$ is 2 or less.

20. The method for producing a polyurethane according to claim 18,
wherein the cyclic carbonyl compound having a carbon atom number of 5 or 6 contains a compound having a structure represented by the following formula (II):

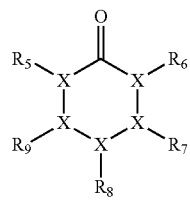

Formula (II)

wherein in formula (II), X represents a carbon atom or an oxygen atom, with the proviso that 1 X is an oxygen atom, each of $R_5$ to $R_9$ independently represents a methyl group or a hydrogen atom, and the total number of carbon atoms contained in respective groups of $R_5$ to $R_9$ is 1 or less.

21. The method for producing a polyurethane according to claim 18,
wherein the cyclic carbonyl compound having a carbon atom number of 5 or 6 contains a compound having a structure represented by the following formula (III) and a content of the compound having a structure represented by formula (III) in the diol is 6 ppm by mass or less:

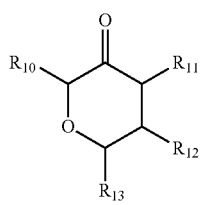

Formula (III)

wherein in formula (III), each of $R_{10}$ to $R_{13}$ independently represents a methyl group or a hydrogen atom, and the total number of carbon atoms contained in respective groups of $R_{10}$ to $R_{13}$ is 1 or less.

22. The method for producing a polyurethane according to claim 18,
   wherein the diol is 1,4-butanediol, and
   the polyester polyol is polybutylene adipate.

23. The method for producing a polyurethane according to claim 22,
   wherein the 1,4-butanediol contains from 1 to 99 ppm by mass of 1-acetoxy-4-hydroxybutane.

24. The method for producing a polyurethane according to claim 18,
   wherein a content of a nitrogen atom compound in the diol is from 0.1 to 50 ppm by mass in terms of nitrogen atom.

25. The method for producing a polyurethane according to claim 18, further comprising prior to said reacting a polyester polyol and an isocyanate compound, subjecting a biomass resource to a fermentation process wherein said fermentation process comprises pretreating said biomass resource and further subjecting the biomass resource to saccharification to produce said diol.

* * * * *